（12） United States Patent
Yeung

(10) Patent No.: US 10,123,845 B2
(45) Date of Patent: *Nov. 13, 2018

(54) ROBOTIC DEVICES AND SYSTEMS FOR PERFORMING SINGLE INCISION PROCEDURES AND NATURAL ORIFICE TRANSLUMENAL ENDOSCOPIC SURGICAL PROCEDURES, AND METHODS OF CONFIGURING ROBOTIC DEVICES AND SYSTEMS

(71) Applicant: Bio-Medical Engineering (HK) Limited, Hong Kong (CN)

(72) Inventor: Chung Kwong Yeung, Hong Kong (CN)

(73) Assignee: Bio-Medical Engineering (HK) Limited, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/814,140

(22) Filed: Nov. 15, 2017

(65) Prior Publication Data

US 2018/0071038 A1    Mar. 15, 2018

Related U.S. Application Data

(63) Continuation of application No. 15/340,678, filed on Nov. 1, 2016, now Pat. No. 9,855,108, which is a
(Continued)

(51) Int. Cl.
*A61B 34/35*     (2016.01)
*A61B 17/00*     (2006.01)
(Continued)

(52) U.S. Cl.
CPC ........ *A61B 34/35* (2016.02); *A61B 17/00234* (2013.01); *A61B 17/3421* (2013.01);
(Continued)

(58) Field of Classification Search
CPC .......... A61B 17/00234; A61B 17/3421; A61B 18/1445; A61B 1/00147; A61B 1/05;
(Continued)

(56) References Cited

U.S. PATENT DOCUMENTS 5,792,135 A    8/1998 Madhani
7,090,637 B2   8/2006 Danitz et al.
(Continued)

FOREIGN PATENT DOCUMENTS

AU    2013245548 A1    11/2013
CN    101106951 A      1/2008
(Continued)

OTHER PUBLICATIONS

International Search Report and Written Opinion of the International Searching Authority dated Aug. 18, 2017 in connection with International Patent Application No. PCT/CN/2017/086202.
(Continued)

*Primary Examiner* — Michael Peffley
(74) *Attorney, Agent, or Firm* — Baker & McKenzie LLP

(57) ABSTRACT

Example embodiments relate to surgical systems comprising an end-effector assembly and arm assembly. The end-effector assembly may include a first instrument assembly having a first instrument and first instrument driven portion configurable to be driven to move the first instrument relative to a first axis. The arm assembly may include first and second arm assembly bodies, first arm assembly joint portion for joining the first and second arm assembly bodies, first instrument drive assembly, and first arm assembly drive assembly. The first instrument drive assembly may include a first integrated motor and first instrument drive portion controllable by the first integrated motor to drive the first instrument driven portion. The first arm assembly drive assembly may include a second integrated motor and first
(Continued)

arm assembly drive portion controllable by the second integrated motor to drive the first arm assembly body to move relative to the second arm assembly body.

17 Claims, 32 Drawing Sheets

Related U.S. Application Data continuation-in-part of application No. 14/693,207, filed on Apr. 22, 2015, application No. 15/814,140, filed on Nov. 15, 2017, which is a continuation of application No. 15/044,895, filed on Feb. 16, 2016, which is a continuation-in-part of application No. 14/693,207, filed on Apr. 22, 2015, application No. 15/814,140, filed on Nov. 15, 2017, which is a continuation of application No. 15/044,889, filed on Feb. 16, 2016, now Pat. No. 9,737,372, which is a continuation-in-part of application No. 14/693,207, filed on Apr. 22, 2015.

(60) Provisional application No. 61/982,717, filed on Apr. 22, 2014.

(51) Int. Cl.
*A61B 34/00* (2016.01)
*A61B 90/00* (2016.01)
*A61B 34/37* (2016.01)
*A61B 18/00* (2006.01)
*A61B 18/14* (2006.01)
*A61B 34/30* (2016.01)
*A61B 17/34* (2006.01)
*A61B 90/30* (2016.01)
*A61B 1/313* (2006.01)
*A61B 1/05* (2006.01)
*A61B 1/00* (2006.01)

(52) U.S. Cl.
CPC .............. *A61B 34/25* (2016.02); *A61B 34/30* (2016.02); *A61B 34/37* (2016.02); *A61B 34/76* (2016.02); *A61B 90/361* (2016.02); *A61B 1/00147* (2013.01); *A61B 1/05* (2013.01); *A61B 1/3132* (2013.01); *A61B 18/1442* (2013.01); *A61B 18/1445* (2013.01); *A61B 2017/00283* (2013.01); *A61B 2017/345* (2013.01); *A61B 2017/346* (2013.01); *A61B 2017/3445* (2013.01); *A61B 2018/00589* (2013.01); *A61B 2018/00601* (2013.01); *A61B 2018/00982* (2013.01); *A61B 2018/146* (2013.01); *A61B 2034/302* (2016.02); *A61B 2034/305* (2016.02); *A61B 2090/309* (2016.02); *A61B 2090/3612* (2016.02); *Y10S 901/02* (2013.01); *Y10S 901/27* (2013.01)

(58) Field of Classification Search
CPC ........ A61B 1/3132; A61B 2017/00283; A61B 2017/3445; A61B 2017/346; A61B 2018/00589; A61B 2018/00601; A61B 2018/00982; A61B 2018/146; A61B 2034/305; A61B 34/25; A61B 34/30; A61B 34/35; A61B 34/37; A61B 34/76; Y10S 901/02; Y10S 901/27
See application file for complete search history.

(56) References Cited

U.S. PATENT DOCUMENTS

| | | | |
|---|---|---|---|
| 7,410,483 B2 | 8/2008 | Danitz et al. | |
| 7,422,592 B2* | 9/2008 | Morley | A61B 18/1445 606/49 |
| 8,083,667 B2 | 12/2011 | Cooper et al. | |
| 8,551,114 B2* | 10/2013 | Ramos de la Pena | A61B 34/70 606/1 |
| 8,672,833 B2* | 3/2014 | Cooper | A61B 1/00087 600/104 |
| 8,891,924 B2 | 11/2014 | Yeung et al. | |
| 9,010,214 B2 | 4/2015 | Markvicka | |
| 9,060,798 B2 | 6/2015 | Harper et al. | |
| 2005/0096502 A1 | 5/2005 | Khalili | |
| 2007/0123855 A1 | 5/2007 | Morley et al. | |
| 2007/0175961 A1 | 8/2007 | Shelton, IV et al. | |
| 2007/0255273 A1 | 11/2007 | Fernandez et al. | |
| 2007/0287884 A1 | 12/2007 | Schena | |
| 2009/0187198 A1 | 7/2009 | Weitzner | |
| 2010/0036198 A1 | 2/2010 | Tacchino et al. | |
| 2010/0137681 A1 | 6/2010 | Ewers et al. | |
| 2010/0331857 A1 | 12/2010 | Doyle et al. | |
| 2011/0118736 A1 | 5/2011 | Harper et al. | |
| 2011/0213384 A1 | 9/2011 | Jeong | |
| 2013/0131695 A1* | 5/2013 | Scarfogliero | A61B 19/2203 606/130 |
| 2013/0144395 A1 | 6/2013 | Stefanchik et al. | |
| 2013/0289579 A1 | 10/2013 | Yeung et al. | |
| 2013/0345717 A1* | 12/2013 | Markvicka | A61B 34/30 606/130 |
| 2014/0128882 A1 | 5/2014 | Kwak et al. | |
| 2015/0238254 A1 | 8/2015 | Seddon et al. | |
| 2015/0282875 A1 | 10/2015 | Harper et al. | |
| 2015/0297299 A1 | 10/2015 | Yeung et al. | |
| 2016/0157948 A1 | 6/2016 | Yeung | |
| 2017/0035526 A1* | 2/2017 | Farritor | A61B 90/361 |
| 2017/0042623 A1 | 2/2017 | Yeung | |
| 2017/0042624 A1 | 2/2017 | Yeung | |

FOREIGN PATENT DOCUMENTS

| | | |
|---|---|---|
| CN | 201135461 Y | 10/2008 |
| CN | 101500470 A | 8/2009 |
| CN | 101791247 A1 | 8/2010 |
| CN | 102100573 A | 6/2011 |
| CN | 101400293 B | 7/2011 |
| CN | 201968771 U | 9/2011 |
| CN | 102614006 A | 8/2012 |
| CN | 202505440 U | 10/2012 |
| CN | 202637006 U | 1/2013 |
| CN | 203290975 U | 11/2013 |
| CN | 103431913 A | 12/2013 |
| CN | 103533898 A | 1/2014 |
| CN | 103582462 A | 2/2014 |
| CN | 104224324 A | 12/2014 |
| CN | 104783844 A | 7/2015 |
| CN | 104883991 A | 9/2015 |
| CN | 105358072 A | 2/2016 |
| CN | 105816242 A | 8/2016 |
| WO | 95/10241 A2 | 4/1995 |
| WO | 2007/146987 A2 | 12/2007 |
| WO | 2010151438 A1 | 12/2010 |
| WO | 2014-085718 A1 | 6/2014 |
| WO | 2015161677 A1 | 10/2015 |
| WO | 2016059369 A1 | 4/2016 |

OTHER PUBLICATIONS

International Search Report and Written Opinion issued by the International Searching Authority dated Aug. 22, 2017 in connection with International Patent Application No. PCT/CN2017/086203.

(56) References Cited

OTHER PUBLICATIONS

International Search Report and Written Opinion issued by the International Searching Authority dated May 25, 2016 in connection with International Patent Application No. PCT/CN2016/076376, 10 pages.
International Search Report and Written Opinion issued by the International Searching Authority dated May 27, 2016 in connection with International Patent Application No. PCT/CN2016/076385, 16 pages.
International Search Report issued by the International Searching Authority dated Jul. 14, 2015 in connection with International Patent Application No. PCT/CN2015/000284.
Written Opinion of the International Searching Authority dated Jul. 14, 2015 in connection with International Patent Application No. PCT/CN2015/000284.
International Search Report and Written Opinion issued by the International Searching Authority dated Aug. 25, 2017 in connection with International Patent Application No. PCT/CN2017/086204.

* cited by examiner

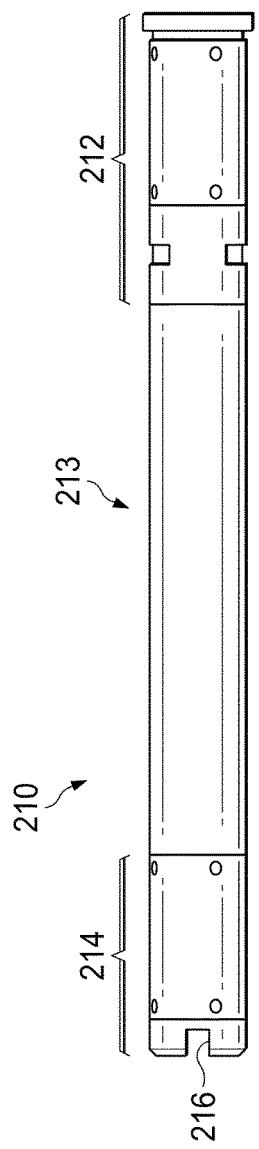
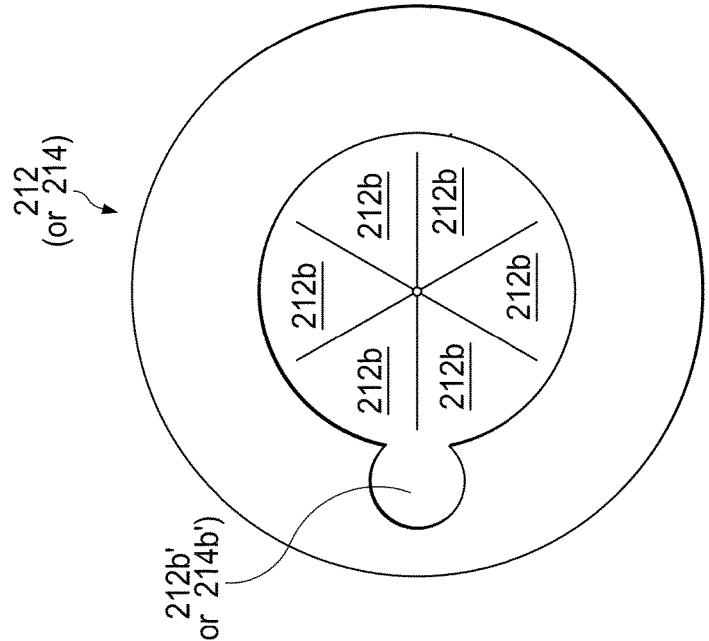
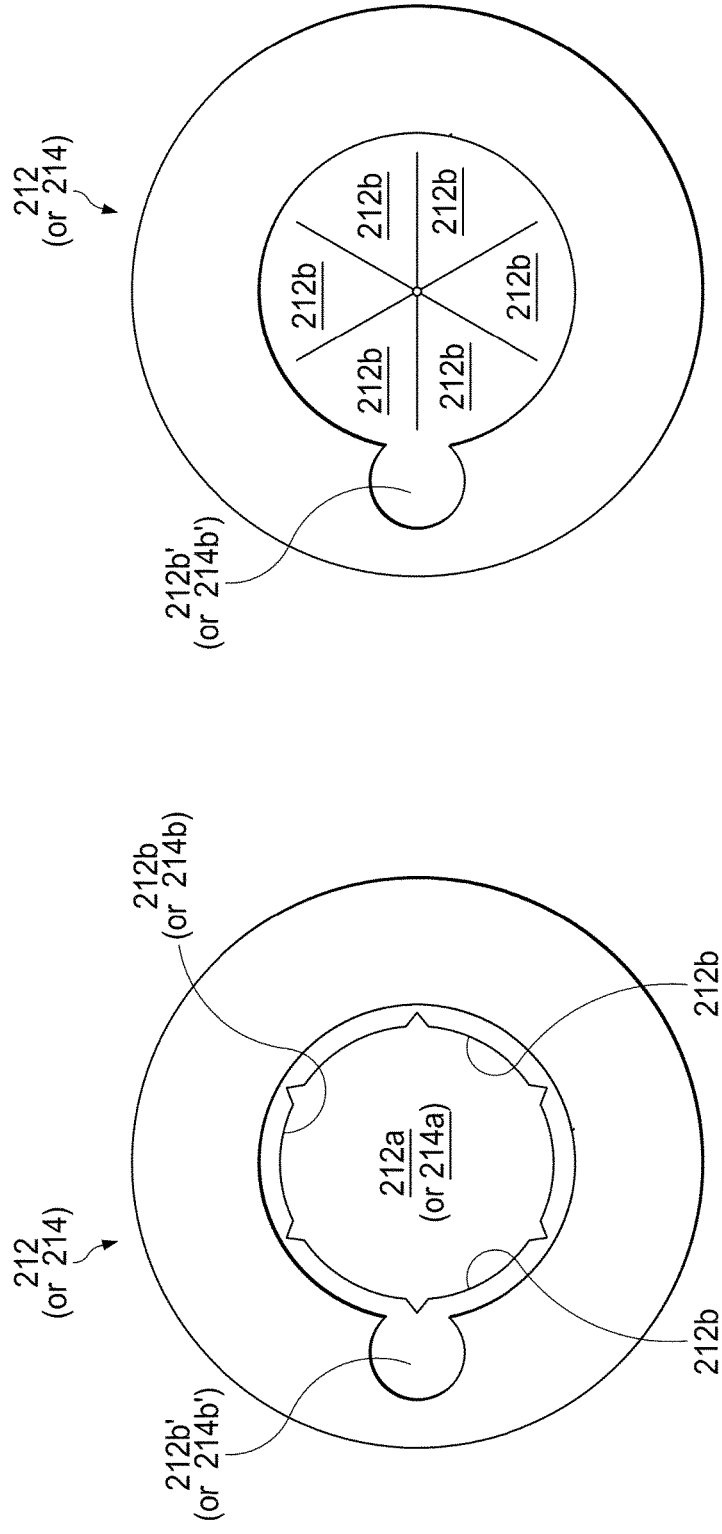
FIG. 4B
FIG. 4D
FIG. 4C

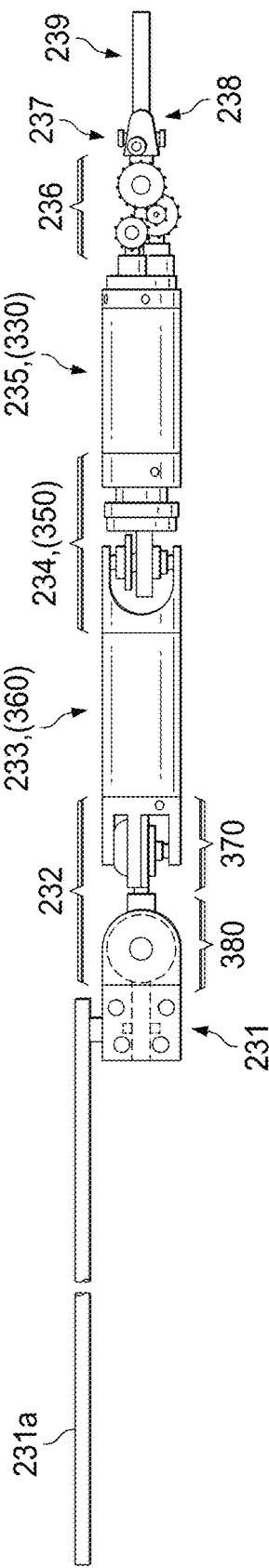
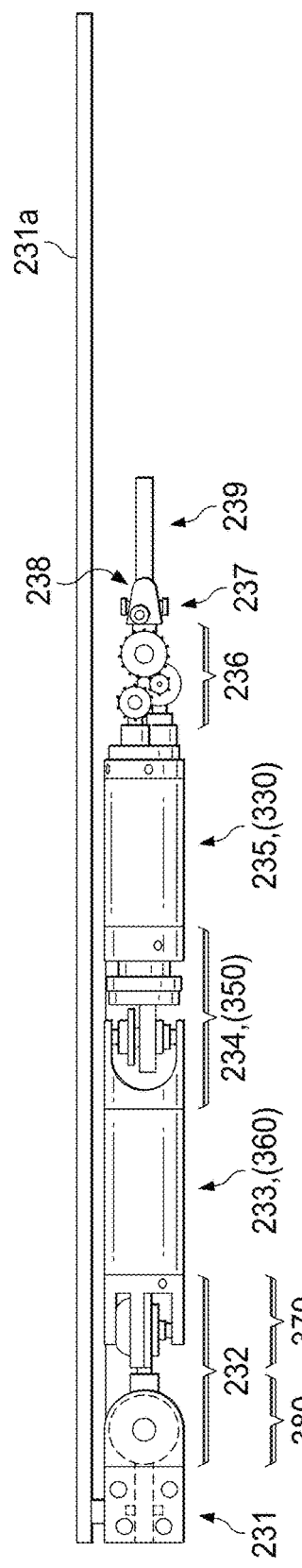
FIG. 5A
FIG. 5B

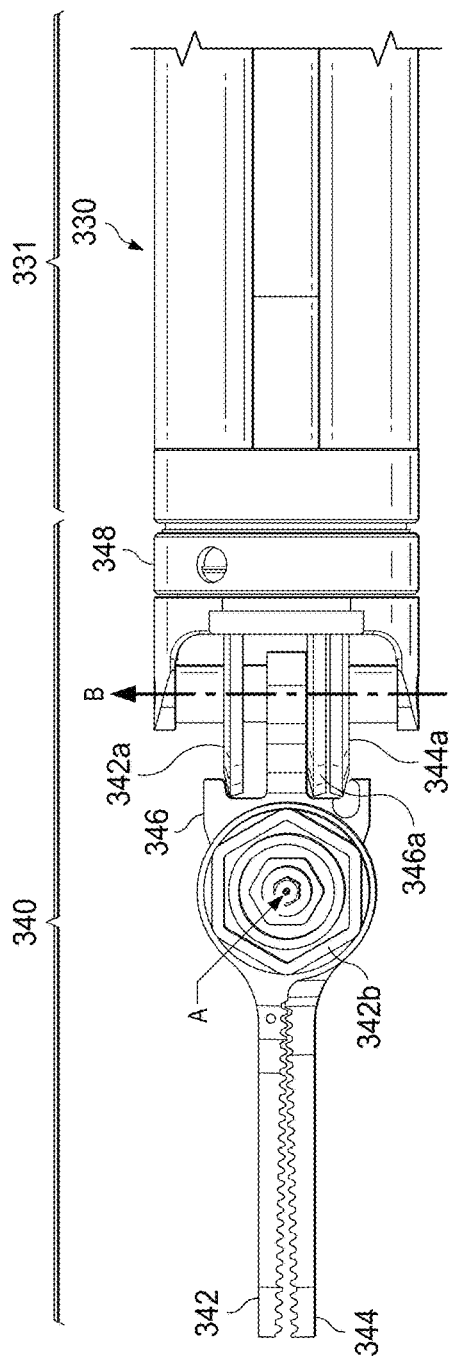
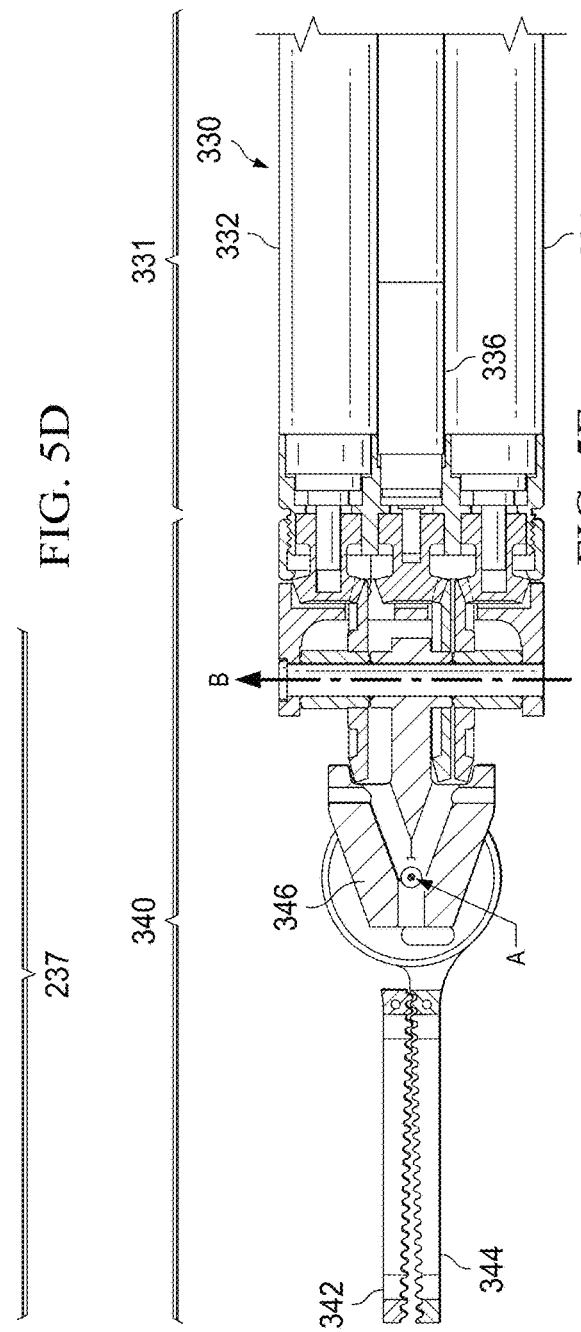
FIG. 5D
FIG. 5E

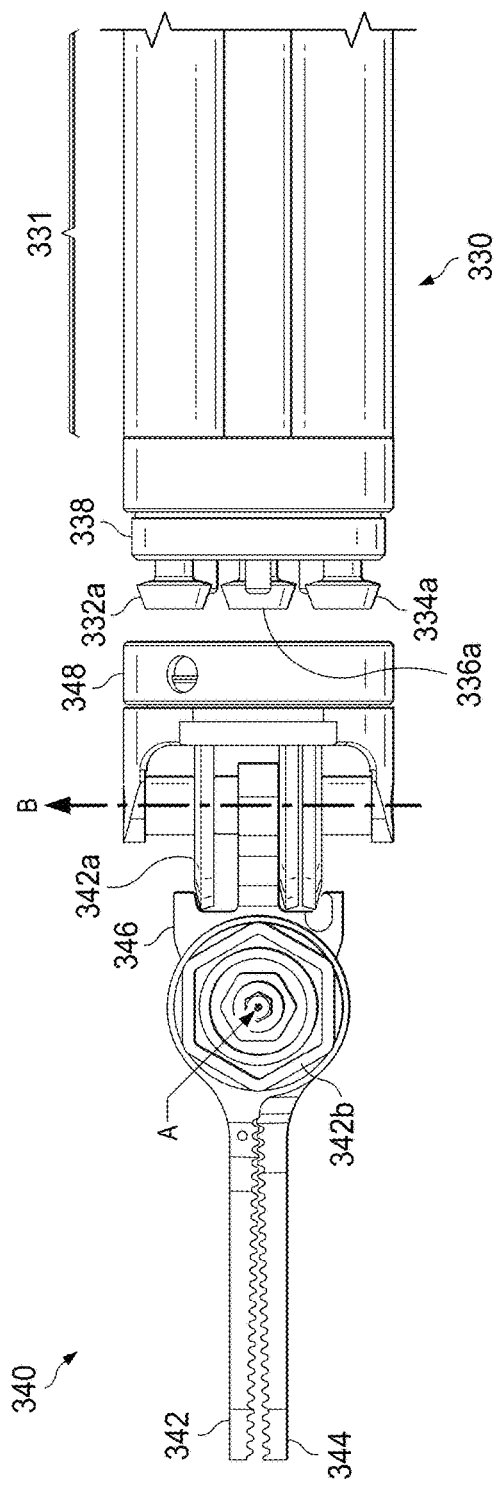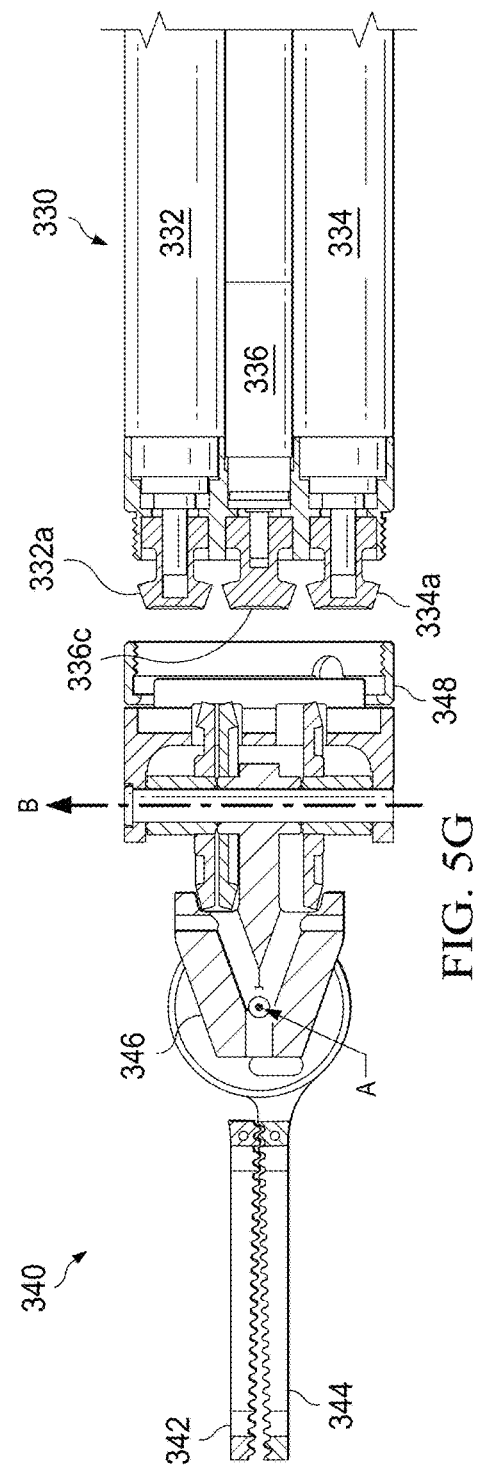
FIG. 5F
FIG. 5G

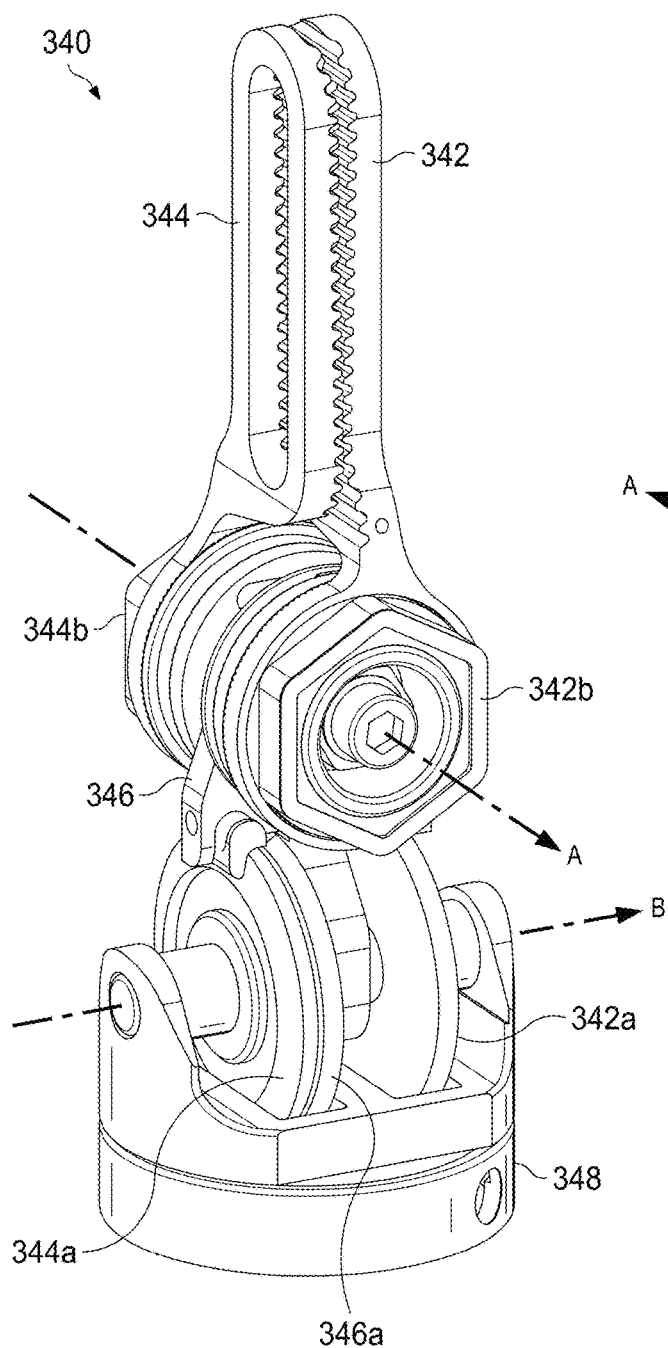
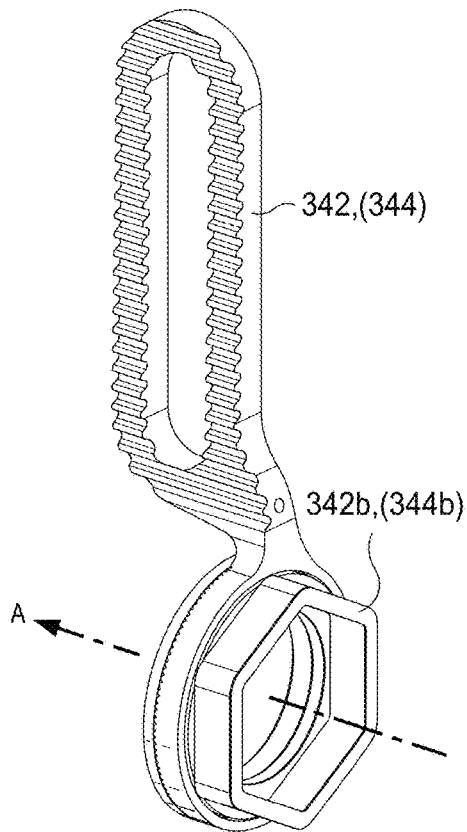
FIG. 5H
FIG. 5I

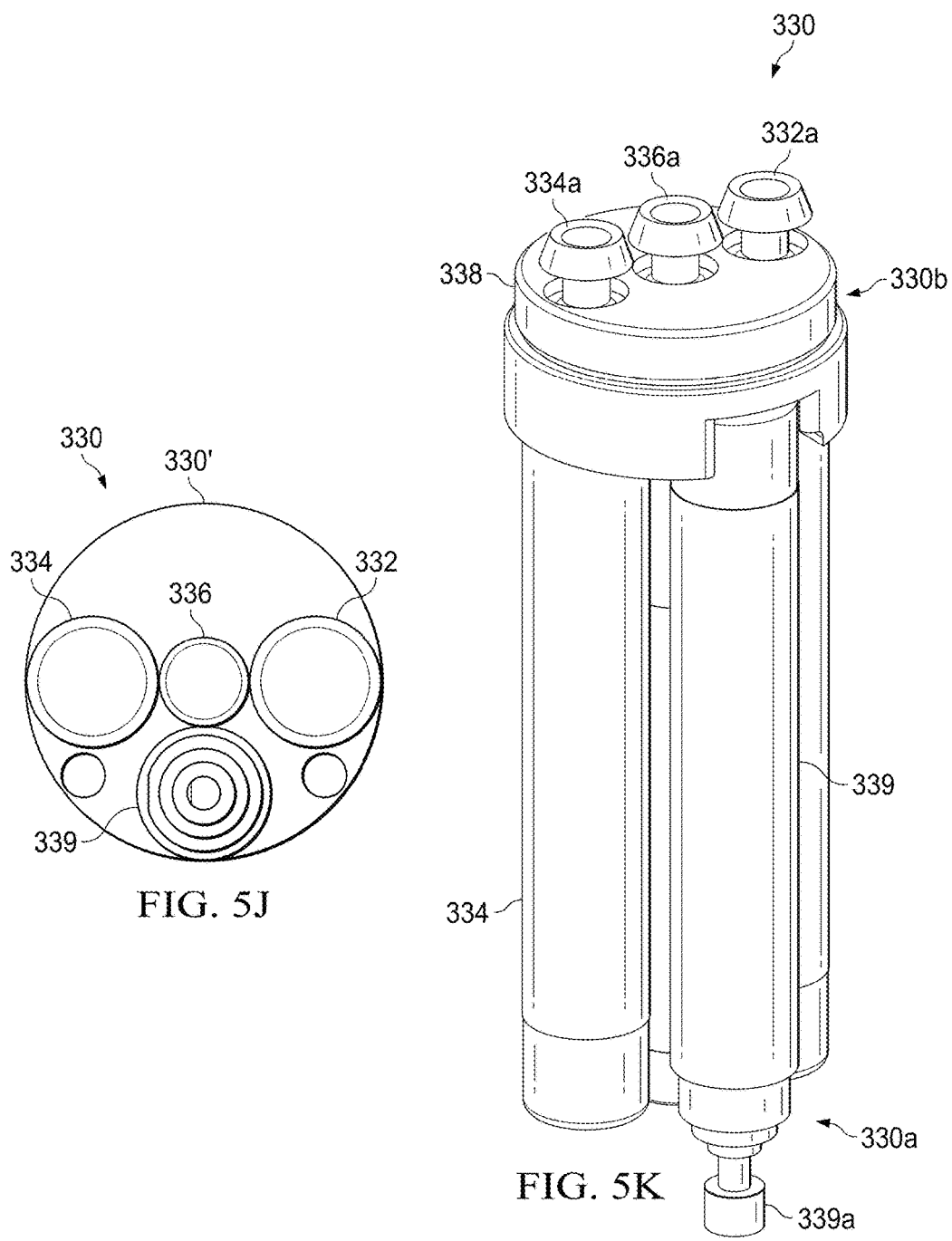

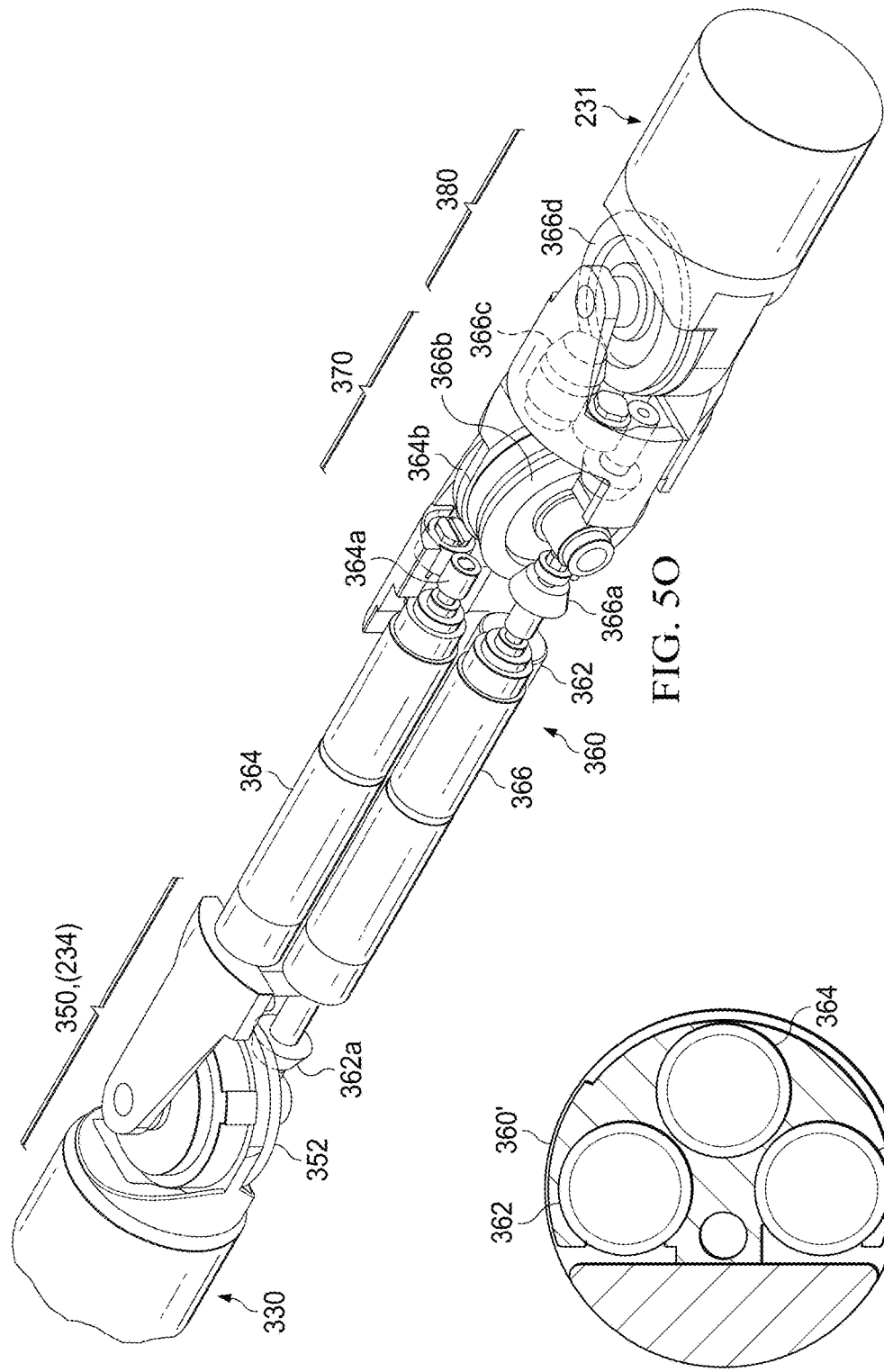

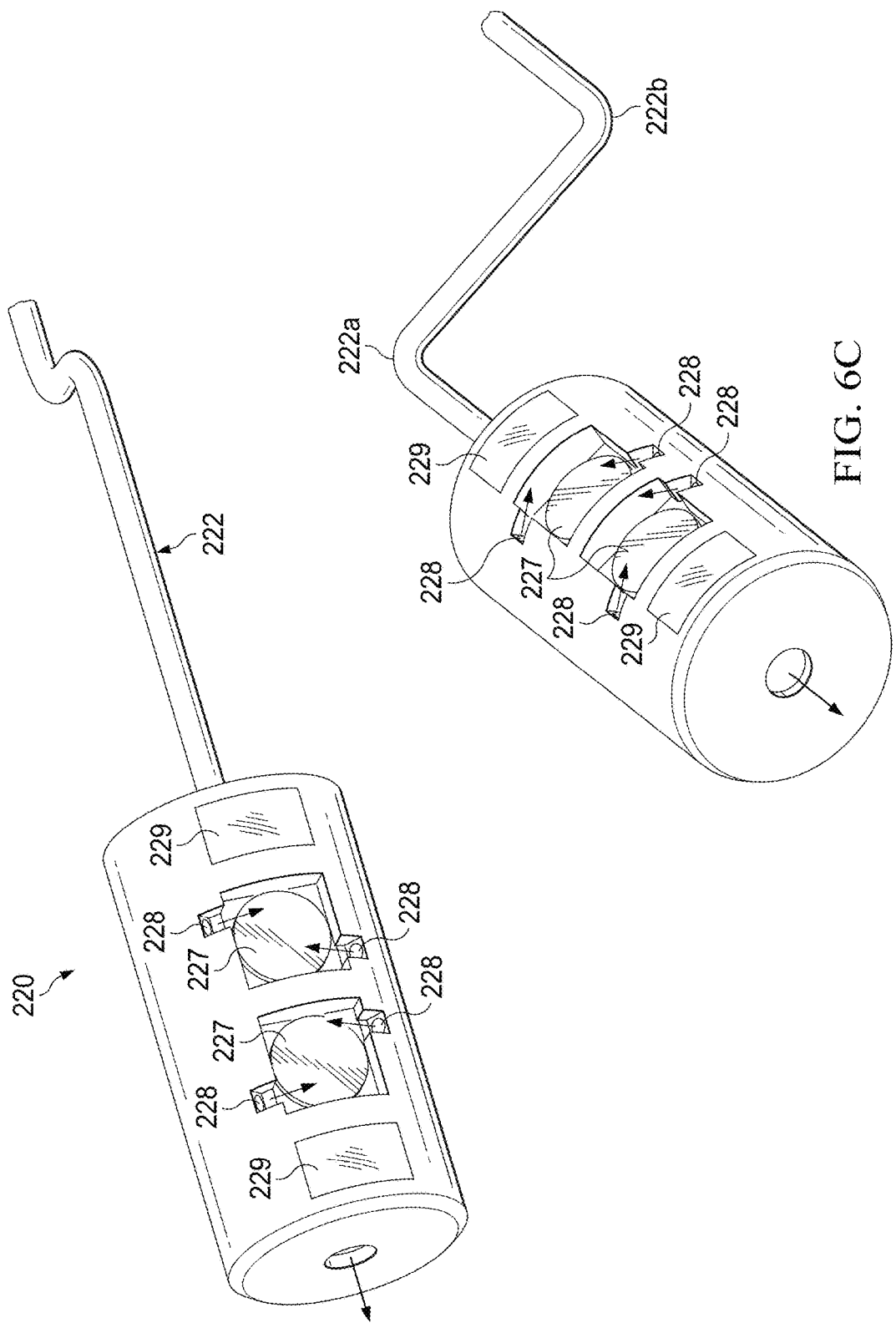

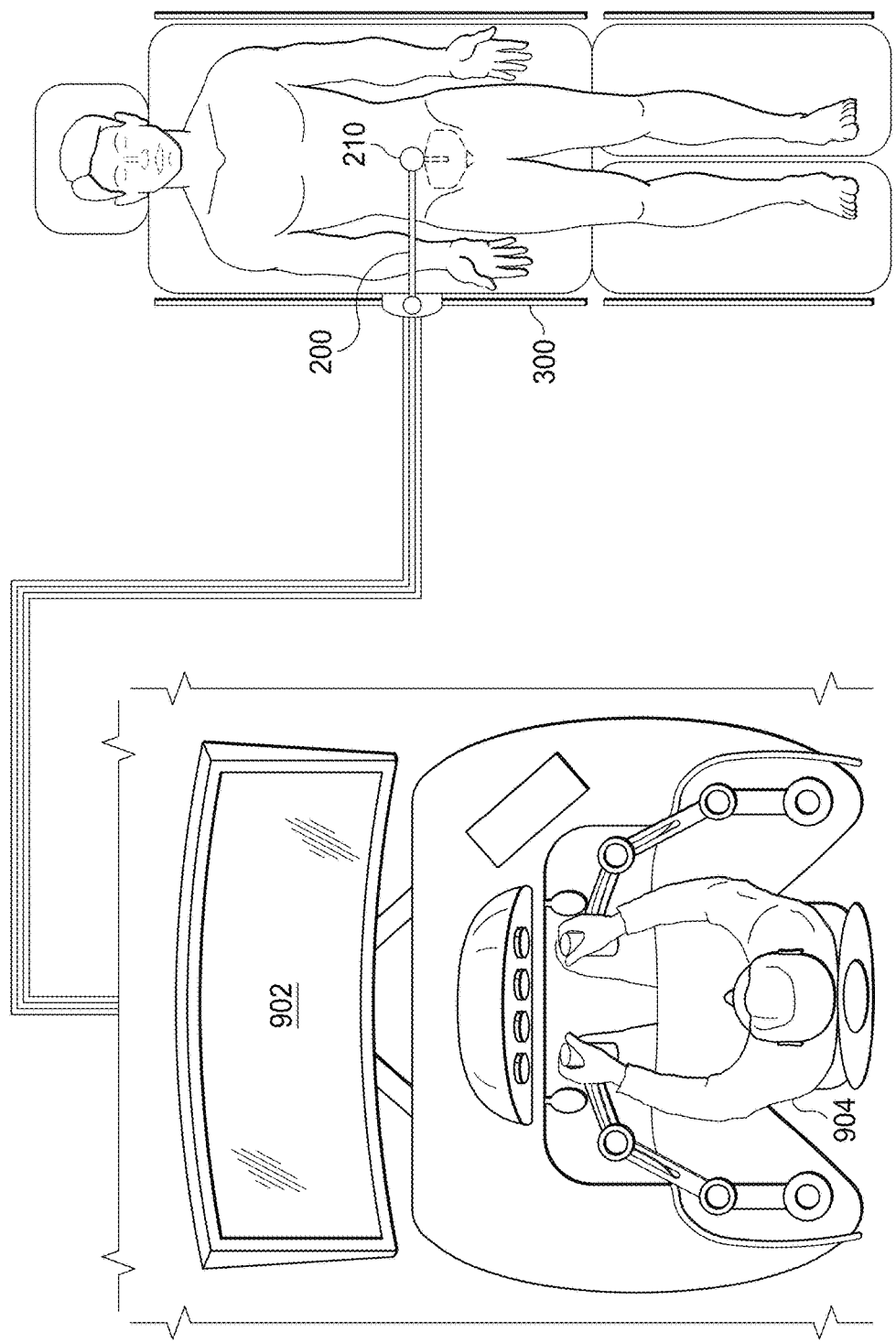

ROBOTIC DEVICES AND SYSTEMS FOR PERFORMING SINGLE INCISION PROCEDURES AND NATURAL ORIFICE TRANSLUMENAL ENDOSCOPIC SURGICAL PROCEDURES, AND METHODS OF CONFIGURING ROBOTIC DEVICES AND SYSTEMS

CROSS-REFERENCE TO RELATED APPLICATIONS

This application is a continuation of U.S. application Ser. No. 15/340,678 (filed on Nov. 1, 2016 and granted as U.S. Pat. No. 9,855,108, which is a continuation-in-part of U.S. application Ser. No. 14/693,207 (filed on Apr. 22, 2015, which claims priority to U.S. Provisional Application No. 61/982,717, filed on Apr. 22, 2014), U.S. application Ser. No. 15/044,895 (filed on Feb. 16, 2016, which is a continuation-in-part of U.S. application Ser. No. 14/693,207), and U.S. application Ser. No. 15/044,889 (filed on Feb. 16, 2016 and granted as U.S. Pat. No. 9,737,372, which is a continuation-in-part of U.S. application Ser. No. 14/693,207)), the contents of all of which are hereby expressly incorporated by reference in their entirety, including the contents and teachings of any references contained therein.

BACKGROUND

The present disclosure relates generally to systems, devices, and methods, and more specifically, relates to systems, devices, and methods for use in performing procedures via a single incision or a natural orifice.

Conventional surgical procedures will generally require one or more large incisions to a patient in order for the surgical team to perform a surgical action. With the advancement of medical science and technology, most conventional open surgical procedures have been largely replaced with minimally invasive surgery (MIS) procedures. Recent developments in respect to computer-assisted and/or robotic surgical technology have contributed to advancements in MIS, including the ability to translate a surgeon's desired actions into movements of robotic instruments inside the body cavity of a patient.

BRIEF SUMMARY

Despite recent developments in modern medical science and technology, it is recognized in the present disclosure that one or more problems are encountered in modern surgical technology and methodology. For example, a typical MIS procedure requires multiple incisions to a patient in order to allow access via the incisions for the insertion of a camera and various other laparoscopic instruments into the body cavity of the patient.

As another example, surgical robotic devices oftentimes encounter difficulties during surgical procedures due to insufficient anchoring and/or reactive forces to stabilize against forces that are desired and/or necessary to be applied during surgical actions.

It is also recognized in the present disclosure that surgical robotic systems face difficulties in providing an instrument, such as a cutting or gripping instrument attached to the end of a surgical robotic arm, with access to all or even most parts, areas, and/or quadrants of abdominal cavity of a patient. That is, after the surgical robotic arm is inserted in the abdominal cavity of the patient and ready to perform a surgical action, the instrument attached to the end of the surgical robotic arm is typically limited to access only certain parts, areas, and quadrants of the abdominal cavity of the patient.

In yet another example, known surgical robotic systems typically provide only between one to two surgical robotic arms per access or opening (such as an incision or a natural orifice) of the patient. In this regard, one or more additional incisions will be required for the insertion of a camera and various laparoscopic instruments into the abdominal cavity of the patient.

As another example, while known surgical robotic systems have been designed for use in an abdominal cavity of a patient to perform forward-directed surgical procedures, such systems have not been designed for and may encounter problems when applied in situations requiring reverse-directed surgical procedures. For example, such known surgical robotic systems have not been designed for deployment through a natural orifice, such as a rectum or vagina, for performing natural orifice transluminal endoscopic surgery (or NOTES), such as pelvic gynecological and/or urological procedures. Such systems may encounter one or more problems, such as the inability to access certain organs, tissues, or other surgical sites upon insertion into the natural orifice.

Present example embodiments relate generally to systems, devices, and methods for addressing one or more problems in surgical robotic systems, devices, and methods, including those described above and herein.

In an exemplary embodiment, a surgical system is described in the present disclosure. The surgical system may be for use in performing natural orifice transluminal endoscopic surgery (NOTES). The surgical system may comprise an end-effector assembly, a first arm assembly, and a second arm assembly. The may include a first instrument assembly and a wrist assembly. The first instrument assembly may include a first instrument for performing a surgical action. The first instrument assembly may further include a first instrument driven portion configurable to be driven in such a way as to move the first instrument relative to a first axis. The wrist assembly may be securable to the first instrument assembly. The wrist assembly may include a wrist driven portion configurable to be driven in such a way as to move the first instrument relative to a second axis, the second axis being different from the first axis. The first arm assembly may be securable to the end-effector assembly. The first arm assembly may include a first arm assembly body, a first arm assembly joint portion, a wrist connector portion, a first instrument drive assembly, a wrist drive assembly, and a first arm assembly drive assembly. The first arm assembly body may include a first end and a second end opposite to the first end. The first arm assembly joint portion may be for use in joining the first arm assembly to a second arm assembly. The first arm assembly joint portion may be secured to the first end of the first arm assembly body. The wrist connector portion may be configurable to secure to the wrist assembly. The first instrument drive assembly may be securely housed in the first arm assembly body. The first instrument drive assembly may include at least a first integrated motor and a first instrument drive portion. The first instrument drive portion may be controllable by the first integrated motor to drive the first instrument driven portion when the wrist connector portion is secured to the wrist assembly. The wrist drive assembly may be securely housed in the first arm assembly body. The wrist drive assembly may include at least a second integrated motor and a wrist drive portion. The wrist drive portion may be controllable by the second integrated motor to drive the wrist driven portion when the wrist connector portion is secured to the wrist assembly. The first arm assembly drive assembly may be securely housed in the first arm assembly body. The first arm assembly drive assembly may include at least a third integrated motor and a first arm assembly drive portion. The first arm assembly drive portion may be controllable by the third integrated motor to drive the first arm assembly body to move relative to the second arm assembly.

In another exemplary embodiment, a surgical system is described in the present disclosure. The surgical system may be for use in performing natural orifice transluminal endoscopic surgery (NOTES). The surgical system may comprise an end-effector assembly and an arm assembly. The end-effector assembly may include a first instrument assembly. The first instrument assembly may include a first instrument for performing a surgical action. The first instrument assembly may also include a first instrument driven portion configurable to be driven in such a way as to move the first instrument relative to a first axis. The arm assembly may include a first arm assembly body, a second arm assembly body, a first arm assembly joint portion, an end-effector connector portion, a first instrument drive assembly, and a first arm assembly drive assembly. The first arm assembly body may include a first end and a second end opposite to the first end. The second arm assembly body may include a first end and a second end opposite to the first end. The first arm assembly joint portion may be for use in joining the first arm assembly body to the second arm assembly body. The first arm assembly joint portion may be secured to the first end of the first arm assembly body. The end-effector connector portion may be provided at the second end of the first arm assembly body. The end-effector connector portion may be configurable to secure to at least a portion of the end-effector assembly. The first instrument drive assembly may include at least a first integrated motor and a first instrument drive portion. The first instrument drive portion may be controllable by the first integrated motor to drive the first instrument driven portion when the end-effector connector portion is secured to the end-effector assembly. The first arm assembly drive assembly may include at least a second integrated motor and a first arm assembly drive portion. The first arm assembly drive portion may be controllable by the second integrated motor to drive the first arm assembly body to move relative to the second arm assembly body.

In another exemplary embodiment, a surgical system is described in the present disclosure. The surgical system may be for use in performing natural orifice transluminal endoscopic surgery (NOTES). The surgical system may comprise an end-effector assembly and a first arm assembly securable to the end-effector assembly. The end-effector assembly may include a first instrument assembly and a wrist assembly. The first instrument assembly may include a first instrument for performing a surgical action and a first instrument driven portion configurable to be driven in such a way as to move the first instrument relative to a first axis. The wrist assembly may be securable to the first instrument assembly. The wrist assembly may include a wrist driven portion configurable to be driven in such a way as to move the first instrument relative to a second axis, the second axis being different from the first axis. The first arm assembly may include a first arm assembly body, a wrist connector portion, a first instrument drive assembly, and a wrist drive assembly. The first arm assembly body may include a first end and a second end opposite to the first end. The wrist connector portion may be provided at the first end of the first arm assembly body. The wrist connector portion may be configurable to secure to the wrist assembly. The first instrument drive assembly may be securely housed in the first arm assembly body. The first instrument drive assembly may include at least a first integrated motor and a first instrument drive portion. The first instrument drive portion may be controllable by the first integrated motor to drive the first instrument driven portion when the wrist connector portion is secured to the wrist assembly. The wrist drive assembly may be securely housed in the first arm assembly body. The wrist drive assembly may include at least a second integrated motor and a wrist drive portion. The wrist drive portion may be controllable by the second integrated motor to drive the wrist driven portion when the wrist connector portion is secured to the wrist assembly.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 4B is an illustration of a side view of an example embodiment of a port assembly;

FIG. 4C is an illustration of a cross-sectional view of an example embodiment of a port assembly with a first or second gate assembly in the open position;

FIG. 4D is an illustration of a cross-sectional view of an example embodiment of a port assembly with a first or second gate assembly in the closed position;

FIG. 5A is an illustration of a side view of an example embodiment of an instrument arm assembly;

FIG. 5B is another illustration of a side view of an example embodiment of an instrument arm assembly;

FIG. 5D is an illustration of a side view of an example embodiment of an end-effector assembly secured to an arm assembly;

FIG. 5E is an illustration of a side cross-sectional view of an example embodiment of an end-effector assembly secured to an arm assembly;

FIG. 5F is an illustration of a side view of an example embodiment of an end-effector assembly unsecured from an arm assembly;

FIG. 5G is an illustration of a side cross-sectional view of an example embodiment of an end-effector assembly unsecured from an arm assembly;

FIG. 5H is an illustration of a perspective view of an example embodiment of an end-effector assembly;

FIG. 5I is an illustration of a perspective view of an example embodiment of an instrument with an insulative portion;

FIG. 5J is an illustration of a top cross-sectional view of an example embodiment of an arm assembly;

FIG. 5K is an illustration of a perspective view of an example embodiment of an arm assembly;

FIG. 5N is an illustration of a top cross-sectional view of an example embodiment of a second arm assembly;

FIG. 5O is an illustration of a transparent perspective partial view of an example embodiment of an instrument arm assembly;

FIG. 6C is an illustration of perspective views of another example embodiment of an image capturing assembly having internal temperature control assemblies;

FIG. 9A is an illustration of a perspective view of an example embodiment of a surgical device system;

Although similar reference numbers may be used to refer to similar elements in the figures for convenience, it can be appreciated that each of the various example embodiments may be considered to be distinct variations.

DETAILED DESCRIPTION

Figure 1A:
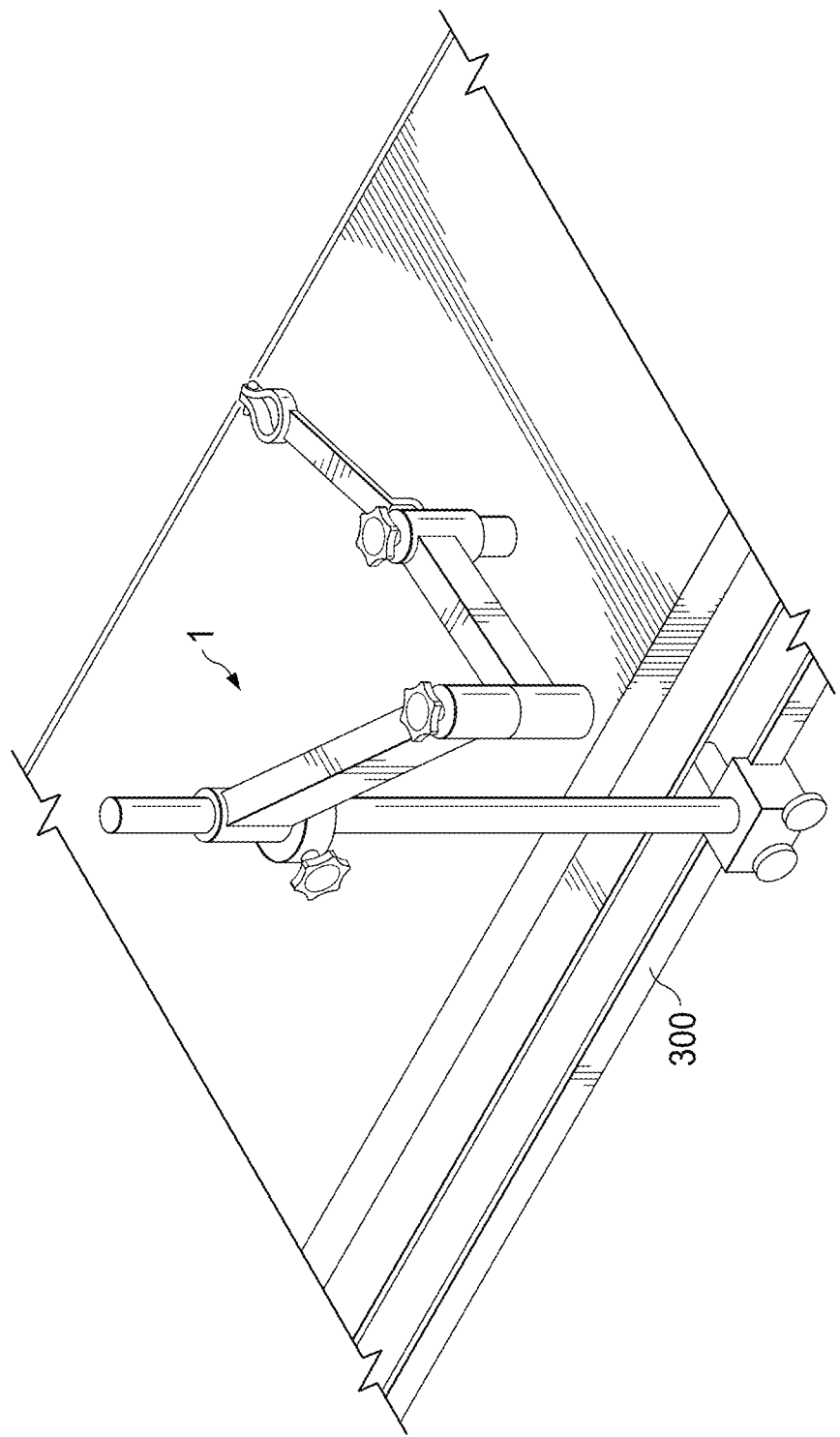
FIG. 1A is illustration of a perspective view of an example embodiment of an external anchor.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

It is recognized in the present disclosure that, despite recent developments in medical science and technology, one or more problems are encountered in modern surgical technology and methodology, including MIS. For example, a typical MIS procedure requires multiple incisions to a patient in order to allow access via the incisions for the insertion of a camera and various other laparoscopic instruments into the body cavity of the patient.

In addition to the aforementioned disadvantages pertaining to the multiple and rather large incisions, it is recognized in the present disclosure that surgical robotic systems, including surgical robotic arms (and those instruments attached to them), developed for performing robotic-assisted MIS surgical procedures also suffer from one or more problems. For example, it is recognized herein that a major technical challenge for a surgical robotic system is the difficulty in providing sufficient anchoring and/or reactive forces to stabilize against forces that are desired and/or necessary to be applied to the patient by the surgical robotic system during a surgical action. In this regard, certain surgical actions for known surgical robotic systems may require tremendous effort and time, and may not be performed properly or at all as a result of the problem of insufficient anchoring and/or reactive forces.

Another example of a problem recognized in the present disclosure as being encountered by surgical robotic systems is the difficulty in providing an instrument, such as a cutting and/or gripping instrument attached to the end of a surgical robotic arm, with access to all or even most parts, areas, and quadrants of an abdominal cavity of a patient after the surgical robotic system has been set up (or installed) and is ready to perform a surgery. That is, after the surgical robotic arm of the system has been inserted, attached, and properly set up in the abdominal cavity of the patient and is ready to perform a surgical action, the instrument attached to the end of the surgical robotic arm is typically limited to access only certain parts, areas, and quadrants of the abdominal cavity of the patient. It is recognized in the present disclosure that such problems result in large from the limited number of possible degrees of freedom that can be provided by known surgical robotic systems and arms, and more specifically, the limited number of in vivo degrees of freedom (i.e. the degrees of freedom provided within an abdominal cavity of a patient) of known surgical robotic systems and arms. In this regard, surgical robotic systems typically provide only between 2 to 4 in vivo degrees of freedom for each surgical robotic arm.

As another example, while known surgical robotic systems have been designed for use in an abdominal cavity of a patient to perform forward-directed surgical procedures, such systems have not been designed for and may encounter problems when applied in situations requiring reverse-directed surgical procedures. For example, such known surgical robotic systems have not been designed for deployment through a natural orifice, such as a rectum or vagina, for performing natural orifice transluminal endoscopic surgery (or NOTES), such as trans-vaginal gynecological procedures in women and trans-rectal urological procedures in men. Such systems may encounter one or more problems, such as the inability to access certain organs, tissues, or other surgical sites upon insertion into the natural orifice.

Surgical systems, devices, and methods, including those for use in MIS and natural orifice transluminal endoscopic surgery (or NOTES), are described in the present disclosure for addressing one or more problems of known surgical systems, devices, and methods, including those described above and in the present disclosure. It is to be understood that the principles described in the present disclosure can be applied outside of the context of MIS and/or NOTES, such as performing scientific experiments and/or procedures in environments that are not readily accessible by humans, including in a vacuum, in outer space, and/or under toxic and/or dangerous conditions, without departing from the teachings of the present disclosure.

The Surgical System (e.g., Surgical Device 200)

Figure 2A:
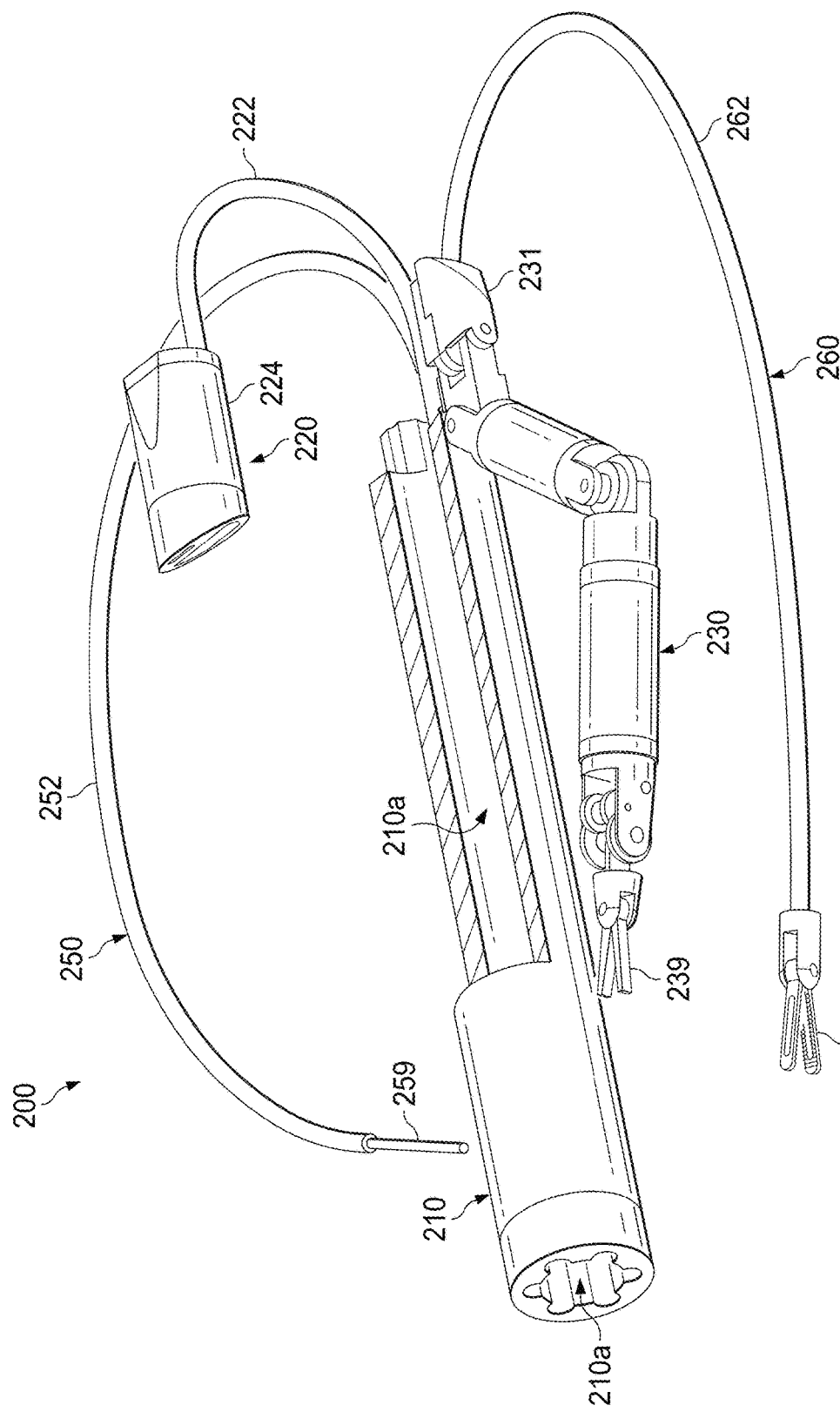
FIG. 2A is an illustration of a perspective view of an example embodiment of a surgical device configured in a reverse-directed position with one port assembly, one instrument arm assembly, and one image capturing assembly.
Figure 2B:
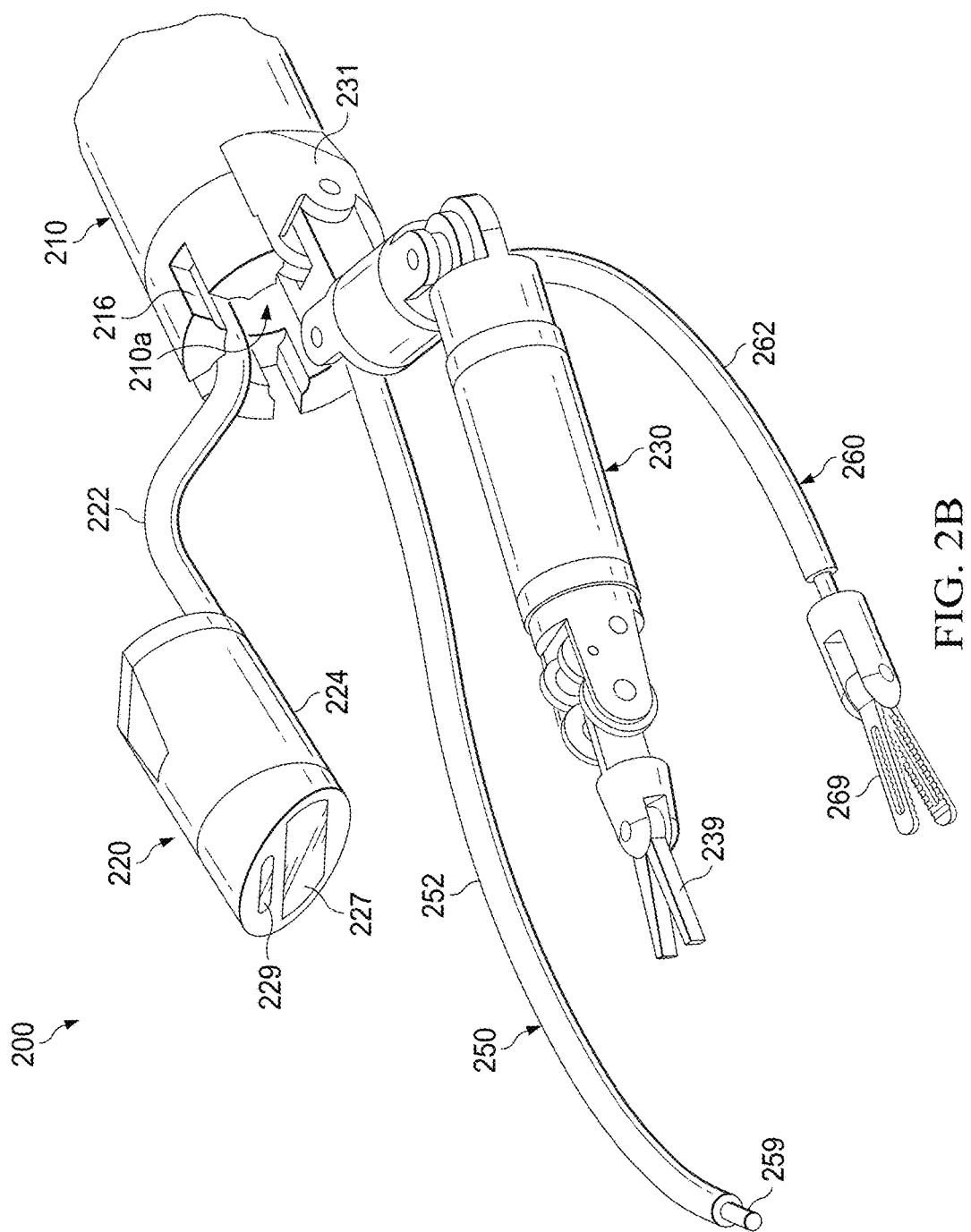
FIG. 2B is an illustration of a perspective view of an example embodiment of a surgical device configured in a forward-directed position with one port assembly, one instrument arm assembly, and one image capturing assembly.

An illustration of an example embodiment of a surgical device or system (e.g., surgical device or system 200) operable to be inserted into an abdominal cavity of a patient through a single access or opening (e.g., a single incision (such as an incision in or around the umbilical area) or through a natural orifice (such as a rectum or vagina, for performing natural orifice transluminal endoscopic surgery (or NOTES), hereinafter referred to as an "opening") of the patient is depicted in FIG. 2A and FIG. 2B. The surgical device may then be anchored so as to position the surgical device 200 in the opening. The surgical device 200 may comprise a port assembly 210 and an instrument arm assembly 230. The surgical device 200 may also comprise other elements, such as one or more other instrument arm assemblies, one or more image capturing assemblies, one or more assistant arm assemblies, etc.

Figure 1B:
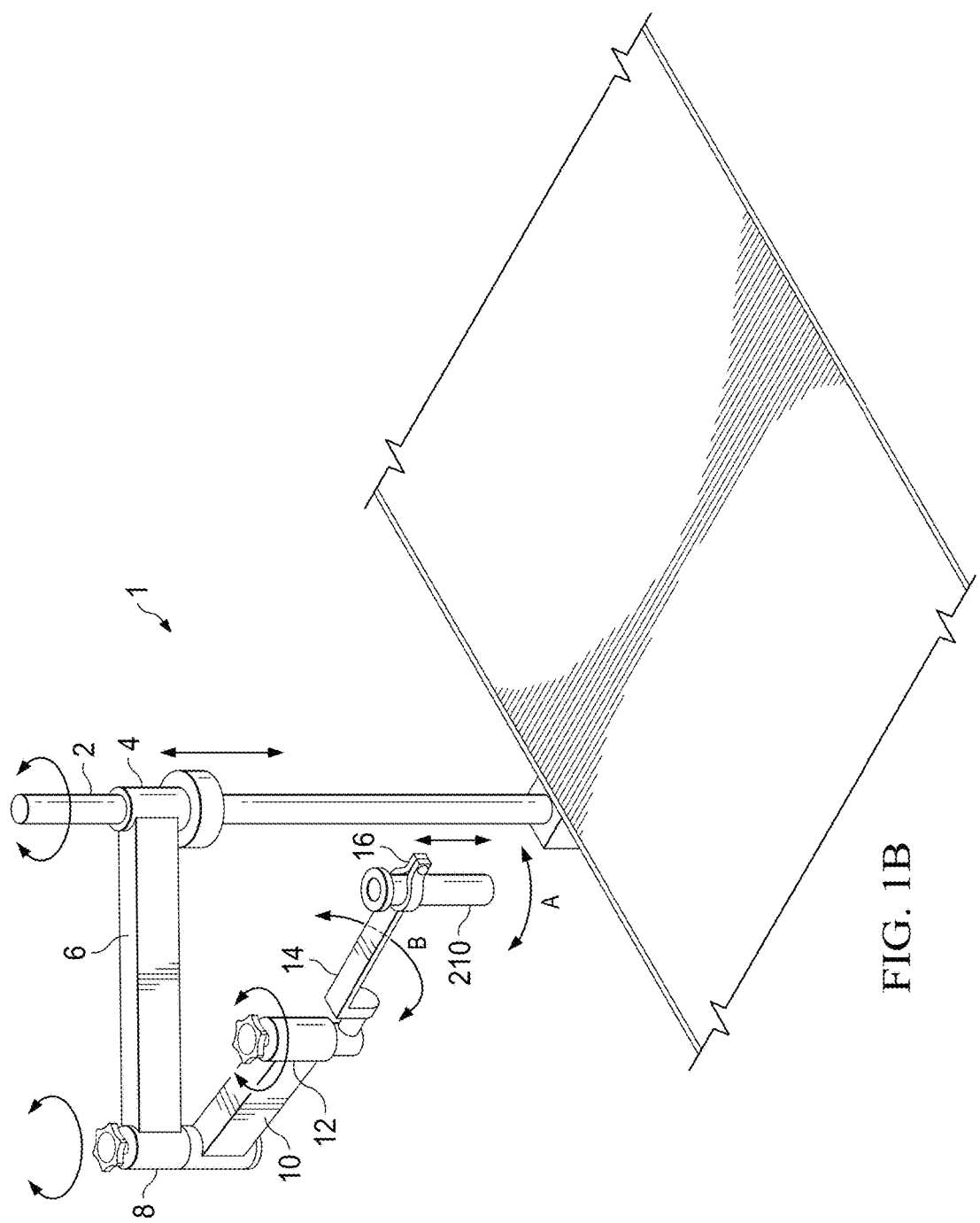
FIG. 1B is another illustration of a perspective view of an example embodiment of an external anchor attached to an example embodiment of a port assembly.
Figure 10A:
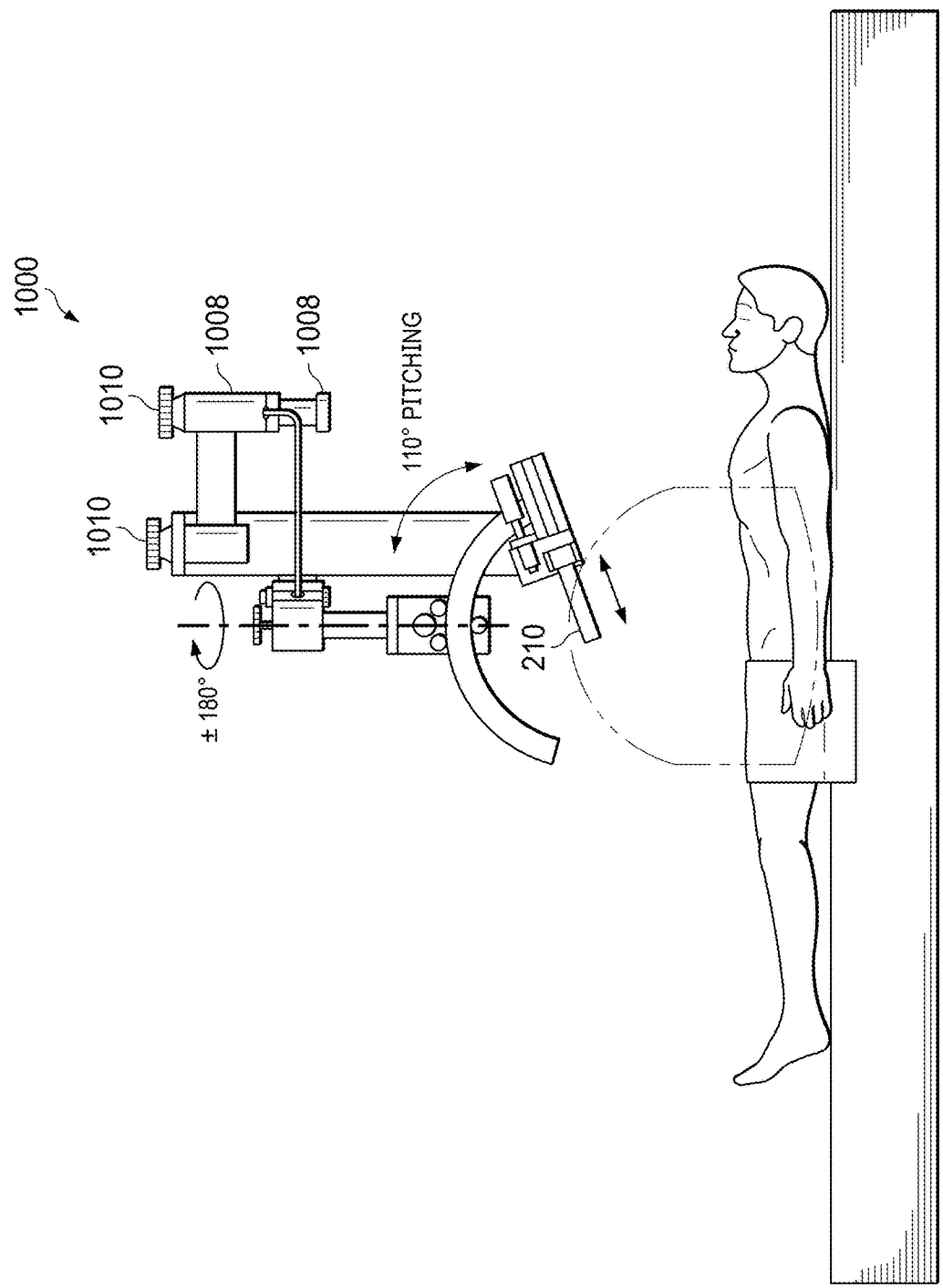
FIG. 10A is an illustration of a perspective view of an example embodiment of an external anchor.
Figure 10B:
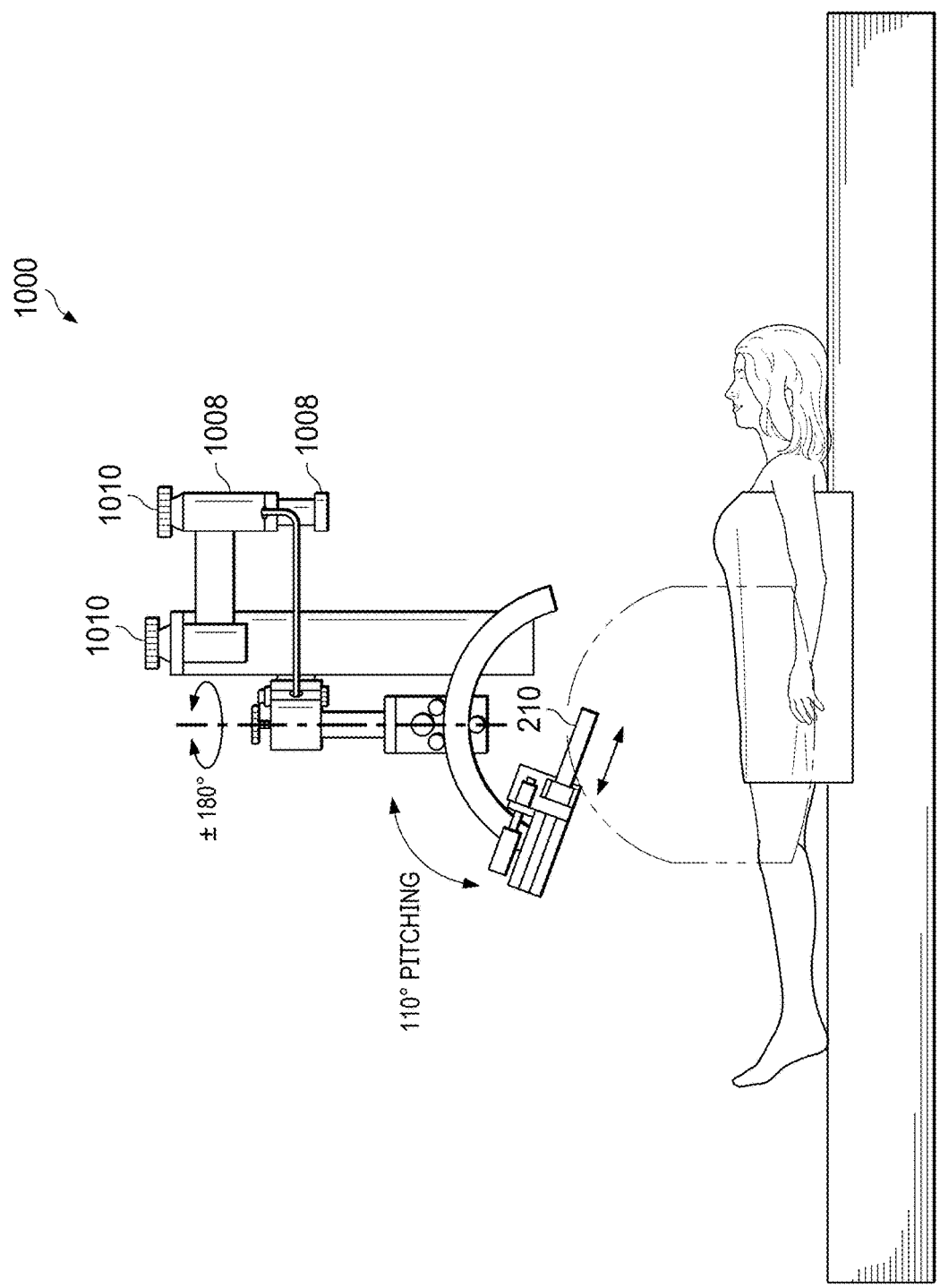
FIG. 10B is an illustration of a perspective view of another example embodiment of an external anchor.

As illustrated in FIG. 1A and FIG. 1B, the surgical device 200 may be provided with an external anchor 1 attachable to the port assembly 210. The external anchor 1 may comprise a configurable assembly of segments 2, 6, 10, and 14 in communication with one another via joints or connecting portions 4, 8, and 12, and external anchor connector 16. The external anchor 1 may be operable to securely fix the position and/or orientation (hereinafter "position") of the port assembly 210 in or about the single opening of the patient, and may also be operable to provide sufficient anchoring and/or reactive forces to stabilize against forces desired and/or necessary to be applied by at least one or more elements of the surgical device 200, including the instrument arm assembly 230, during a surgical action or procedure. The external anchor 1, which may also be in the form of the controllable swivel assembly 1000 illustrated in FIG. 10A and FIG. 10B, may be operable to cooperate with the port assembly 210 to provide one or more in vitro degrees of freedom. For example, the external anchor 1 may be configurable to provide 3 in vitro degrees of freedom. In example embodiments, the one or more in vitro degrees of freedom may include a torsional movement, pivotal movement, telescopic movement, and/or other movements of the port assembly 210 relative to the external anchor 1. For example, a torsional movement of the port assembly 210, as illustrated by arrow A in FIG. 1B, may allow one or more attached instruments, including an instrument arm assembly 230, to re-position during a surgical procedure (i.e. after set up or installation) so as to access other parts, areas, and/or all quadrants of the abdominal cavity of the patient. As another example, a pivotal movement of the port assembly 210, as illustrated by arrow B in FIG. 1B, may allow the port assembly 210 to be positioned in one of a plurality of angles with respect to opening of the patient, and may also allow attached instruments, including the instrument arm assembly 230, to re-position during a surgical procedure (i.e. after set up or installation) so as to access distal areas of the abdominal cavity of the patient. The other joint portions of the external anchor 1 may also be operable to cooperate and/or assist in desired movements of the port assembly 210. The external anchor 1 may be anchored to one or more stationary or fixedly positioned objects, such as a side rail 300 of a surgical table/bed illustrated in FIG. 1A. FIGS. 10A and 10B illustrate other example movements that provide for additional in vitro degrees of freedom via an example embodiment of the external anchor (controllable swivel assembly) 1000. The controllable swivel assembly 1000 will be further described below in at least the section "(1) Providing the external anchor and installing the port assembly."

Figure 3A:
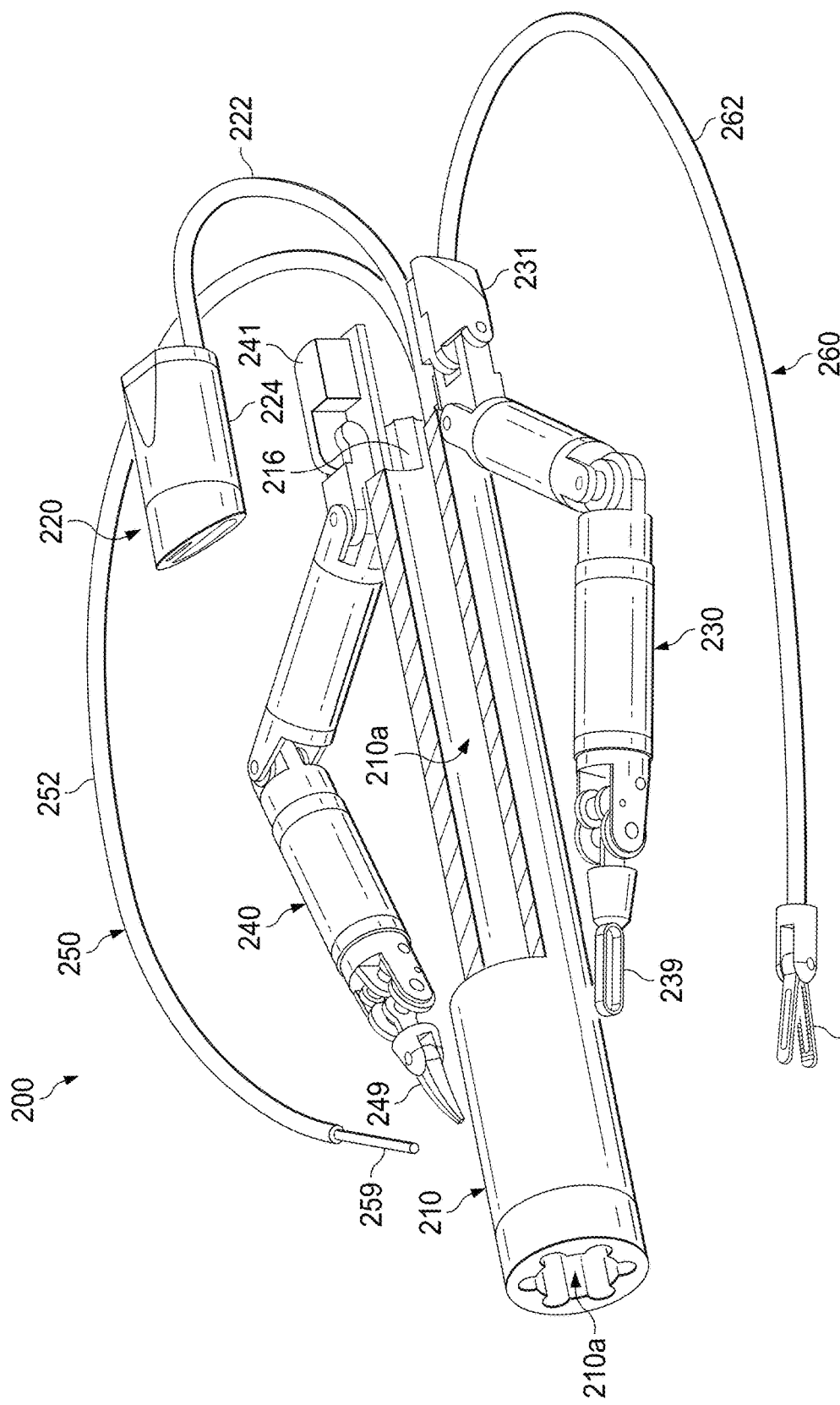
FIG. 3A is another illustration of a perspective view of another example embodiment of a surgical device configured in a reverse-directed position with one port assembly, one instrument arm assembly, and one image capturing assembly.
Figure 3B:
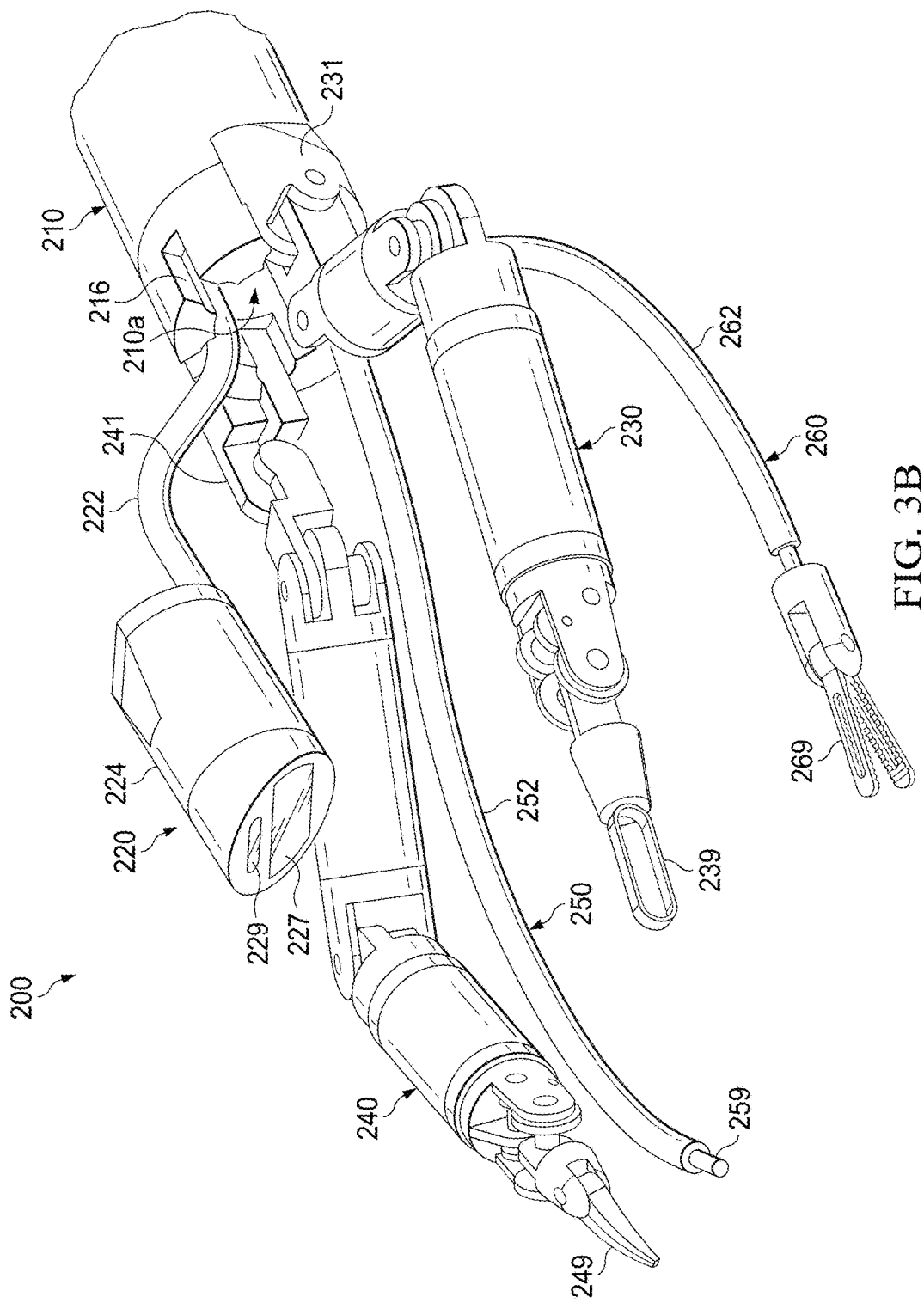
FIG. 3B is another illustration of a perspective view of another example embodiment of a surgical device configured in a forward-directed position with one port assembly, one instrument arm assembly, and one image capturing assembly.

The surgical device 200 may further comprise one or more additional instrument arm assemblies, such as a second instrument arm assembly 240 illustrated in FIGS. 3A and 3B, attachable to the port assembly 210. One or more of the instrument arm assemblies, including the first instrument arm assembly 230, the second instrument arm assembly 240, a third instrument arm assembly (not shown), a fourth instrument arm assembly (not shown), etc., may be attachable or securable to the port assembly 210. Such instrument arm assemblies may be operable to access and perform one or more surgical actions in/on any and all parts, areas, and/or quadrants within a cavity of the patient. For example, surgical device 200 may be configurable to perform surgical actions in a forward direction (or "forward-directed position" or "forward position") (e.g., as illustrated in FIGS. 2B and 3B). As another example, surgical device 200 may be configurable to perform surgical actions in a reverse direction (or "reverse-directed position" or "reverse position") (e.g., as illustrated in FIGS. 2A and 3A).

The surgical device 200 may also comprise one or more image capturing assemblies, such as image capturing assembly 220. The surgical device 200 may further comprise one or more assistant arm assemblies, such as a retractor arm assembly 250, as illustrated in FIGS. 2A, 2B, 3A, and 3B. Furthermore, the surgical device 200 may comprise one or more other instrument arm assemblies, such as suction/irrigation assembly 260, illustrated in FIGS. 2A, 2B, 3A, and 3B, that can be inserted into the opening of the patient via the port assembly 210 before, during, and/or after performing a surgical action or procedure. It is to be understood in the present disclosure that the surgical device 200 may be configurable in a plurality of configurations and arrangements, including having more or less than two instrument arm assemblies (such as third, fourth, fifth, etc. instrument arm assemblies), more than one image capturing assembly (such as second, third, etc. image capturing assemblies), more or less than one assistant arm assembly (such as second, third, etc. assistant arm assemblies), and/or more or less than one other laparoscopic tool in example embodiments without departing from the teachings of the present disclosure.

The Port Assembly (e.g., Port Assembly 210)

An example embodiment of the port assembly (e.g., port assembly 210) is illustrated in FIGS. 2A, 2B, 3A, 3B, FIG. 4A, FIG. 4B, FIG. 4C, and FIG. 4D. The port assembly 210 may be configurable to be inserted in or about a single opening of the patient (such as a single incision or a natural orifice) and fixed in position by at least the external anchor (such as the external anchor 1 illustrated in FIGS. 1A and 1B and the controllable swivel assembly 1000 illustrated in FIGS. 10A and 10B).

Figure 4A:
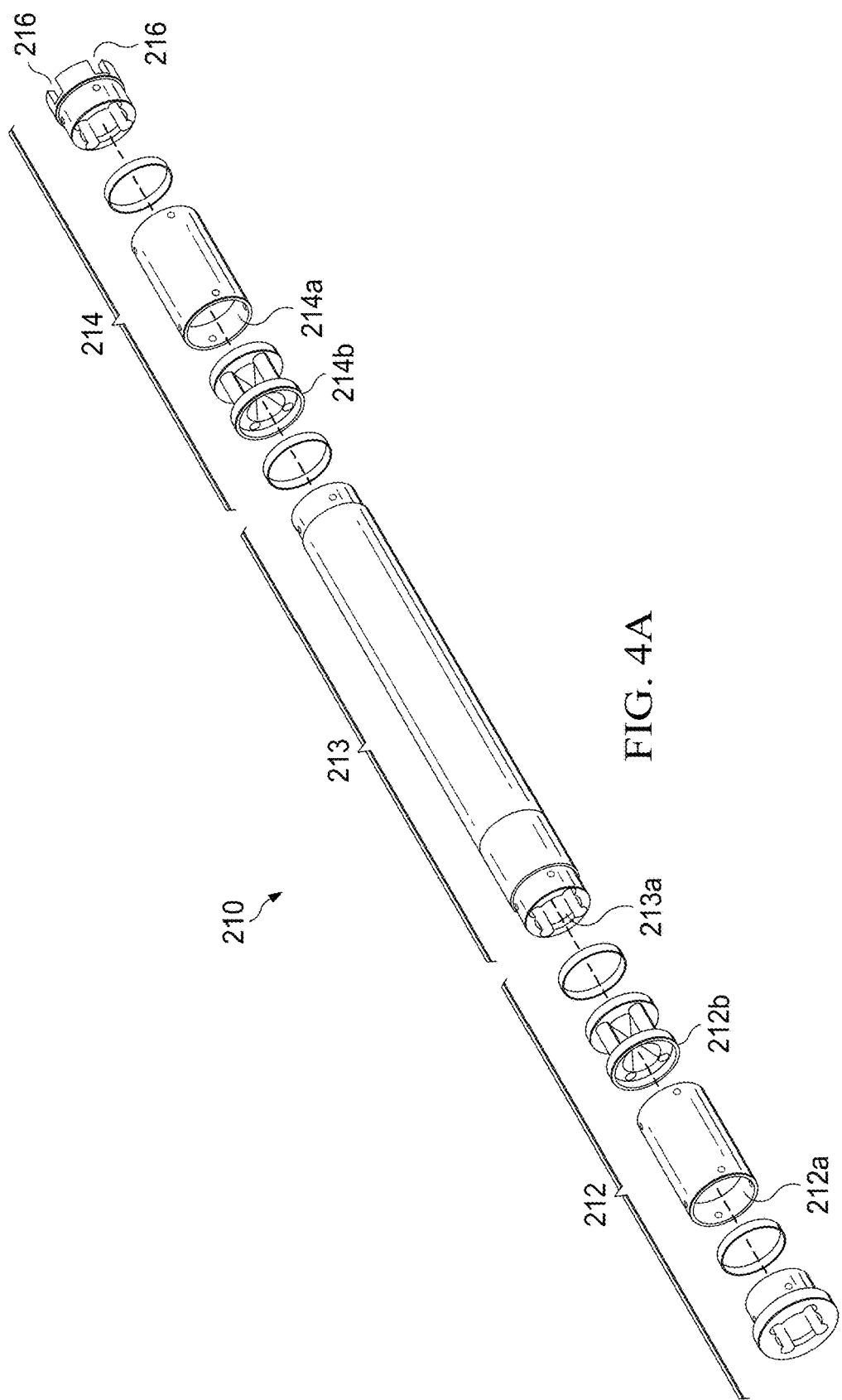
FIG. 4A is an illustration of a perspective exploded view of an example embodiment of a port assembly.

The port assembly 210 may be an elongated structure having a central access channel 210a formed through the port assembly 210. The central access channel 210a may be for use in inserting and removing instruments, such as one or more instrument arm assemblies 230, 240, one or more image capturing assemblies 220, one or more assistant arm assemblies 250, 260, etc. In an example embodiment, the port assembly 210 may include a first end section 212 and a second end section 214. The first end section 212 and second end section 214 may be fixably attachable to one another or formed as a unitary article. The port assembly 210 may also include a mid section 213 between the first end section 212 and the second end section 214. The first end section 212, second end section 214, and mid section 213 may be fixably attachable to one another, as illustrated in FIGS. 4A and 4B, or two or more of these sections may be formed as a unitary article. In an example embodiment, the first end section 212 may be the portion of the port assembly 210 that is secured to the external anchor 1, and the port assembly 210 may be fixed in position at an angle $\theta$ relative to the singe opening of the patient of between about 0 to +/−90 degrees. These and other elements of the port assembly 210 will now be described below and with reference to FIGS. 2A, 2B, 3A, 3B, and 4A-D.

As illustrated in at least FIGS. 4A and 4B, the port assembly 210 may comprise a first end section 212. The first end section 212 may have a first end channel 212a formed through the first end section 212. The first end channel 212a may be considered as a part of the central access channel 210a. The first end section 212 may also include a portion operable to be secured to the external anchor 1, such as a portion on an exterior portion of the first end section 212.

The first end section 212 may also include a first gate assembly 212b, as illustrated in FIGS. 4A, 4C, and 4D. The first gate assembly 212 may be configurable to control access through the first end channel 212a. For example, the first gate assembly 212b may be configurable to be in an open position, as illustrated in FIG. 4C, so as to allow access through the first end channel 212a. The first gate assembly 212b may also be configurable to be in a closed position, as illustrated in FIG. 4D, so as to prevent or restrict access through the first end channel 212a. The first gate assembly 212b may also be configurable to be in a partially closed (or partially opened) position (not shown). The first gate assembly 212b may also be configurable to transition between the closed position and the open position.

In an example embodiment, the first gate assembly 212b may be provided within the first end section 212 in such a way that, when the first gate assembly 212b is configured to be in the open position, as illustrated in FIG. 4C, the first end channel 212a is substantially or completely unobstructed by the first gate assembly 212b. The first gate assembly 212b may be configured to be in the open position when a surgeon desires to insert (or remove) an instrument into (or out of) the cavity of the patient via the first end channel 212a (and the rest of the central access channel 210a).

Similarly, the first gate assembly 212b may be provided within the first end section 212 in such a way that, when the first gate assembly 212b is configured to be in the closed position, as illustrated in FIG. 4D, the first end channel 212a is substantially or completely obstructed by the first gate assembly 212b. The first gate assembly 212b may be configured to be in the closed position when a surgeon desires to maintain an insufflation of the cavity of the patient and/or when the surgeon does not need to insert (or remove) an instrument into (or out of) the cavity of the patient via the first end channel 212a.

The first gate assembly 212b may include a first expandable portion 212b configurable to expand when the first gate assembly 212b is configured to the closed position, as illustrated in FIG. 4D. When the first gate assembly 212b is configured to the closed position, the first expandable portion 212b may be operable to substantially or completely block, among other things, a gas medium (and/or other medium) from passing through the first end channel 212a. For example, if the cavity of the patient is being insufflated using a gas, such as carbon dioxide ($CO_2$), the first gate assembly 212b (i.e., the first expandable portion 212b) may be configurable to substantially prevent the carbon dioxide gas from leaving the cavity of the patient through the first end channel 212a.

The first expandable portion 212b may include one or more first expandable members. For example, the first expandable portion 212b may include six expandable members, as illustrated in FIGS. 4C and 4D. It is to be understood that the first expandable portion 212b may include more or less than six expandable members without departing from the teachings of the present disclosure. Some or all of the first expandable members may be integrated together and/or in communication with one another, such as in a manner where some or all of the first expandable members are operable to receive pressure (i.e., gas medium) from a common or same first source 212b'. For example, when the first gate assembly 212b is configured to the closed position, the first source 212b' may be configurable to provide a positive pressure (i.e., a supply of gas) so as to cause some or all of the first expandable members to expand and block the first end channel 212a (e.g., hermetically block the first end channel 212a). Similarly, when the first gate assembly 212b is configured to the open position, the first source 212b' may be configurable to provide a negative pressure (i.e., remove gas) so as to cause one or more (or all) of the first expandable members to not expand (and/or contract) and unblock the first end channel 212a. It is to be understood that more than one first sources 212b' may provide the positive pressure and negative pressure to the one or more expandable members without departing from the teachings of the present disclosure.

It is recognized in the present disclosure that the first gate assembly 212b may also include a valve (not shown), or the like, in addition to or in replacement of the first expandable portion 212b. The valve may be configurable to perform substantially the same actions of blocking the first end channel 212a when the first gate assembly 212b is configured to the closed position and unblocking the first end channel 212a when the first gate assembly 212b is configured to the open position. The valve may be any type of valve configurable to perform the actions described above and in the present disclosure. The valve may include, but is not limited to including, a ball valve, gate valve, etc., so long as the valve is configurable to substantially block/unblock the first end channel 212a and prevent a gas medium from passing through the first end channel 212a.

The port assembly 210 may also include the second end section 214, as illustrated in at least FIGS. 4A and 4B. The second end section 214 may have a second end channel 214a formed through the second end section 214. The second end channel 214a may be substantially or completely aligned with the first end channel 212a. The second end channel 214a, as well as the first end channel 212a, may be considered as a part of the central access channel 210a in example embodiments. The second end section 214 may also include an insufflation port (not shown) for use in providing insufflation to the cavity of the patient.

The second end section 214 may also include a second gate assembly 214, as illustrated in FIGS. 4A, 4C, and 4D. The second gate assembly 214 may be configurable to control access through the second end channel 214a. For example, the second gate assembly 214b may be configurable to be in an open position, as illustrated in FIG. 4C, so as to allow access through the second end channel 214a. The second gate assembly 214b may also be configurable to be in a closed position, as illustrated in FIG. 4D, so as to prevent or restrict access through the second end channel 214a. The second gate assembly 214b may also be configurable to be in a partially closed (or partially opened) position (not shown). The second gate assembly 214b may also be configurable to transition between the closed position and the open position.

In an example embodiment, the second gate assembly 214b may be provided within the second end section 212 in such a way that, when the second gate assembly 214b is configured to be in the open position, as illustrated in FIG. 4C, the second end channel 214a is substantially or completely unobstructed by the second gate assembly 214b. The second gate assembly 214b may be configured to be in the open position when a surgeon desires to insert (or remove) an instrument into (or out of) the cavity of the patient via the second end channel 214a (and the rest of the central access channel 210a).

Similarly, the second gate assembly 214b may be provided within the second end section 214 in such a way that, when the second gate assembly 214b is configured to be in the closed position, as illustrated in FIG. 4D, the second end channel 214a is substantially or completely obstructed by the second gate assembly 214b. The second gate assembly 214b may be configured to be in the closed position when a surgeon desires to maintain an insufflation of the cavity of the patient and/or when the surgeon does not need to insert (or remove) an instrument into (or out of) the cavity of the patient via the second end channel 214a.

The second gate assembly 214b may include a second expandable portion 214b configurable to expand when the second gate assembly 214b is configured to the closed position, as illustrated in FIG. 4D. When the second gate assembly 214b is configured to the closed position, the second expandable portion 214b may be operable to substantially or completely block, among other things, a gas medium (and/or other medium) from passing through the second end channel 214a. For example, if the cavity of the patient is being insufflated using a gas, such as carbon dioxide ($CO_2$), the second gate assembly 214b (i.e., the second expandable portion 214b) may be configurable to substantially prevent the carbon dioxide gas from leaving the cavity of the patient through the second end channel 214a.

The second expandable portion 214b may include one or more second expandable members. For example, the second expandable portion may include six expandable members, as illustrated in FIGS. 4C and 4D. It is to be understood that the second expandable portion 214b may include more or less than six expandable members without departing from the teachings of the present disclosure. Some or all of the second expandable members may be integrated together and/or in communication with one another, such as in a manner where some or all of the second expandable members are operable to receive pressure (i.e., gas medium) from a common or same second source 214b'. For example, when the second gate assembly 214b is configured to the closed position, the second source 214b' may be configurable to provide a positive pressure (i.e., a supply of gas) so as to cause some or all of the second expandable members to expand and block the second end channel 214a (e.g., hermetically block the second end channel 214a). Similarly, when the second gate assembly 214b is configured to the open position, the second source 214b' may be configurable to provide a negative pressure (i.e., remove gas) so as to cause some or all of the second expandable members to not expand (and/or contract) and unblock the second end channel 214a. It is to be understood that more than one second sources 214b' may provide the positive pressure and negative pressure to the one or more expandable members without departing from the teachings of the present disclosure. It is also to be understood in the present disclosure that one or more of the first sources 212b' and one or more of the second sources 214b' may be the same or different sources.

It is recognized in the present disclosure that the second gate assembly 214b may also include a valve (not shown), or the like, in addition to or in replacement of the second expandable portion 214b. The valve may be configurable to perform substantially the same actions of blocking the second end channel 214a when the second gate assembly 214b is configured to the closed position and unblocking the second end channel 214a when the second gate assembly 214b is configured to the open position. The valve may be any type of valve configurable to perform the actions described above and in the present disclosure. The valve may include, but is not limited to including, a ball valve, gate valve, etc., so long as the valve is configurable to substantially block/unblock the second end channel 214a and prevent a gas medium from passing through the second end channel 214a.

The second end section 214 may also include one or more anchor ports 216, as illustrated in FIGS. 4A and 4B. Each of the anchor ports 216 may be operable to enable an instrument arm assembly 230 or 240, image capturing assembly 220, and/or assistant arm assemblies 250 or 260 to be secured to and unsecured from the port assembly 210. Each of the anchor ports 216 may be formed in any one or more of a plurality of shapes, holes, slots, indentations, protrusions, hooks, fasteners, magnets, buckles, or the like, including those described above and in the present disclosure. For example, as illustrated in FIGS. 4A and 4B, one or more of the anchor ports 216 may include one or more slots, or the like, operable to allow a shoulder section 231 of an instrument arm assembly 230 or 240 to be inserted into and attached.

In example embodiments, the port assembly 210 may also include the mid section 213, as illustrated in at least FIGS. 4A and 4B. The mid section 213 may have a mid section channel 213a formed through the mid section 213. The mid section channel 213a may be substantially or completely aligned with the first end channel 212a and/or the second end channel 214a. In this regard, the mid section channel 213a, as well as the first end channel 212a and/or the second end channel 214a, may be considered as a part of the central access channel 210a in example embodiments. The mid section 213 may also include an insufflation port (not shown) in addition to or in replacement of the insufflation port (not shown) of the second end section 214. In some example embodiments, the mid section 213 may also include a mid section gate assembly (not shown) similar to that of the first gate assembly 212 and second gate assembly 214 described above and in the present disclosure.

In example embodiments, the mid section channel 213a may be operable to cooperate with the first gate assembly 212b and the second gate assembly 214b to function as or like an isolation chamber for instruments, such as the instrument arm assembly 230 or 240, image capturing assembly 220, assistant arm assembly 250 or 260, etc. For example, when an instrument, such as the instrument arm assembly 230, needs to be inserted into the cavity of the patient via the port assembly 210 (or central access channel 210a) and an insufflation of the cavity of the patient needs to be maintained, the first gate assembly 212b may be configured to the open position to allow the instrument to be inserted into the mid section channel 213a. After the instrument (or most of it) passes through the first gate assembly 212b, the first gate assembly 212b may be configured to the closed position. The second gate assembly 214b may then be configured to the open position to allow the instrument to be further inserted through the port assembly 210. After the instrument (or most of it) passes through the second gate assembly 214b, the second gate assembly 214b may be configured to the closed position.

In respect to the central access channel 210a, the central access channel 210a may include or be formed by the first end channel 212a, the second end channel 214a, and/or the mid section channel 213a. The central access channel 210a may be operable to provide an access port (i.e. a passageway or channel) to allow an insertion (or removal) of one or more instruments, such as one or more instrument arm assemblies 230 or 240, one or more image capturing assemblies 220, one or more assistant arm assemblies 250 or 260, etc.

In an example embodiment, the first end section 212, the second end 214, and/or the mid section 213 may be substantially cylindrical in shape. The first end section 212, the second end section 214, and/or the mid section 213 may also be formed in any one of a plurality of other shapes, sizes, and/or dimensions without departing from the teachings of the present disclosure.

In example embodiments, an outer diameter of the first end section 212, the second end 214, and/or the mid section 213 may be between about 28 to 35 mm and an inner diameter (unblocked) of the first end section 212, the second end 214, and/or the mid section 213 may be between about 16 to 21 mm. In an example embodiment, the outer diameter of the first end section 212, the second end 214, and/or the mid section 213 may be about 33 mm and the inner diameter (unblocked) of the first end section 212, the second end 214, and/or the mid section 213 may be about 19 mm. The length of the first end section 212 may be between about 80 to 100 mm, the length of the second end section 214 may be between about 80 to 200 mm, and the length of the mid section 213 may be between about 60 to 80 mm. The overall length of the port assembly 210 may be between about 320 to 380 mm. It is to be understood in the present disclosure that the above dimensions are merely an illustration of example embodiments, and as such the dimensions may be smaller or larger than those recited above without departing from the teachings of the present disclosure.

The port assembly 210, including the first end section 212, the second end section 214, the mid section 213, and/or the anchor ports 216, may be formed using any one or more of a plurality of materials, such as surgical-grade metals, high-strength aluminum alloys, stainless steel (such as 304/ 304L, 316/316L, and 420), pure titanium, titanium alloys (such as Ti6Al4V, NiTi), and cobalt-chromium alloys. The first gate assembly 212b and the second gate assembly 214b may be formed using any one or more of a plurality of materials, such as bio-compatible materials (such as silicone rubber and polyurethane). It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Image Capturing Assembly (e.g., Image Capturing Assembly 220)

In an example embodiment, the surgical device 200 may comprise one or more image capturing assemblies (e.g., image capturing assembly 220) configurable to be inserted into and attach to the port assembly 210. One or more of the image capturing assemblies 220 may comprise at an image capturing body 224, a multi-curvable body 222, and an anchoring portion 220a.

Figure 6A:
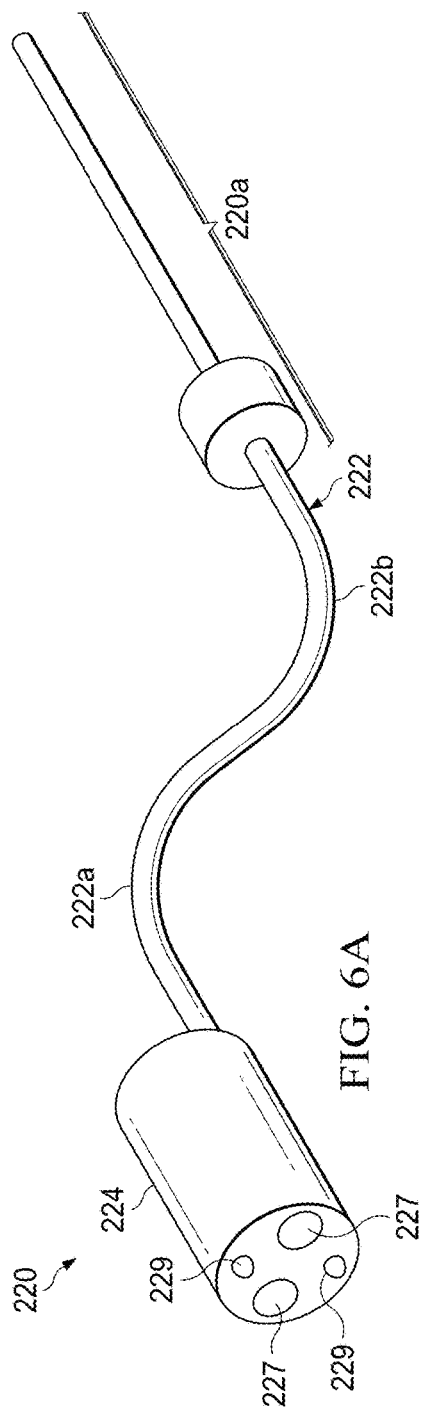
FIG. 6A is an illustration of a perspective view of an example embodiment of an image capturing assembly.
Figure 9B:
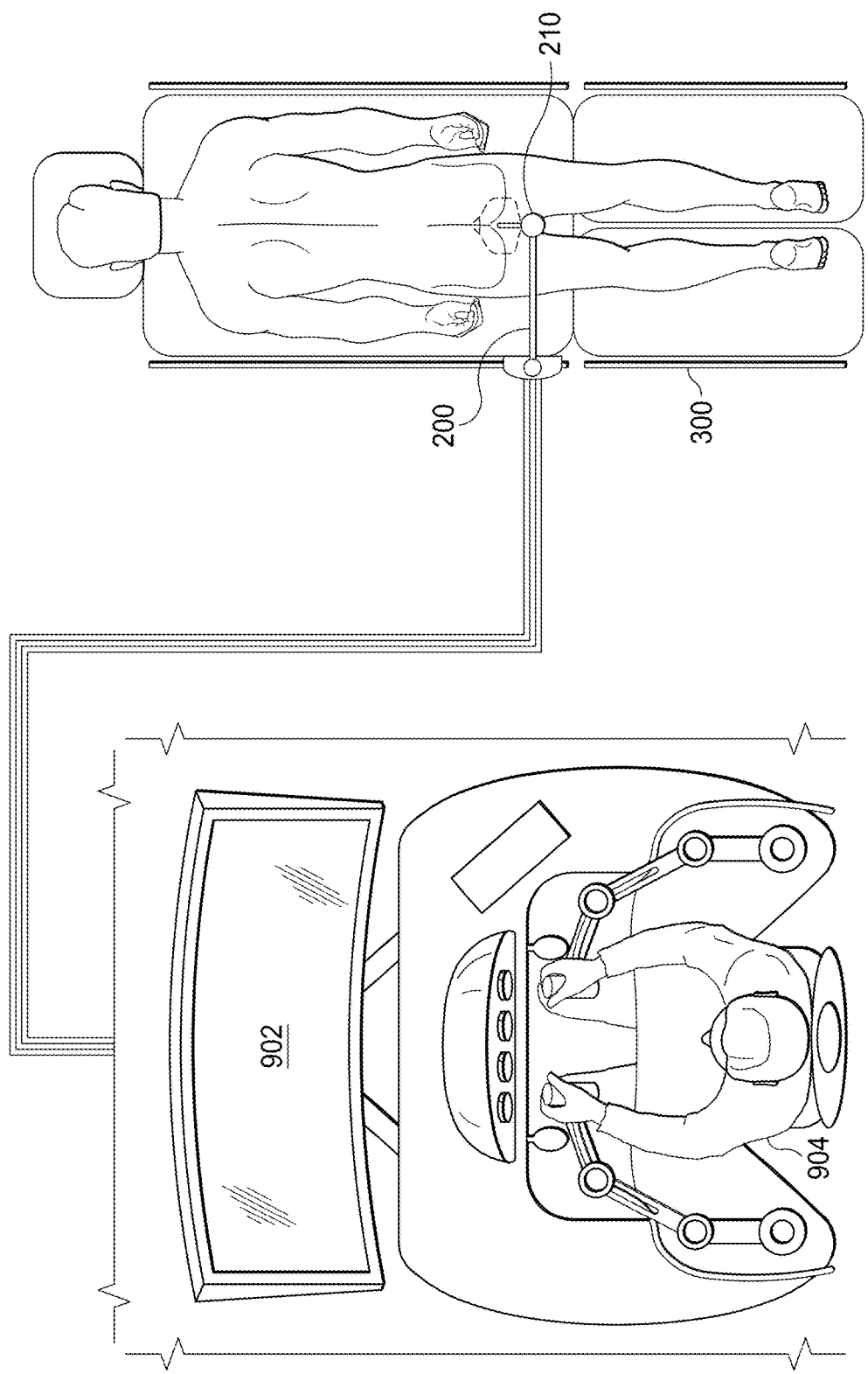
FIG. 9B is an illustration of a perspective view of another example embodiment of a surgical device system.

As illustrated in FIG. 6A, the image capturing body 224 may include one or more cameras 227. Each camera 227 may include a standard and/or high definition 2-dimensional (2D) and/or 3-dimensional (3D) camera operable to capture imaging, such as 2D and/or stereoscopic and/or autostereoscopic 3D imaging, including images, video, and/or audio, and provide in real-time via wired and/or wireless communication the captured imaging, including images, video, and/or audio, to the computing device (or controller or system) of one or more nearby and/or remotely located surgical teams 904, as described above and in the present disclosure. The computing device (or controller or system) may comprise one or more processors, one or more computer-human interfaces, one or more graphical displays (such as computer screens, television screens, portable devices, wearable devices such as glasses, etc.), and/or other devices and/or systems, an example of which is illustrated in FIGS. 9A and 9B. The one or more nearby and/or remotely located surgical teams 904 may be operable to view, hear, sense, analyze, and control (such as pan, zoom, process, adapt, mark, change resolution, etc.) the imaging displayed or represented on one or more standard and/or high definition 2D and/or 3D graphical displays 902, such as shown in the illustration of FIGS. 9A and 9B, and/or portable and/or wearable devices adapted to receive 2D and/or 3D imaging (not shown). The image capturing body 224 may also comprise one or more illumination sources 229, such as an LED, or the like, operable to illuminate or sense at least one or more parts, sections, and/or quadrants of the cavity of the patient, including instruments provided in the cavity of the patient. The image capturing body 224 may further comprise one or more internal temperature control assemblies operable to control (such as reduce) the temperature of one or more components of the image capturing body 224.

As illustrated in the example embodiment of FIG. 6A, one or more of the image capturing assemblies 220 may comprise a multi-curvable body 222 attached to the image capturing body 224. The multi-curvable body 222 may be any elongated multi-curvable, multi-bendable, multi-articulable, and/or snake-like (hereinafter "multi-curvable") body that can be controlled/configured by the surgical team (such as via the computing device/controller) to, among other things, straighten and/or curve (and hold such a straightness and/or curvature) at one or more of a plurality of locations along the multi-curvable body 222, curve (and hold such a curvature) in one or more of a plurality of curvatures, and/or straighten and/or curve (and hold such a straightness and/or curvature) in one or more of a plurality of directions. For example, as illustrated in FIG. 8H, the multi-curvable body 222 may be controllable/configurable by the surgical team (such as via the computing device/controller) to curve at two different locations 222a and 222b along the multi-curvable body 222, and each of the curves may include any curvature and in any direction. It is to be understood that the multi-curvable body 222 may be configurable to curve in more or less than two locations along the multi-curvable body 222 without departing from the teachings of the present disclosure. It is also to be understood that, when the multi-curvable body 222 is configured to curve at any location along the multi-curvable body 222, the curve may be held and/or released (or configured to uncurve, curve less, or straighten) by the surgical team (such as via the computing device/controller).

The multi-curvable body 222 may be formed in any one or more ways known in the art including. For example, the multi-curvable body 222 may include a plurality of segments, each segment linked to an adjacent segment in such a way that the segment may be controlled/configured to be pivotally positioned in a plurality of positions relative to the adjacent segment. As another example, the multi-curvable body 222 may include a plurality of wires, cables, or the like, distributed throughout the multi-curvable body 222 in such a way that a pulling/releasing, shortening/lengthening, tightening/loosening, etc. of one or a combination of cables enables the above-mentioned curving of one or more locations of the multi-curvable body 222 in one or more curvatures and in one or more directions. As another example, the multi-curvable body 222 may include a plurality of springs, gears, motors, etc. for achieving the above-mentioned curving. It is to be understood in the present disclosure that the multi-curvable body 222 may also include a combination of one or more of the above-mentioned approaches.

One or more internal temperature control assemblies (not shown) may be provided for each image capturing assembly 220. Each internal temperature control assembly may be operable to control (such as reduce) the temperature and/or heat emission of the aforementioned camera(s) 227, illumination source(s) 229, and/or multi-curvable body 222. In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well as any solids (if used), may be provided through an interior of the image capturing assembly 220 without increasing dimensions (such as diameter) of the image capturing assembly 220 and/or affecting the controllability/configurability of the multi-curvable body 222.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the cavity of the patient during a surgical procedure. When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the image capturing assembly 220. In example embodiments, the internal temperature control assembly may utilize a combination of gases, liquids, solids, and/or the like without departing from the teachings of the present disclosure.

The image capturing assembly 220 may be secured to the port assembly 210 in one or more of a plurality of ways, including those described above and in the present disclosure for the instrument arm assemblies 230 or 240 and/or the assistant arm assemblies 250 or 260. For example, the image capturing assembly 220 may also comprise an anchoring portion 220a (e.g., similar to the securing portion 231a of the instrument arm assembly 220) operable to attach (or secure) the image capturing assembly 220 to one or more anchor ports 216 of the port assembly 210.

In an example embodiment, the image capturing body 224 and the multi-curvable body 222 may each be substantially cylindrical in shape. The image capturing body 224 and the multi-curvable body 222 may also be formed in any one of a plurality of other shapes, sizes, and/or dimensions without departing from the teachings of the present disclosure.

In an example embodiment, the length of the multi-curvable body 222 may be between about 50 to 150 mm. In example embodiments, a length of multi-curvable body 222 may also be adjustable by the surgical team 904 before, during, and/or after insertion of the camera arm assembly into the cavity of the patient. The outer diameter of the multi-curvable body 222 may be between about 5 to 7 mm. It is to be understood in the present disclosure that the above dimensions are merely an illustration of example embodiments, and as such the dimensions may be smaller or larger than those recited above without departing from the teachings of the present disclosure.

The multi-curvable body 222 may be formed using any one or more of a plurality of materials, such as stainless steel, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

Figure 6B:
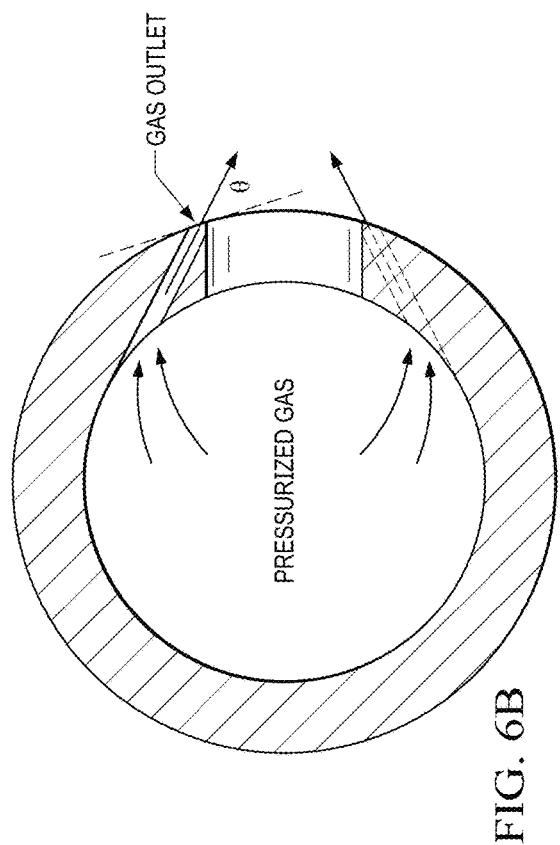
FIG. 6B is an illustration of a cross sectional view of another example embodiment of an image capturing assembly having an internal temperature control assembly.

As illustrated in FIG. 6B and FIG. 6C, the image capturing assembly 220 may further comprise a gas shield 228 located nearby one or more lenses of the camera 227. The image capturing assembly 220 may further comprise a gas shield 228 located nearby one or more of the illumination sources 229 and/or any other sensors (such as temperature sensors, pressure sensors, humidity sensors, etc.) provided by the image capturing assembly 220. The gas shield 228 may comprise one or more openings or the like, one or more external gas sources 228, and one or more tubes, channels, or the like, between the one or more external gas sources and the one or more openings of the gas shield 228. In operation, the gas shield 228 may be operable to provide pressurized gases (and/or liquids), such as carbon dioxide, oxygen, other gases or liquids, or combinations thereof, via the one or more openings of the gas shield 228 to an area in front of the camera 227 (as well as in front of the illumination sources 229 and/or other sensors).

Figure 6D:
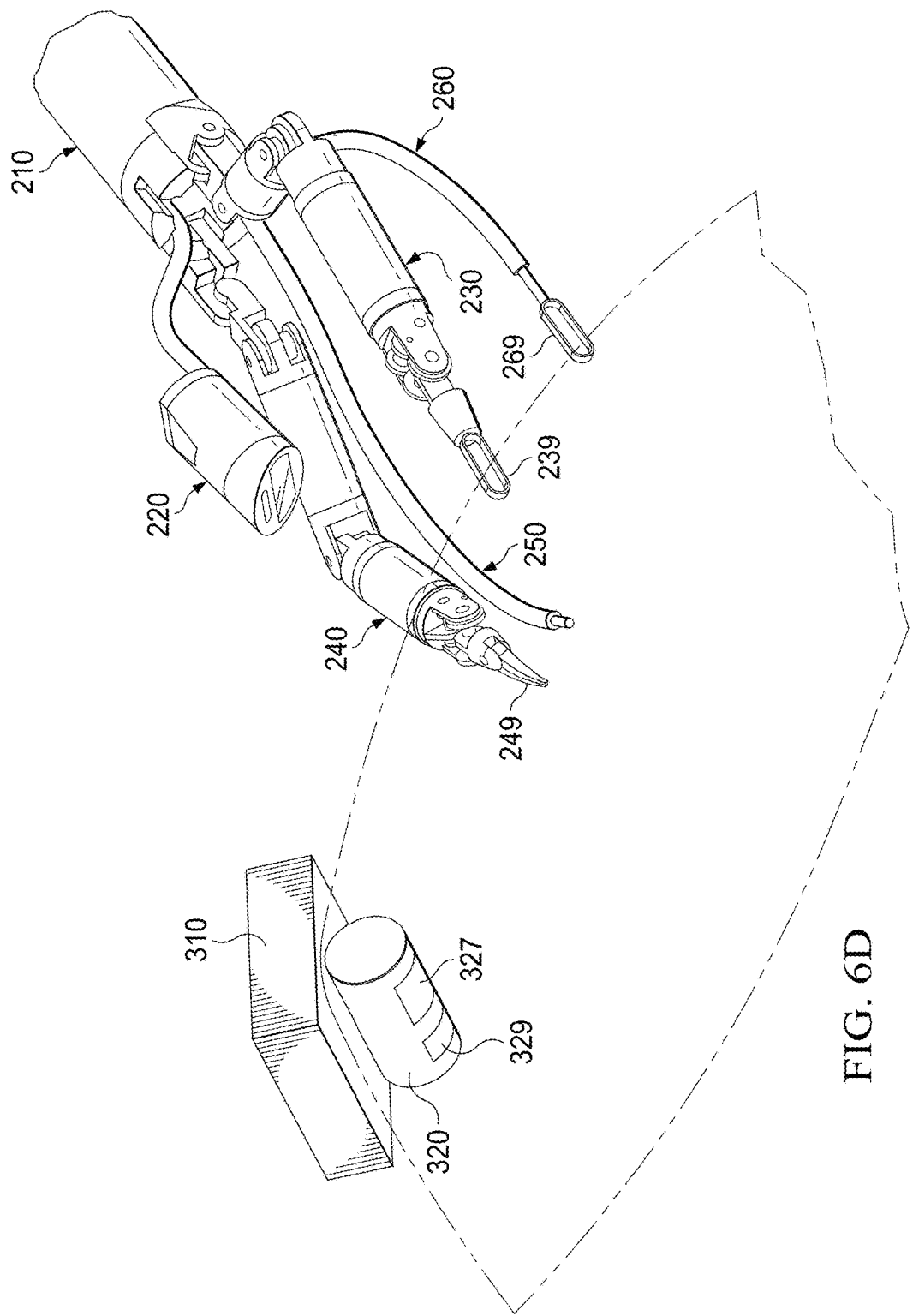
FIG. 6D is an illustration of a perspective view of the system in operation in a cavity of a patient, including a second image capturing assembly.
Figure 7:
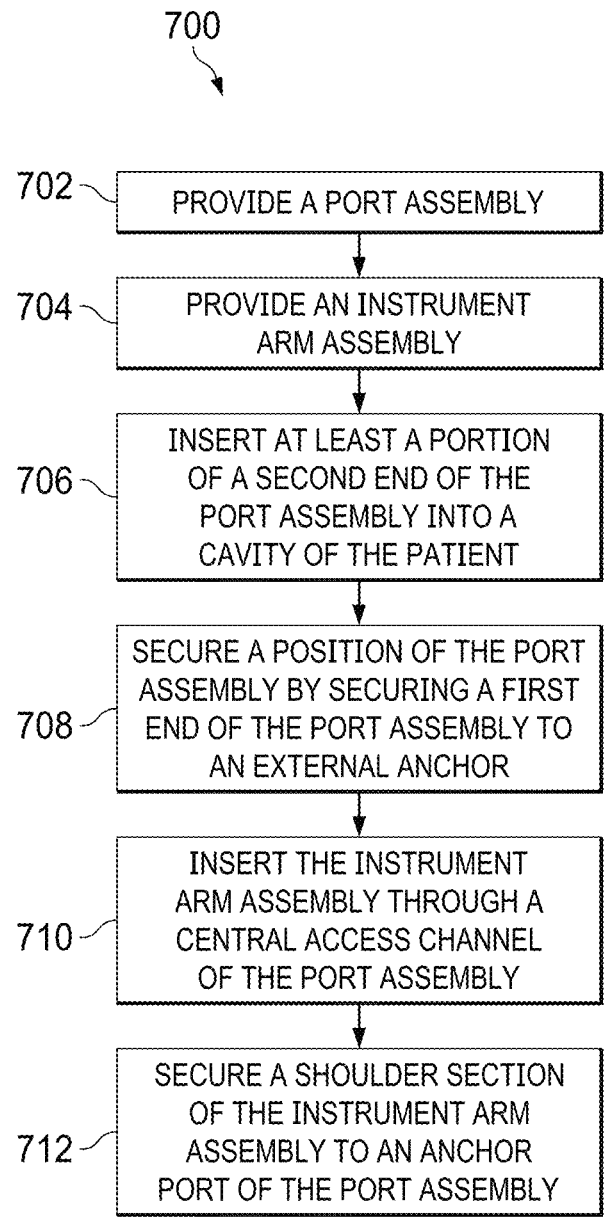
FIG. 7 is a flow diagram of an exemplary method for configuring a surgical device.

The overall system may also include one or more separate image capturing assemblies, such as the separate image capturing assembly 320 illustrated in FIG. 6D. The separate image capturing assembly 320 may be magnetically anchored by a magnetic anchor 310 to an internal wall of the cavity of the patient, such as via a permanent magnet, electromagnet, or the like. In some example embodiments, the magnetic anchor 310 may also be secured/held in position via an external anchor (not shown). The separate image capturing assembly 320 may include one or more cameras 327, and may also include one or more illumination sources 329.

The separate image capturing assembly 320 may be operable to provide one or more of a variety of views, including, but not limited to, a normal view, zoomed view, wide-angled view, and/or panoramic view of the cavity of the patient. The separate image capturing assembly 320 may be positioned in such a way as to provide the surgical team 904 with an unobstructed view of areas of interest within the cavity of the patient. In respect to positioning and securing the separate image capturing assembly 320 in place, as illustrated in FIG. 6D, the separate image capturing assembly 320 may be inserted through the central access channel 210a of the port assembly 210 and to the desired location of the interior wall of the cavity of the patient in one or more of a plurality of ways, including using a surgical tool (not shown), attaching the separate image capturing assembly 320 to a multi-curvable body (not shown) similar to that of the image capturing assembly 220 (as illustrated in FIGS. 2A, 2B, 3A, 3B, and 6D), etc.

The Instrument Arm Assembly (e.g., Instrument Arm Assembly 230, 240)

In an example embodiment, the surgical device 200 may comprise one or more instrument arm assemblies (e.g., first instrument arm assembly 230, second instrument arm assembly 240, third instrument arm assembly (not shown), fourth instrument arm assembly (not shown), etc.), each configurable to attach to the port assembly 210.

Figure 5C:
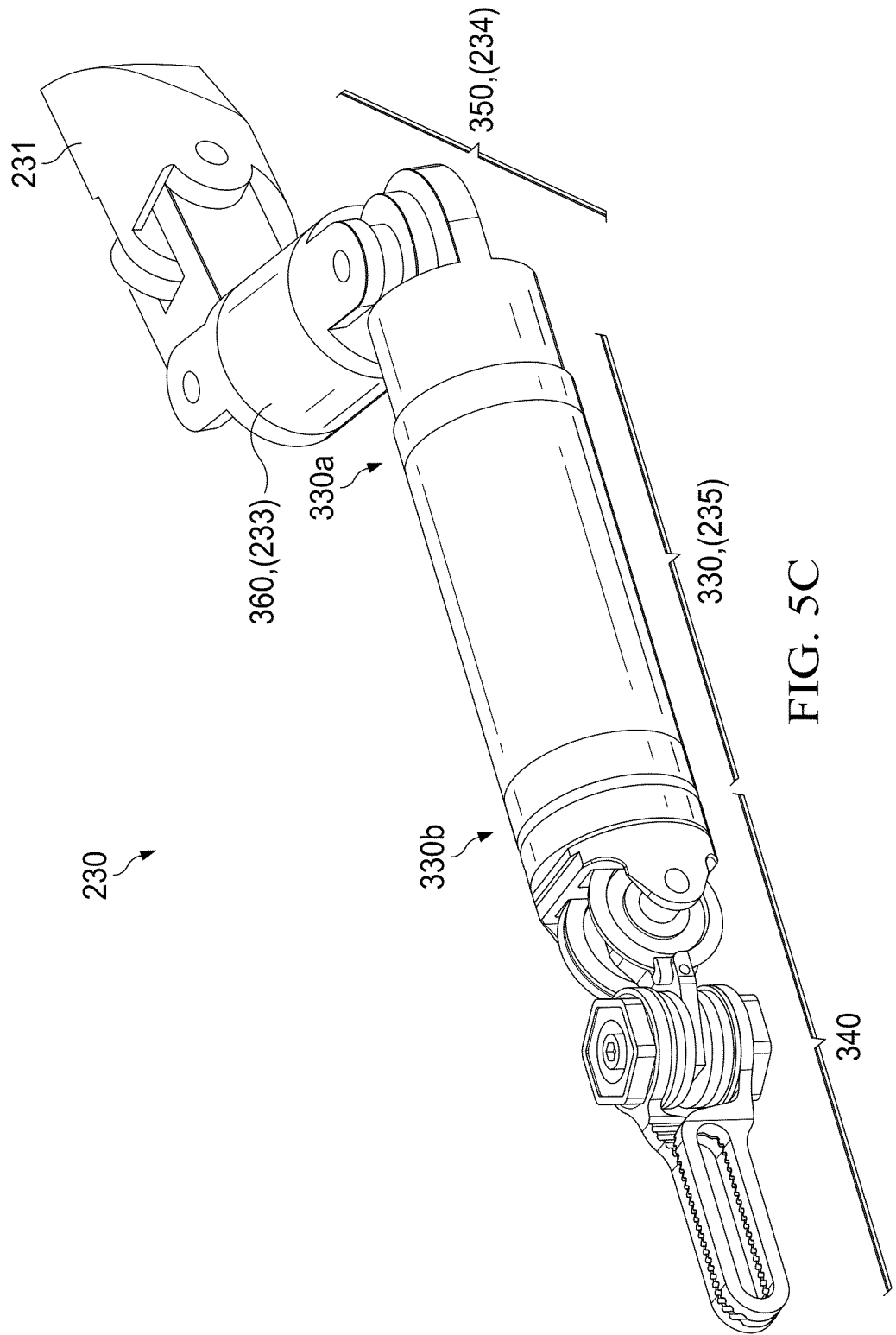
FIG. 5C is an illustration of a perspective view of an example embodiment of an instrument arm assembly.
Figure 5L:
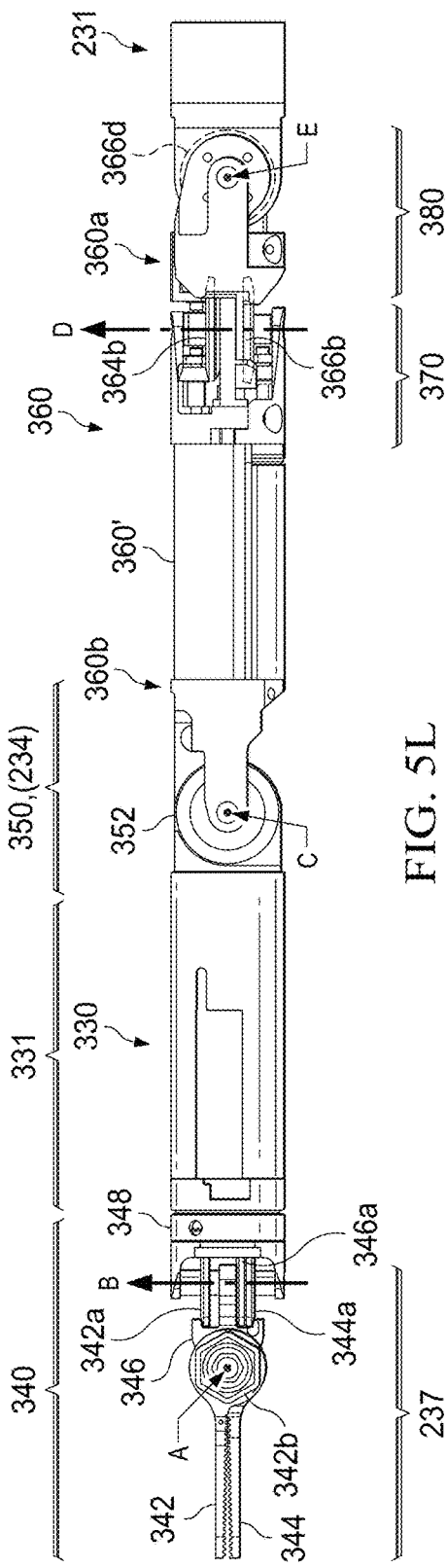
FIG. 5L is an illustration of a side view of an example embodiment of an instrument arm assembly.
Figure 5M:
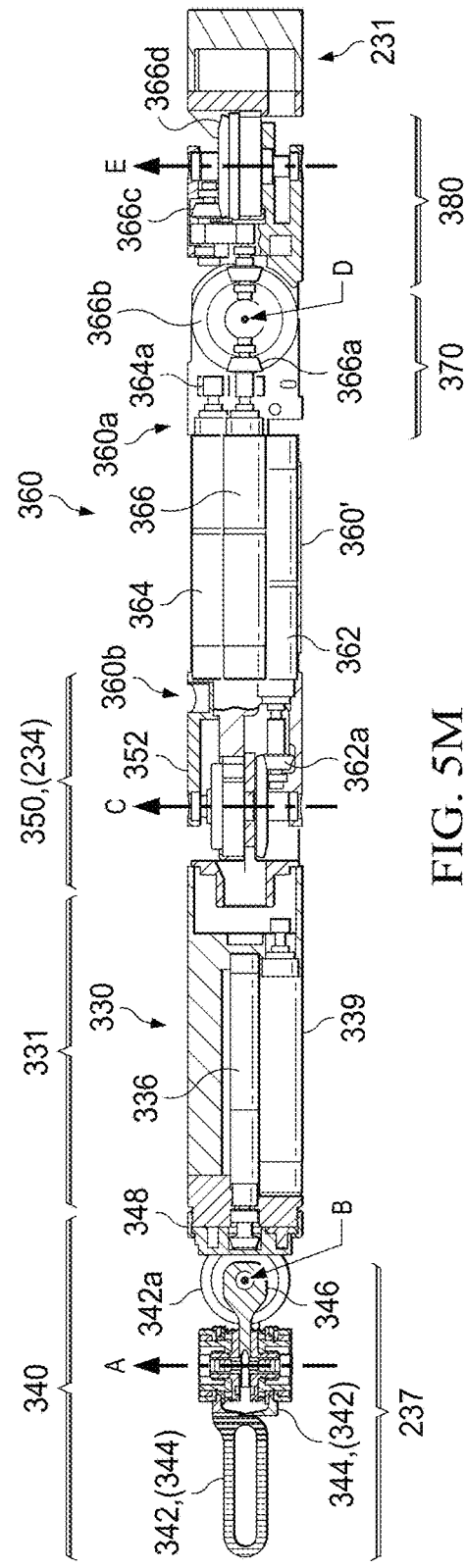
FIG. 5M is an illustration of a side cross-sectional view of an example embodiment of an instrument arm assembly.

One or more of the instrument arm assemblies (such as 230, 240) may comprise a configurable serial (or linear) arrangement of a plurality of instrument arm segments (or arm assemblies, such as a first arm assembly 330, second arm assembly 360, and shoulder assembly 231 illustrated in at least FIG. 5C) and joint portions (such as a first arm assembly joint portion 350, first shoulder joint portion 370, and second shoulder joint portion 380 illustrated in at least FIG. 5L and FIG. 5M), and at least one end instrument (or end effector) 239, 342, 344 integrated into and/or connected to one or more of the instrument arm segments and/or joint portions. The end effector 239, 342, 344 may be any instrument suitable for use in surgical procedures, such as a cutting and/or gripping instrument. One or more of the instrument arm assemblies (such as 230, 240) may also comprise one or more illumination sources (not shown), such as an LED, or the like, operable to illuminate one or more parts of the end effector 239, 342, 344, instrument arm assemblies, and/or parts, sections, and/or quadrants of the abdominal cavity of the patient.

One or more of the instrument arm assemblies (such as 230, 240) may also comprise one or more integrated motors (e.g., integrated motors 332, 334, 336, 339 illustrated in at least FIG. 5E, FIG. 5G, FIG. 5J, and FIG. 5K and integrated motors 362, 364, and 366 illustrated in at least Figure M, FIG. 5N, and FIG. 5O) operable to provide at least one degree of freedom for the instrument arm assembly. Each integrated motor (e.g., integrated motors 332, 334, 336, 339 illustrated in at least FIGS. 5E, 5G, 5J, and 5K and integrated motors 362, 364, and 366 illustrated in at least FIG. 5M-O) may be fully and independently functioning motors that are housed entirely (with the exception of, for example, power and/or control cables, which may be fed via the port assembly) in an instrument arm segment (or arm assembly, such as the first arm assembly 330, second arm assembly 360, and shoulder assembly 231), such as housing 330' and 360'. One or more of the instrument arm assemblies may also include an integrated haptic and/or force feedback subsystem (not shown) in communication with one or more of the integrated motors and/or other sensors and/or instruments operable to provide to the surgical team (such as via computing device/controller) with one or more of a plurality of feedback responses and/or measurements, including those pertaining to position (including orientation), applied force, proximity, temperature, pressure, humidity, etc., of, by, and/or nearby to the instrument arm assembly. For example, the surgical team 904 may be provided with a master input device having manipulators, or the like, having haptic and/or force feedback and designed to map and sense the surgical team's 904 delicate finger-twisting, wrist-bending, and/or other arm/shoulder movements into movements of the instrument arm (such as 230, 240) with high precision, high dexterity, and minimum burden, while also providing feedback of contact resistance (such as tissue resistance).

When an instrument arm assembly (such as 230, 240) comprises one or more illumination sources, cameras, haptic and/or force feedback instruments, and/or other sensors and/or instruments, as described above and in the present disclosure, the instrument arm assembly may also comprise a gas shield, such as the gas shield described above for the image capturing assembly 220. One or more of the instrument arm assemblies (such as 230, 240) may further comprise one or more internal temperature control assemblies operable to control (such as reduce or increase) the temperature of one or more components of the instrument arm assembly.

As illustrated in the example embodiment of FIGS. 2A, 2B, 3A, 3B, FIG. 5A, and FIG. 5B, each of the instrument arm assemblies, including the first instrument arm assembly 230, may comprise a first instrument arm segment (or shoulder section) 231, a second instrument arm segment (or first arm section) 233 (as illustrated in at least FIGS. 5A-B), 360 (as illustrated in at least FIG. 5C), a third instrument arm segment (or second arm section) 235 (as illustrated in at least FIGS. 5A-B), 330 (as illustrated in at least FIG. 5C), and a fourth instrument arm segment (or hand section) 237. The instrument arm assembly 230 may also comprise a first joint portion (or shoulder joint section) 232 having a shoulder sway joint section 380 and shoulder pitch joint section 370; a second joint portion (or elbow section) 234 (as illustrated in at least FIGS. 5A-B), 350 (as illustrated in at least FIG. 5C); a third joint portion (or wrist section) 236 (as illustrated in at least FIGS. 5A-B), axis B (as illustrated in at least FIGS. 5D-H); and an end effector joint portion 238 (as illustrated in at least FIGS. 5A-B), axis A (as illustrated in at least FIGS. 5D-H). Each of the aforementioned joint portions may be configurable, either manually and/or via the computing device (or system), to provide an attached instrument arm segment (and the end effector 239, 342, 344) with one or more in vivo degrees of freedom when the instrument arm assembly is provided in the abdominal cavity of the patient. For example, the first joint portion (or shoulder joint section) 232 may be operable to provide the second instrument arm segment (or first arm section) 233 (as illustrated in at least FIGS. 5A-B), 360 (as illustrated in at least FIG. 5C) with one or two degrees of freedom resembling the one or two degrees of freedom of the human shoulder. Specifically, the shoulder sway joint section 380 (as illustrated in at least FIG. 5M) may be operable to provide the second instrument arm segment (or first arm section) 233 (as illustrated in at least FIGS. 5A-B), 360 (as illustrated in at least FIG. 5C) with a movement (e.g., rotation) relative to axis E (as illustrated in at least FIG. 5M). Furthermore, the shoulder pitch joint section 370 (as illustrated in at least FIG. 5M) may be operable to provide the second instrument arm segment (or first arm section) 233 (as illustrated in at least FIGS. 5A-B), 360 (as illustrated in at least FIG. 5C) with a movement (e.g., rotation) relative to axis D (as illustrated in at least FIG. 5M). As another example, the second joint portion (or elbow section) 234 (as illustrated in at least FIGS. 5A-B), 350 (as illustrated in at least FIG. 5C) may be operable to provide the third instrument arm segment (or second arm section) 235 (as illustrated in at least FIG. 5A-B), 330 (as illustrated in at least FIG. 5C) with one or two degrees of freedom resembling the one or two degrees of freedom of the human elbow. Specifically, the second joint portion (or elbow section) 234 (as illustrated in at least FIGS. 5A-B), 350 (as illustrated in at least FIG. 5C) may be operable to provide the third instrument arm segment (or second arm section) 235 (as illustrated in at least FIG. 5A-B), 330 (as illustrated in at least FIG. 5C) with a movement (e.g., rotation) relative to axis C (as illustrated in at least FIG. 5M). As another example, the third joint portion (or wrist section) 236 (as illustrated in at least FIGS. 5A-B), axis B (as illustrated in at least FIGS. 5D-H) may be operable to provide the fourth instrument arm segment (or hand section) 237 with one or two degrees of freedom resembling the one or two degrees of freedom of the human wrist. Specifically, the third joint portion (or wrist section) 236 (as illustrated in at least FIGS. 5A-B), axis B (as illustrated in at least FIGS. 5D-H) may be operable to provide the fourth instrument arm segment (or hand section) 237 with a movement (e.g., rotation) relative to axis B (as illustrated in at least FIG. 5M). As another example, the end effector joint portion 238 (as illustrated in at least FIGS. 5A-B), axis A (as illustrated in at least FIGS. 5D-H) may be operable to provide the end effector 239, 342, 344 with one or more degrees of freedom. Specifically, the end effector joint portion 238 (as illustrated in at least FIGS. 5A-B), axis A (as illustrated in at least FIGS. 5D-H) may be operable to provide the end effector 239, 342, 344 with a movement (e.g., rotation) relative to axis A (as illustrated in at least FIG. 5M). Accordingly, one or more of the instrument arm assemblies may be configurable, either manually and/or via the computing device/controller, to provide seven or more in vivo degrees of freedom and, together with the at least one to three or more in vitro degree of freedom provided by the port assembly 210 and the controllable swivel assembly 1000 (see FIGS. 10A and 10B), the one or more of the instrument arm assemblies may be configurable, either manually and/or via the computing device/controller, to provide a total of eight to ten or more degrees of freedom. It is recognized herein that the aforementioned at least seven in vivo degrees of freedom for the instrument arm assembly enables at least the full range of natural movements by a surgeon's arm (via a controller/computer-human interface/manipulator/master input device, such as the example illustrated in FIGS. 9A and 9B) to be substantially directly mapped and/or translated to the instrument arm assembly.

Each joint portion, including joint portions 232, 370, 380, 234, 350, and 236 (and the joint portion along axis B) and instrument joint portion 238 (and the joint portion along axis A) may comprise any one or more configurations of gears and/or gear assemblies, including straight gear configurations, planetary gear configurations, beveled gear configurations, spiral beveled gear configurations, hypoid gear configurations, helical gear configurations, worm gear configurations, and/or any other gear configuration without departing from the teachings of the present disclosure. In example embodiments, each instrument arm assembly may also comprise one or more internal integrated motors 332, 334, 336, 339, 362, 364, 366, or the like, operable to actuate (e.g., via first instrument drive portion 332a, second instrument drive portion 334a, wrist drive portion 336a, elbow drive portion 362a, shoulder pitch drive portion 364a, shoulder sway drive portion 366a) the gears of each joint portion (e.g., first instrument driven portion 342a, second instrument driven portion 344a, wrist driven portion 346a, elbow driven portion 352, shoulder pitch driven portion 364b, first shoulder sway driven portion 366b, second shoulder sway driven portion 366c (if needed), third shoulder sway driven portion 366d), including joint portions 232, 370, 380, 234, 350, and 236 (and the joint portions along axis B and axis A) and/or the instrument arm segments 231, 233, 360, 235, 330, and 237. In this regard, each of the integrated motors, joint portions, and/or instrument arm segments described above and in the present disclosure may be operable to communicate, such as receive control commands and/or transmit information, from and/or to the computing device/controller of one or more nearby and/or remotely located surgical teams 904 via wired and/or wireless communication in example embodiments. Furthermore, each of the integrated motors, joint portions, and/or instrument arm segments described above and in the present disclosure may be operable to receive power and/or control signals from an external power source and/or the computing device/controller via wired and/or wireless transmissions in example embodiments.

In an example embodiment, as illustrated in FIGS. 5C-M, an instrument arm assembly (e.g., instrument arm assembly 230, 240) may include an end-effector assembly (e.g., end-effector assembly 340). The instrument arm assembly (e.g., instrument arm assembly 230, 240) may further include a first arm assembly (e.g., first arm assembly 235, 330). The instrument arm assembly (e.g., instrument arm assembly 230, 240) may further include a second arm assembly (e.g., second arm assembly 233, 360).

End-Effector Assembly (e.g., End-Effector Assembly 340).

An example embodiment of the end-effector assembly (e.g., end-effector assembly 340) may comprise a first instrument assembly. The end-effector assembly 340 may also comprise a second instrument assembly. Although the figures illustrate an end-effector assembly having a first instrument and a second instrument, it is to be understood in the present disclosure that the end-effector assembly may have more other instruments or may only have a first instrument or a second instrument without departing from the teachings of the present disclosure. The end-effector assembly 340 may also comprise a wrist assembly.

(i) First Instrument Assembly.

An example embodiment of the first instrument assembly may comprise a first instrument (e.g., first instrument 342) for use in performing a surgical action. The first instrument 342 may be any surgical instrument without departing from the teachings of the present disclosure.

In an example embodiment, the first instrument 342 may be configurable to receive an electric current (e.g., first electric current) applied from a first energy source (not shown) so as to perform actions of an electrosurgical instrument. Although the first instrument may be described above and in the present disclosure to receive an electric current, it is to be understood that the first instrument may also be configurable to receive a voltage potential, thermal energy, heat, cold temperature application, radiation, etc. to perform the said surgical action without departing from the teachings of the present disclosure.

The first instrument assembly may also comprise a first instrument driven portion (e.g., first instrument driven portion 342a). The first instrument driven portion 342a may be configurable to be driven by the first instrument drive portion 332a of the integrated motor 332. The first instrument driven portion 342a may be driven by the first instrument drive portion 332a in such a way as to move the first instrument 342. For example, the first instrument driven portion 342a may be driven to move the first instrument 342 relative to a first axis (e.g., axis A). In this regard, such movement of the first instrument 342 may be a rotation of a distal end of the first instrument 342 relative to a proximal end of the first instrument 342, and such proximal end may serve as a pivot for such movement.

The first instrument driven portion 342a may be any mechanism, device, or the like, configurable to be driven by the first instrument drive portion 332a. For example, the first instrument driven portion 342a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one first instrument driven portion, it is to be understood in the present disclosure that the end-effector assembly may have more than one first instrument driven portions without departing from the teachings of the present disclosure.

In example embodiments wherein the end-effector assembly 340 is detachable (i.e., unsecurable) from the arm assembly 331, it is to be understood that the first instrument drive portion 332a of the integrated motor 332 may be operable to drive the first instrument driven portion 342a when the end-effector assembly 340 is secured (i.e., attached) to the arm assembly 331. Specifically, the first instrument drive portion 332a of the integrated motor 332 may be operable to drive the first instrument driven portion 342a when the wrist connector portion 338 is secured (i.e., attached) to the wrist assembly (as further described below and in the present disclosure) of the end-effector assembly (and more specifically, the connector 348 of the end-effector assembly 340).

In example embodiments wherein the end-effector assembly 340 is detachable (i.e., unsecurable) from the arm assembly 331, it is to be understood that one or more connectable and unconnectable electric wires, cables, or the like, may be provided to enable the first instrument 342 to receive the electric current from the energy source to perform the actions of an electrosurgical instrument.

The first instrument assembly may also comprise a first instrument insulative portion (e.g., first instrument insulative portion 342b). The first instrument insulative portion 342b may be providable between the first instrument 342 and one or more portions of the end-effector assembly 340 so as to electrically isolate (or electrically insulate, thermally isolate, thermally insulate, and the like) the first instrument 342 from the one or more portions of the end-effector assembly 340.

In an example embodiment, the first instrument insulative portion 342b may be providable between the first instrument 342 and the first instrument driven portion 342a so as to electrically isolate (or electrically insulate, thermally isolate, thermally insulate, and the like) the first instrument 342 from the first instrument driven portion 342a. Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the second instrument 344 via the first instrument driven portion 342a and/or other component/portion of the surgical arm assembly.

The first instrument insulative portion 342b may be formed using any one or more of a plurality of materials, such as electrically insulative materials, thermally insulative materials, plastics, elastomers, ceramics, glasses, and minerals. It is to be understood in the present disclosure that other materials may also be used without departing from the teachings of the present disclosure.

The first instrument 342 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the first instrument 342 may include an opening, or the like, for use in receiving and housing at least a portion of the first instrument insulative portion 342b. The first axis (e.g., axis A) may be formed through a center of the opening of the first instrument 342 in example embodiments. Although the opening may be depicted in the figures to be circular in shape and the corresponding exterior portion of the first instrument insulative portion 342b being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

(ii) Second Instrument Assembly.

An example embodiment of the second instrument assembly may comprise a second instrument (e.g., second instrument 344) for use in performing a surgical action. The second instrument 344 may be any surgical instrument without departing from the teachings of the present disclosure.

In an example embodiment, the second instrument 344 may be configurable to receive an electric current (e.g., second electric current) applied from a second energy source (not shown) so as to perform actions of an electrosurgical instrument. Although the second instrument may be described above and in the present disclosure to receive an electric current, it is to be understood that the second instrument may also be configurable to receive a voltage potential, thermal energy, heat, cold temperature application, radiation, etc. to perform the said surgical action without departing from the teachings of the present disclosure.

The second instrument assembly may also comprise a second instrument driven portion (e.g., second instrument driven portion 344a). The second instrument driven portion 344a may be configurable to be driven by the second instrument drive portion 334a of the integrated motor 334. The second instrument driven portion 344a may be driven by the second instrument drive portion 334a in such a way as to move the second instrument 344. For example, the second instrument driven portion 344a may be driven to move the second instrument 344 relative to the first axis (e.g., axis A). In this regard, such movement of the second instrument 344 may be a rotation of a distal end of the second instrument 344 relative to a proximal end of the second instrument 344, and such proximal end may serve as a pivot for such movement.

The second instrument driven portion 344a may be any mechanism, device, or the like, configurable to be driven by the second instrument drive portion 334a. For example, the second instrument driven portion 344a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one second instrument driven portion, it is to be understood in the present disclosure that the end-effector assembly may have more than one second instrument driven portions without departing from the teachings of the present disclosure.

In example embodiments wherein the end-effector assembly 340 is detachable (i.e., unsecurable) from the arm assembly 331, it is to be understood that the second instrument drive portion 334a of the integrated motor 334 may be operable to drive the second instrument driven portion 344a when the end-effector assembly 340 is secured (i.e., attached) to the arm assembly 331. Specifically, the second instrument drive portion 334a of the integrated motor 334 may be operable to drive the second instrument driven portion 344a when the wrist connector portion 338 is secured (i.e., attached) to the wrist assembly (as further described below and in the present disclosure) of the end-effector assembly (and more specifically, the connector 348 of the end-effector assembly 340).

In example embodiments wherein the end-effector assembly 340 is detachable (i.e., unsecurable) from the arm assembly 331, it is to be understood that one or more connectable and unconnectable electric wires, cables, or the like, may be provided to enable the second instrument 344 to receive the electric current from the energy source to perform the actions of an electrosurgical instrument.

The second instrument assembly may also comprise a second instrument insulative portion (e.g., second instrument insulative portion 344b). The second instrument insulative portion 344b may be providable between the second instrument 344 and one or more portions of the end-effector assembly 340 so as to electrically isolate (or electrically insulate, thermally isolate, thermally insulate, and the like) the second instrument 344 from the one or more portions of the end-effector assembly 340. In an example embodiment, the second instrument insulative portion 344b may be providable between the second instrument 344 and the second instrument driven portion 344a so as to electrically isolate (or electrically insulate, thermally isolate, thermally insulate, and the like) the second instrument 344 from the second instrument driven portion 344a. Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the first instrument 342 via the second instrument driven portion 344a and/or other component/portion of the surgical arm assembly.

The second instrument insulative portion 344b may be formed using any one or more of a plurality of materials, such as electrically insulative materials, thermally insulative materials, plastics, elastomers, ceramics, glasses, and minerals. It is to be understood in the present disclosure that other materials may also be used without departing from the teachings of the present disclosure.

The second instrument 344 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the second instrument 344 may include an opening, or the like, for use in receiving and housing at least a portion of the second instrument insulative portion 344b. The first axis (e.g., axis A) may be formed through a center of the opening of the second instrument 344 in example embodiments. Although the opening may be depicted in the figures to be circular in shape and the corresponding exterior portion of the second instrument insulative portion 344b being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

(iii) Cooperation of the First Instrument Assembly and Second Instrument Assembly.

In example embodiments, the first instrument (e.g., first instrument 342) and second instrument (e.g., second instrument 344) may be selectively moveable/drivable independently from one another. In example embodiments, the first instrument 342 and the second instrument 344 may be selectively moveable/drivable in a similar or same manner, such as being moveable/driveable at the same time, for the same duration, for the same distance, and/or with the same output energy. Although the figures illustrate end-effector assembly having a first instrument and a second instrument, it is to be understood in the present disclosure that the end-effector assembly may have more other instruments or may only have a first instrument or a second instrument without departing from the teachings of the present disclosure. For example, the first instrument 342 and the second instrument 344 may cooperate to form a grasper. As another example, the first instrument 342 and the second instrument 344 may cooperate to form scissors. As another example, the first instrument 342 and the second instrument 344 may cooperate to form a Maryland grasper. Other forms and types of first instruments and/or second instruments are contemplated in the present disclosure in addition to or in replacement of the first instrument and/or second instrument described above and herein without departing from the teachings of the present disclosure.

For example, as described above, the first instrument 342 may be configurable to receive an electric current (e.g., first electric current) applied from a first energy source (not shown) so as to perform actions of an electrosurgical instrument. In addition to or in replacement, the second instrument 344 may be configurable to receive an electric current (e.g., second electric current) applied from a second energy source (not shown). The first current may be the same in magnitude as but opposite in direction to the second current in example embodiments, and the first energy source may be the same as or different from the second energy source in example embodiments. In such embodiments where the first instrument and second instrument collectively cooperate to form a monopolar electrosurgical instrument, or the like, when a mass (e.g., a tissue mass) is provided between the first instrument 342 and second instrument 344 and an electric current is applied to the first instrument 342 or the second instrument 344, the mass will serve to enable the applied electric current to pass through and aid in cutting, coagulating, desiccating, and/or fulgurating the mass. Similarly, in embodiments where the first instrument and second instrument collectively cooperate to form a bipolar electrosurgical instrument, or the like, when a mass (e.g., a tissue mass) is provided between the first instrument 342 and second instrument 344 and an electric current is applied to the first instrument 342 and the second instrument 344, the mass will serve to enable the applied electric current to pass through and aid in performing a surgical action, including cutting, coagulating, desiccating, cauterizing, and/or fulgurating the mass. Although the first instrument and/or second instrument may be described above and in the present disclosure to receive an electric current, it is to be understood that the first instrument and/or second instrument may also be configurable to receive a voltage potential, thermal energy, heat, cold temperature application, radiation, etc. to perform the said surgical action without departing from the teachings of the present disclosure.

(iv) Wrist Assembly.

The wrist assembly may be securable or secured to the first instrument assembly in example embodiments. The wrist assembly may comprise a wrist driven portion (e.g., wrist driven portion 346a). The wrist assembly may further comprise a connector (e.g., connector 348).

The wrist driven portion 346a may be configurable to be driven by the wrist drive portion 336a of the integrated motor 336. The wrist driven portion 346a may be driven by the wrist drive portion 336a in such a way as to move the first instrument 342. For example, the wrist driven portion 346a may be driven to move the first instrument 342 relative to a second axis (e.g., axis B). In this regard, such movement of the first instrument 342 may be a rotation of a distal end of the first instrument 342 relative to a point on the second axis (e.g., axis B), and such point may serve as a pivot for such movement. In addition to or in replacement, the wrist driven portion 346a may be driven by the wrist drive portion 336a in such a way as to move the second instrument 344. For example, the wrist driven portion 346a may be driven to move the second instrument 344 relative to the second axis (e.g., axis B). In this regard, such movement of the second instrument 344 may be a rotation of a distal end of the second instrument 344 relative to a point on the second axis (e.g., axis B), and such point may serve as a pivot for such movement. In example embodiments, the wrist driven portion 346a may be driven by the wrist drive portion 336a in such a way as to collectively move the first instrument 342 and the second instrument 344. For example, the wrist driven portion 346a may be driven to collectively move the first instrument 342 and the second instrument 344 relative to the second axis (e.g., axis B). In this regard, such movement of the first instrument 342 and the second instrument 344 may be a collective rotation of a distal end of the first instrument 342 and distal end of the second instrument 344 relative to a point on the second axis (e.g., axis B), and such point may serve as a pivot for such movement.

The wrist driven portion 346a may be any mechanism, device, or the like, configurable to be driven by the wrist drive portion 336a. For example, the wrist driven portion 346a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one wrist driven portion, it is to be understood in the present disclosure that the end-effector assembly may have more than one wrist driven portions without departing from the teachings of the present disclosure.

Arm Assemblies (e.g., First Arm Assembly 235 and 330, Second Arm Assembly 233 and 360).

(i) First Arm Assembly (e.g., First Arm Assembly 235, 330).

An example embodiment of the first arm assembly (e.g., first arm assembly 235, 330) is illustrated in at least Figures A-M. The arm assembly 330 may be securable to the end-effector assembly 340. In an example embodiment, the arm assembly 330 may be securable to and unsecurable from (e.g., detached) the end-effector assembly 340. As illustrated in FIGS. 5C and 5J, the arm assembly 330 may include an arm assembly body (e.g., arm assembly body 330') having a first end 330a and a second end 330b opposite to the first end 330a. The arm assembly joint portion 350 (or elbow section) may be secured to the first end 330a of the arm assembly body 330'. The wrist connector portion 338 may be provided at the second end 330b of the arm assembly body 330'. The arm assembly body 330' may securely house one or more of a plurality of drive assemblies.

In an example embodiment, the arm assembly body 330' may securely house a first instrument drive assembly. The first instrument drive assembly may include a first integrated motor (e.g., first integrated motor 332) and a first instrument drive portion (e.g., first instrument drive portion 332a). The first instrument drive portion 332a may be provided at the second end 330b of the arm assembly body 330'. The first instrument drive portion 332a may be controllable by the first integrated motor 332 to drive the first instrument driven portion 342a when the wrist connector portion 338 is secured to the wrist assembly 348. The first instrument drive portion 332a may be any mechanism, device, or the like, configurable to drive the first instrument driven portion 342a. For example, the first instrument drive portion 332a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one first instrument drive portion 332a, it is to be understood in the present disclosure that the arm assembly may have more than one first instrument drive portions 332a without departing from the teachings of the present disclosure.

The arm assembly body 330' may also securely house a second instrument drive assembly in example embodiments.

The second instrument drive assembly may include a second integrated motor (e.g., second integrated motor 334) and a second instrument drive portion (e.g., second instrument drive portion 334a). The second instrument drive portion 334a may be provided at the second end 330b of the arm assembly body 330'. The second instrument drive portion 334a may be controllable by the second integrated motor 334 to drive the second instrument driven portion 344a when the wrist connector portion 338 is secured to the wrist assembly 348. The second instrument drive portion 334a may be any mechanism, device, or the like, configurable to drive the second instrument driven portion 344a. For example, the second instrument drive portion 334a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one second instrument drive portion 334a, it is to be understood in the present disclosure that the arm assembly may have more than one second instrument drive portions 334a without departing from the teachings of the present disclosure.

The arm assembly body 330' may also securely house a wrist drive assembly in example embodiments. The wrist drive assembly may include a third integrated motor (e.g., third integrated motor 336) and a wrist drive portion (e.g., wrist drive portion 336a). The wrist drive portion 336a may be provided at the second end 330b of the arm assembly body 330'. The wrist drive portion 336a may be controllable by the third integrated motor 336 to drive the wrist driven portion 346a when the wrist connector portion 338 is secured to the wrist assembly 348. The wrist drive portion 336a may be any mechanism, device, or the like, configurable to drive the wrist driven portion 346a. For example, the wrist drive portion 336a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one wrist drive portion 336a, it is to be understood in the present disclosure that the arm assembly may have more than one wrist drive portions 336a without departing from the teachings of the present disclosure.

The arm assembly body 330' may also securely house a first arm assembly drive assembly in example embodiments. The first arm assembly drive assembly may include a fourth integrated motor (e.g., fourth integrated motor 339) and a first arm assembly drive portion (e.g., first arm assembly drive portion 339a). The first arm assembly drive portion 339a may be provided at the first end 330a of the arm assembly body 330'. The first arm assembly drive portion 339a may be controllable by the fourth integrated motor 339 to drive the first arm assembly body 330' to move relative to the first arm assembly joint portion 350. The first arm assembly drive portion 339a may be any mechanism, device, or the like, configurable to drive the first arm assembly body 330' to move relative to the first arm assembly joint portion 350. For example, the first arm assembly drive portion 339a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one first arm assembly drive portion 339a, it is to be understood in the present disclosure that the arm assembly may have more than first arm assembly drive portions 339a without departing from the teachings of the present disclosure.

Although the figures illustrate the first arm assembly (e.g., first arm assembly 235, 330) having the first integrated motor 332, second integrated motor 334, third integrated motor 336, fourth integrated motor 339, first instrument drive portion 332a, second instrument drive portion 334a, wrist drive portion 336a, and first arm assembly drive portion 339a, it is to be understood that the first arm assembly (e.g., first arm assembly 235, 330) may include the first integrated motor 332, second integrated motor 334, third integrated motor 336, fourth integrated 339, first instrument drive portion 332a, second instrument drive portion 334a, wrist drive portion 336a, and/or first arm assembly drive portion 339a, and/or may also include other integrated motor(s) and/or other drive portions, without departing from the teachings of the present disclosure. It is also to be understood that the first integrated motor 332, second integrated motor 334, third integrated motor 336, fourth integrated motor 339, first instrument drive portion 332a, second instrument drive portion 334a, wrist drive portion 336a, and/or first arm assembly drive portion 339a may be located, in part or in whole, in the first arm assembly (e.g., first arm assembly 235, 330), second arm assembly (e.g., second arm assembly 233, 360), and/or any other location without departing from the teachings of the present disclosure.

(ii) Second Arm Assembly (e.g., Second Arm Assembly 233, 360)

An example embodiment of the second arm assembly (e.g., second arm assembly 233, 360) is illustrated in at least FIGS. 5A-C and 5L-O. The second arm assembly 360 may be securable to the first arm assembly 330 on one end and securable to the shoulder section 231 on another end. When secured to the shoulder section 231, the second arm assembly 360 may be configurable to move in one or more of a plurality of ways relative to the shoulder section 231, including, but not limited to, pitch, yaw, and/or roll relative to the shoulder section 231. In an example embodiment, the second arm assembly 360 may be securable to and unsecurable from (e.g., detached) the first arm assembly 330. As illustrated in FIGS. 5L-N, the second arm assembly 360 may include a second arm assembly body or housing (e.g., second arm assembly body 360') having a first end 360a and a second end 360b opposite to the first end 360a. The arm assembly joint portion 350 (or elbow section) may be secured to the second end 360b of the second arm assembly body 360'. The shoulder pitch joint portion 370 may be provided at the first end 360a of the second arm assembly body 360'. In example embodiments, the shoulder sway joint portion 380 may also be provided at the first end 360a of the second arm assembly body 360'. The second arm assembly body 360' may securely house one or more of a plurality of drive assemblies.

In an example embodiment, the second arm assembly body 360' may securely house an elbow drive assembly. The elbow drive assembly may include a fifth integrated motor (e.g., fifth integrated motor 362) and an elbow drive portion (e.g., elbow drive portion 362a). The elbow drive portion 362a may be provided at the second end 360b of the second arm assembly body 360'. The elbow drive portion 362a may be controllable by the fifth integrated motor 362 to drive the elbow driven portion 352. The elbow drive portion 362a may be any mechanism, device, or the like, configurable to drive the elbow driven portion 352. For example, the elbow drive portion 362a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one elbow drive portion 362a, it is to be understood in the present disclosure that the second arm assembly may have more than one elbow drive portions 362a without departing from the teachings of the present disclosure.

The second arm assembly body 360' may also securely house a shoulder pitch drive assembly in example embodiments. The shoulder pitch drive assembly may include a sixth integrated motor (e.g., sixth integrated motor 364) and a shoulder pitch drive portion (e.g., shoulder pitch drive portion 364a). The shoulder pitch drive portion 364a may be provided at the first end 360a of the second arm assembly body 360'. The shoulder pitch drive portion 364a may be controllable by the sixth integrated motor 364 to drive the shoulder pitch driven portion 364b. The shoulder pitch drive portion 364a may be any mechanism, device, or the like, configurable to drive the shoulder pitch driven portion 364b. For example, the shoulder pitch drive portion 364a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one shoulder pitch drive portion 364a, it is to be understood in the present disclosure that the second arm assembly may have more than one shoulder pitch drive portions 364a without departing from the teachings of the present disclosure.

The second arm assembly body 360' may also securely house a shoulder sway drive assembly in example embodiments. The shoulder sway drive assembly may include a seventh integrated motor (e.g., seventh integrated motor 366) and a shoulder sway drive portion (e.g., shoulder sway drive portion 366a). The shoulder sway drive portion 366a may be provided at the first end 360a of the second arm assembly body 360'. The shoulder sway drive portion 366a may be controllable by the seventh integrated motor 366 to drive the first shoulder sway driven portion 366b (which in turn drives the second shoulder sway driven portion 366c (if needed) and third shoulder sway driven portion 366d). The shoulder sway drive portion 366a may be any mechanism, device, or the like, configurable to drive the first shoulder sway driven portion 366b. Furthermore, the first shoulder sway driven portion 366b may be any mechanism, device, or the like, configurable to drive the second shoulder sway driven portion 366c. Furthermore, the second shoulder sway driven portion 366c may be any mechanism, device, or the like, configurable to drive the third shoulder sway driven portion 366d. For example, one or more of the shoulder sway drive portion 366a, first shoulder sway driven portion 366b, second shoulder sway driven portion 366c, and third shoulder sway driven portion 366d may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one shoulder sway drive portion 366a, one first shoulder sway driven portion 366b, one second shoulder sway driven portion 366c, one third shoulder sway driven portion 366d, it is to be understood in the present disclosure that the second arm assembly may have more than one shoulder sway drive portions 366a, more than one first shoulder sway driven portion 366b, more than one second shoulder sway driven portions 366c, and/or more than one third shoulder sway driven portions 366d without departing from the teachings of the present disclosure. Furthermore, it is to be understood in the present disclosure that the second arm assembly may or may not have second shoulder sway driven portion 366c, and/or may or may not have one or more additional or other intermediate shoulder sway driven portions between the shoulder sway drive portion 366a and the third shoulder sway driven portion 366d without departing from the teachings of the present disclosure.

Although the figures illustrate the second arm assembly (e.g., second arm assembly 233, 360) having the fifth integrated motor 362, sixth integrated motor 364, seventh integrated motor 366, elbow drive portion 362a, shoulder pitch drive portion 364a, and shoulder sway drive portion 366a, it is to be understood that the second arm assembly (e.g., second arm assembly 233, 360) may include the fifth integrated motor 362, sixth integrated motor 364, seventh integrated motor 366, elbow drive portion 362a, shoulder pitch drive portion 364a, and/or shoulder sway drive portion 366a, and/or may also include other integrated motor(s) and/or other drive portions, without departing from the teachings of the present disclosure. It is also to be understood that the fifth integrated motor 362, sixth integrated motor 364, seventh integrated motor 366, elbow drive portion 362a, shoulder pitch drive portion 364a, and/or shoulder sway drive portion 366a may be located, in part or in whole, in the first arm assembly (e.g., first arm assembly 235, 330), second arm assembly (e.g., second arm assembly 233, 360), and/or any other location without departing from the teachings of the present disclosure.

Each of the instrument arm assemblies may be securable to (and unsecured from) the anchor ports 216 of the port assembly 210 via a securing portion 231a of the shoulder section 231. It is recognized in the present disclosure that the instrument arm assembly 230, 240 may be secured to the anchor port 216 of the port assembly 210 in the forward-directed position (e.g., as illustrated in FIGS. 2B and 3B) and/or the reverse-directed position (e.g., as illustrated in FIGS. 2A and 3A). Furthermore, in example embodiments, the instrument arm assembly 230, 240 may or may not be transitioned between the forward-directed position and the reverse-directed position. In example embodiments where the instrument arm assembly 230, 240 is transitionable between the forward-directed position and the reverse-directed position, such transition may be performable before, during, and/or after the securing of the shoulder section 231 to the anchor port 216 of the port assembly 210. For example, in such embodiments, the securing portion 231*a* may be adjustably changed in position relative to the shoulder section 231, such as from the forward-directed position illustrated in FIG. 5A to the reverse-directed position illustrated in FIG. 5B, and vice versa.

One or more internal temperature control assemblies (not shown) may be provided for each of the one or more instrument arm assemblies 230, 240. Each internal temperature control assembly may be operable to control (such as reduce) the temperature and/or heat emission of the aforementioned gears and/or gear assemblies, motors, instrument joint portions (such as 232, 370, 380, 234, 236, joint portion along axis A, and/or joint portion along axis B), and/or instrument arm segments (such as 231, 233, 360, 235, 330, and/or 237). The one or more internal temperature control assemblies may also be operable to control (such as increase or decrease) the temperature of the end effector 239, 342, 344 (which may be desirable when the end effector 239, 342, 344 is a cutting tool, or the like). In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well any solids (if used), may be provided through an interior of the instrument arm assembly without increasing dimensions (such as diameter) of the instrument arm assembly.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the body cavity, such as via an opening (not shown). When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the instrument arm assembly 230, 240.

In example embodiments, the internal temperature control assembly may utilize a combination of gases, liquids, solids, and/or the like without departing from the teachings of the present disclosure.

After the instrument arm assembly 230, 240 has been inserted and attached (or secured) to the port assembly 210, the end effector 239, 342, 344 may be configurable, either manually and/or via the computing device (or system), to apply between about 0 to 20 N of force via the integrated motors 332, 334 when performing surgical actions and procedures, such as clipping and/or grasping actions. Furthermore, the end effector 239, 342, 344 may be configurable, either manually and/or via the computing device/controller, to apply between about 0 to 10 N of force via the integrated motors 332, 334, 336, 338 when performing other surgical actions and procedures, such as translational, twisting, pulling, and/or pushing actions. It is to be understood in the present disclosure that the above range of applicable force are merely an illustration of example embodiments, and as such the range of applicable force may be smaller or larger than those recited above without departing from the teachings of the present disclosure.

In an example embodiment, the instrument arm segments, including the first instrument arm segment 231, the second instrument arm segment 233, 360, the third instrument arm segment 235, 330, and/or the fourth instrument arm segment 237, may be substantially cylindrical in shape. The instrument arm segments, including the first instrument arm segment 231, the second instrument arm segment 233, 360, the third instrument arm segment 235, 330, and/or the fourth instrument arm segment 237, may also be formed in any one of a plurality of other shapes, sizes, and/or dimensions without departing from the teachings of the present disclosure.

As described above, the instrument arm assembly 230, 240 may also include one or more securing portions 231*a*. The securing portion 231*a* may be attachable or attached to the first instrument arm segment 231, a part of the first instrument arm segment 231, and/or formed as a unitary article with the first instrument arm segment 231. Such securing portions 231*a* may be for use in securing the instrument arm assembly 230, 240 to the anchor ports 216. Such securing portions 231*a* may also be for use in performing or assisting in performing the process of inserting the instrument arm assembly 230, 240 into and securing onto the port assembly 210 in example embodiments.

After the instrument arm assembly 230 is inserted through the port assembly 210 and into the cavity of a patient (such as a vagina or rectum), the securing portion 231*a* of the first instrument arm segment (or shoulder section) 231 may be securely received by the anchor port 216 of the port assembly 210.

In an example embodiment, the length of the securing portion 231*a* may be between about 350 to 450 mm, the length of the first instrument arm segment 231 may be between about 15 to 40 mm, the length of the second instrument arm segment 233, 360 may be between about 80 to 105 mm, the length of the third instrument arm segment 235, 330 may be between about 65 to 90 mm, the length of the fourth instrument arm segment 237 may be between about 5 to 30 mm, and the overall length of the collective instrument arm may be between about 165 to 265 mm. In example embodiments, the length of the securing portion 231*a* may be between about 340 to 400 mm, the length of the first instrument arm segment 231 may be between about 15 to 25 mm, the length of the second instrument arm segment 233, 360 may be between about 90 to 100 mm, the length of the third instrument arm segment 235, 330 may be between about 75 to 85 mm, the length of the fourth instrument arm segment 237 may be between about 15 to 25 mm, and the overall length of the collective instrument arm may be between about 195 to 235 mm. In example embodiments, a length of one or more of the instrument arm segments, the securing portion 231*a*, and/or the end effector 239, 342, 344 may also be adjustable by the computing device (or system) of one or more nearby and/or remotely located surgical teams 904 before, during, and/or after insertion of the instrument arm assembly into the cavity of the patient. The outer diameter of one or more of the instrument arm segments may be about 10 to 16 mm. In an example embodiment, the outer diameter of one or more of the instrument arm segments may be about 16 mm.

Each of the instrument arm assemblies, including the securing portion 231*a*, the first instrument arm segment 231, the second instrument arm segment 233, 360, the third instrument arm segment 235, 330, the fourth instrument arm segment 237, the end effector 239, 342, 344, the first joint portion 232, the shoulder sway joint portion 380, the shoulder pitch joint portion 370, the second (or elbow) joint portion 234, 350, the third joint portion 236 (or joint portion along axis B), and/or the instrument joint 238 (or joint portion along axis A), may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. It is to be understood in the present disclosure that other materials may also be used without departing from the teachings of the present disclosure.

The Assistant Arm Assemblies (e.g., Assistant Arm Assembly 250, 260)

In an example embodiment, the surgical device 200 may comprise one or more assistant arm assemblies (e.g., assistant arm assembly 250 or 260) configurable to be inserted into and attach to the port assembly 210. As illustrated in FIGS. 2A, 2B, 3A, and 3B, one or more of the assistant arm assemblies may be a suction/irrigation assembly 250 or an assistant instrument arm assembly such as a retractor arm assembly 260, and each of them may include a multi-curvable body 252 or 262, respectively, and an anchoring portion, respectively (e.g., similar to the multi-curvable body 222 and anchoring portion 220*a* of the image capturing assembly 220).

As illustrated in FIGS. 2A, 2B, 3A, and 3B, the suction/irrigation assembly 250 may include an end having a suction port 259 for applying a suction or negative pressure, which may be for use in removing liquids (e.g., blood, etc.) from the cavity of the patient. In respect to the assistant instrument arm assembly 260, the assistant instrument arm assembly 260 may include an end having an instrument 269, such as a gripper, retractor, cutter, needle, or the like, which may be for use in assisting the one or more instrument arm assemblies 230 and/or 240 in performing the surgical action.

As illustrated in the example embodiment of FIGS. 2A, 2B, 3A, and 3B, the assistant arm assemblies 250 and/or 260 may comprise a multi-curvable body 252 and/or 262, respectively, attached to their ends (suction port or instrument, respectively). The multi-curvable body 252 or 262 may be any elongated multi-curvable body similar to that of the image capturing assembly 220 described above and in the present disclosure that can be controlled/configured by the surgical team 904 (such as via the computing device/controller/manipulator/master input device) to, among other things, straighten and/or curve (and hold such a straightness and/or curvature) at one or more of a plurality of locations along the multi-curvable body 252 or 262, curve (and hold such a curvature) in one or more of a plurality of curvatures, and/or straighten and/or curve (and hold such a straightness and/or curvature) in one or more of a plurality of directions. It is to be understood that, when the multi-curvable body 252 or 262 is configured to curve at any location along the multi-curvable body 252 or 262, the curve may be held and/or released (or configured to uncurve, curve less, or straighten) by the surgical team 904 (such as via the computing device/controller/manipulator/master input device).

The multi-curvable body 252 or 262 may be formed in any one or more ways known in the art. For example, the multi-curvable body 252 or 262 may be a unitary or substantially unitary elongated body having a plurality of wires, cables, or the like, distributed/run throughout the multi-curvable body 252 or 262 in such a way that a manipulating, such as a pulling/releasing, shortening/lengthening, tightening/loosening, etc., of one or a combination of such wires, cables, or the like enables the above-mentioned curving of one or more locations of the multi-curvable body 252 or 262 in one or more curvatures and in one or more directions. As another example, the multi-curvable body 252 or 262 may include a plurality of segments, each segment linked to an adjacent segment in such a way that the segment may be controlled/configured to be pivotly positioned in a plurality of positions relative to the adjacent segment. As another example, the multi-curvable body 252 or 262 may include a plurality of springs, gears, motors, etc. for achieving the above-mentioned curving of one or more locations of the multi-curvable body 252 or 262 in one or more curvatures and in one or more directions. It is to be understood in the present disclosure that the multi-curvable body 252 or 262 may also include a combination of one or more of the above-mentioned approaches.

The assistant arm assembly 250 or 260 may be secured to the port assembly 210 in one or more of a plurality of ways, including those described above and in the present disclosure for the instrument arm assemblies 230, 240 and/or the image capturing assembly 220. For example, the assistant arm assembly 250 or 260 may also comprise an anchoring portion (e.g., similar to the anchoring portion 220*a* of the image capturing assembly 220 and/or the securing portion 231*a* of the instrument arm assembly 220), respectively, operable to attach (or secure) the assistant arm assembly 250 or 260 to one or more anchor ports 216 of the port assembly 210.

In an example embodiment, the multi-curvable body 252 or 262 may each be substantially cylindrical in shape. The multi-curvable body 252 or 262 may also be formed in any one of a plurality of other shapes, sizes, and/or dimensions without departing from the teachings of the present disclosure.

In an example embodiment, the length of the multi-curvable body 252 or 262 may be between about 170 to 270 mm. In example embodiments, a length of multi-curvable body 252 or 262 may also be adjustable by the surgical team 904 before, during, and/or after insertion of the camera arm assembly into the cavity of the patient. The outer diameter of the multi-curvable body 252 or 262 may be between about 5 to 7 mm. It is to be understood in the present disclosure that the above dimensions are merely an illustration of example embodiments, and as such the dimensions may be smaller or larger than those recited above without departing from the teachings of the present disclosure.

Controller

In example embodiments, the surgical system may include a controller (or computing device, manipulator, and/or master input device). The controller may be configurable to perform one or more of a plurality of operations in and on the surgical system 200. For example, the controller may be configurable to communicate with and/or control one or more elements of the surgical system 200, such as the external anchor 1 or 1000, the port assembly 210, the instrument arm assemblies 230 or 240, the image capturing assembly 220, and/or the assistant arm assemblies 250 or 260. The controller may be accessible and/or controllable by the surgical team 904, and the surgical team may be able to communicate with and/or control the configuring and/or operation of the one or more elements of the surgical system

200. For example, the controller may be configurable to control a movement and action of some or all parts of the instrument arm assemblies 230 or 240, the first gate assembly 212b, the second gate assembly 214b, the movement and action of some or all parts of the image capturing assembly 220 (including the image capturing, temperature control, etc.), the movement and action of some or all parts of the multi-curvable body 222 of the image capturing assembly 220, the movement and action of some or all parts of the multi-curvable body 252 or 262 of the assistant arm assemblies, the movement and action of some or all parts of the assistant arm assemblies 250 or 260, and the like.

Method of Setting Up the Surgical Device 200 in a Forward-Directed Position (e.g., Method 700)

As illustrated in FIG. 7 and FIGS. 8A-E, example embodiments of the surgical device 200 may be configurable to perform a forward-directed surgical action or procedure in one of a plurality of ways. In an example embodiment, the external anchor 1 may be provided and installed/anchored to the stationary object. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210a, secured to the anchor ports 216, and configured in the cavity of the patient. A surgical action or procedure may then be performed in any part, area, and/or quadrant of the cavity of the patient using the surgical device 200. These processes will now be described below with references to at least FIGS. 7, 8A-E, 9B, and 10B.

(1) Providing the External Anchor and Installing the Port Assembly.

In an example embodiment, the external anchor 1 may be provided and installed/anchored to one or more stationary objects, such as a side rail 300 of a surgical table/bed, as illustrated in FIGS. 1A and 1B. One or more segments 2, 6, 10, and 14 of the external anchor 1 may cooperate using one or more joints 4, 8, 12, and 16 of the external anchor 1 to fix the position (including orientation) of the port assembly 210 in or about the opening of the patient.

In an example embodiment, as illustrated in FIGS. 10A and 10B, the external anchor 1 may comprise a controllable swivel assembly 1000 operable to provide one or more additional in vitro degrees of freedom, such as via a first swivel portion 1002, second swivel portion 1004, and/or third swivel portion 1006. The controllable swivel assembly 1000 may further comprise a motor 1002a for the first swivel portion 1002, a motor 1004a for the second swivel portion 1004, a motor 1006a for the third swivel portion 1006, one or more supporting arms 1008, and one or more locks 1010.

The first swivel portion 1002 may be operable to provide, as one of the in vitro degrees of freedom, a translational movement of the port assembly 210 along an axis defined by the elongated length of the port assembly 210, as illustrated by the arrow A. In example embodiments, the translational movement, as illustrated by arrow A, provided by the first swivel portion 1002 may be between about 0 to 50 mm.

The controllable swivel assembly 1000 may further comprise a second swivel portion 1004 operable to provide, as another one of the in vitro degrees of freedom, a torsional or rotational movement of the port assembly 210 about an axis depicted by axis Y. In example embodiments, the torsional or rotational movement, as illustrated by the arrow B, provided by the second swivel portion 1004 may be between about +/−180 degrees.

The controllable swivel assembly 1000 may further comprise a third swivel portion 1006 operable to provide, as another one of the in vitro degrees of freedom, a pivotal or rotational movement of the port assembly 210 about an axis perpendicular to the Y-axis, such as the axis depicted by axis Z (which comes out of the page). In example embodiments, the Z-axis or the center of rotation may be located at about opening of the patient, such as at the mid-point of the abdominal wall. In example embodiments, the pivotal or rotational movement, as illustrated by the arrow C, provided by the third swivel portion 1006 may be between about +/−80 degrees.

It is recognized in the present disclosure that the controllable swivel assembly 1000 may comprise the first swivel portion 1002, second swivel portion 1004, and/or third swivel portion 1006 in example embodiments. The controllable swivel assembly 1000 may further comprise other swivel portions (not shown) when more than three in vitro degrees of freedom and/or movements/rotations other than those providable by the first swivel portion 1002, second swivel portion 1004, and third swivel portion 1006 are desired and/or required.

The controllable swivel assembly 1000, including the first swivel portion 1002, the second swivel portion 1004, and/or the third swivel portion 1006, may be controllable either locally or remotely by the surgical team.

In an example embodiment, the port assembly 210 may be installed and secured to the external anchor 1 or 1000. As illustrated in FIGS. 8A-E, the second end 214 of the port assembly 210 may be inserted into the opening of the patient and into the cavity of the patient and the first end 212 of the port assembly 210 may be secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212b and the second gate assembly 214b may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 8A:
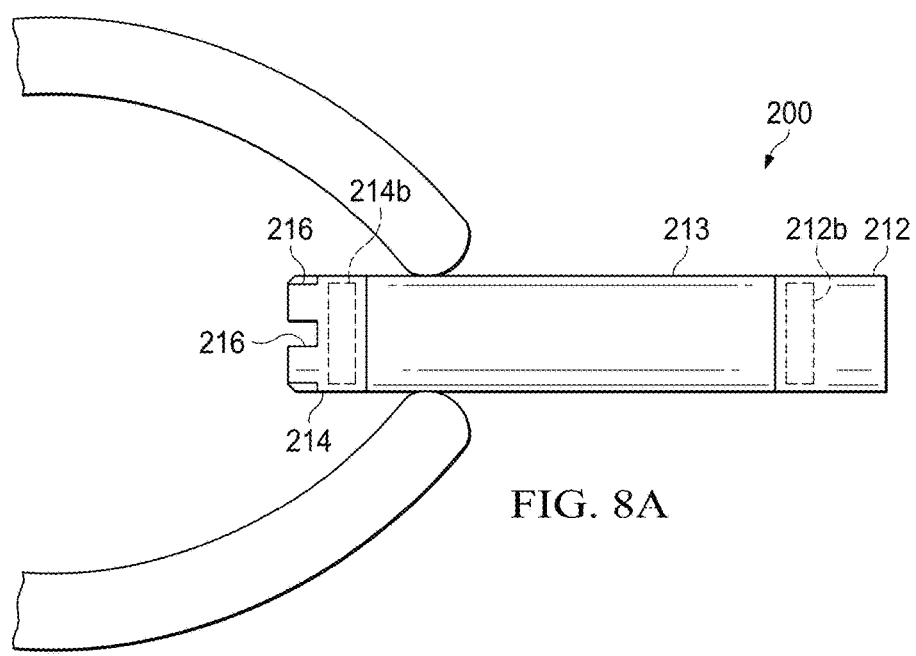
FIGS. 8A-E are illustrations of a side view of an example embodiment of a method of configuring a surgical device in a forward-directed position.

After the workable volume/space in the cavity has been formed and the port assembly 210 is secured in position, as illustrated in FIG. 8A, the image capturing assembly 220 may be inserted through the central access channel 210a and secured to the anchor port 216 of the port assembly 210. To do so while maintaining the workable volume/space, the first gate assembly 212b may be configured to the open position while the second gate assembly 214b is configured to the closed position. Once the first gate assembly 212b is in the open position, the image capturing assembly 220 may be inserted into the mid section 213. The first gate assembly 212b may then be configured to the closed position after the image capturing assembly 220 passes through the first gate assembly 212b. The second gate assembly 214b may then be configured to the open position. It is recognized in the present disclosure that the workable volume/space in the cavity is maintained via the insufflation since the first gate assembly 212b is configured to the closed position. Once the second gate assembly 214b is in the open position, the image capturing assembly 220 may be inserted into the cavity of the patient and the anchor portion 220a secured to an anchor port 216. The second gate assembly 214b may then be configured to the closed position after the image capturing assembly 220 passes through the second gate assembly 214b. The multi-curvable body 222 of the image capturing assembly 220 may then be configured/controlled to curve in one or more locations along the multi-curvable body 222 so that the image capturing assembly 220 can be directed in a forward-directed position (as illustrated in FIGS. 2B and 3B).

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8B:
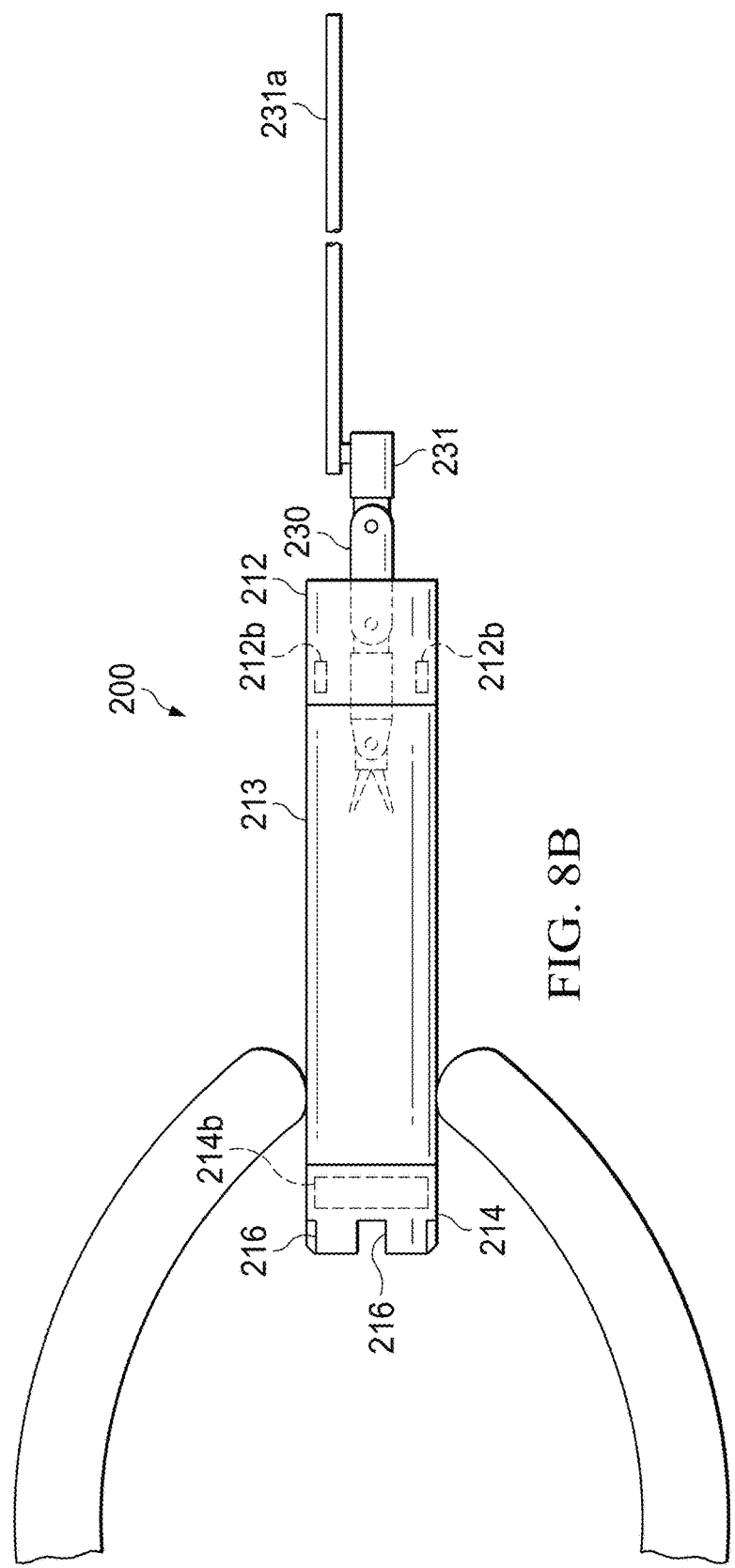
Figure 8C:
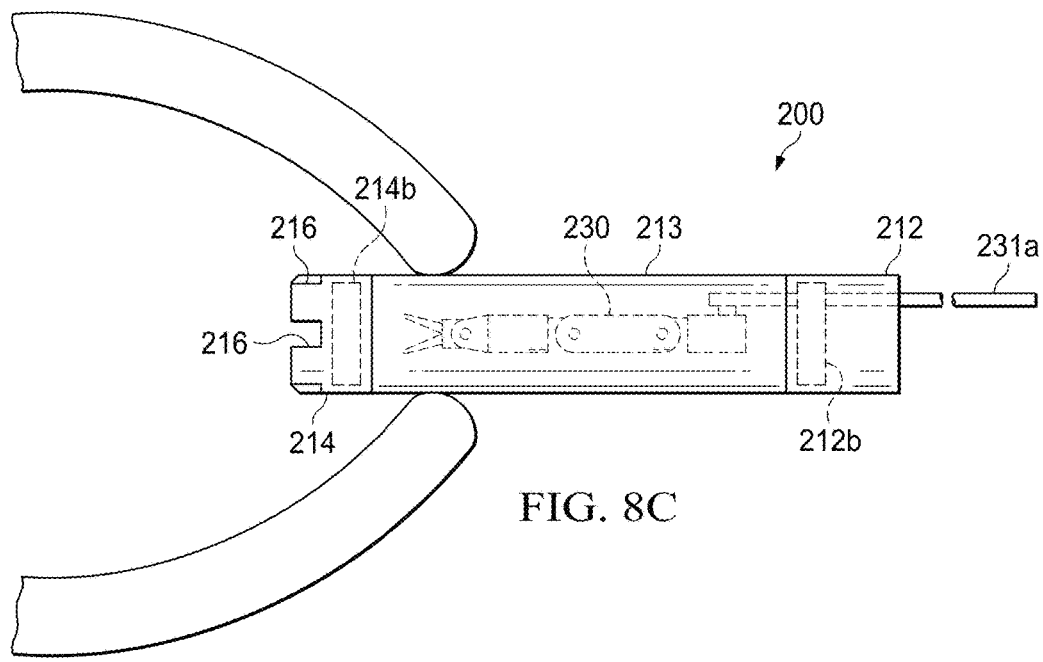
Figure 8D:
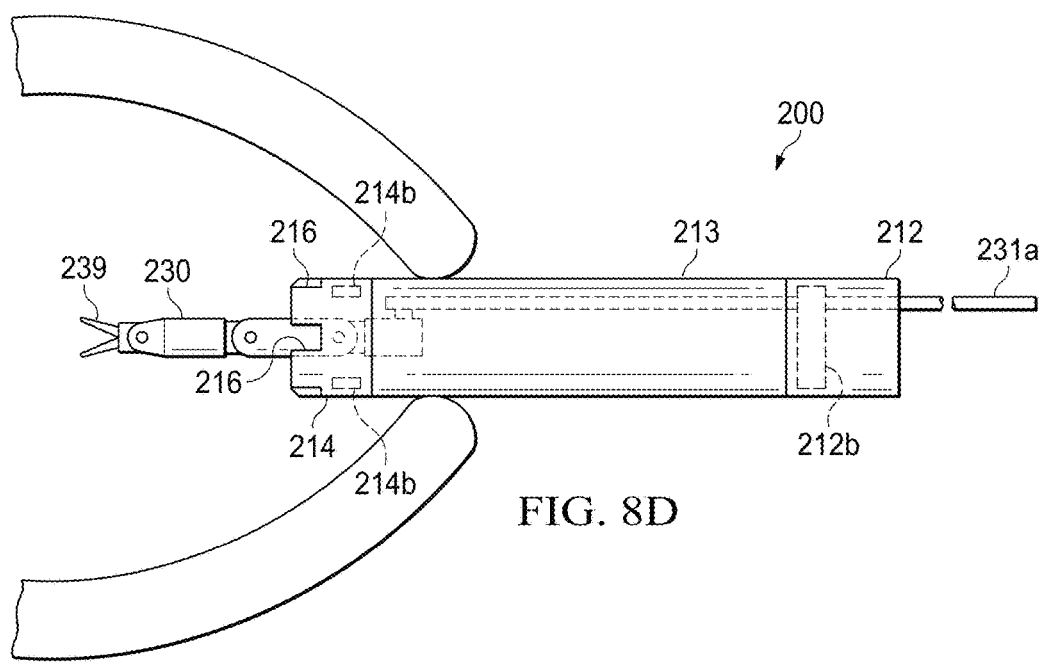
Figure 8E:
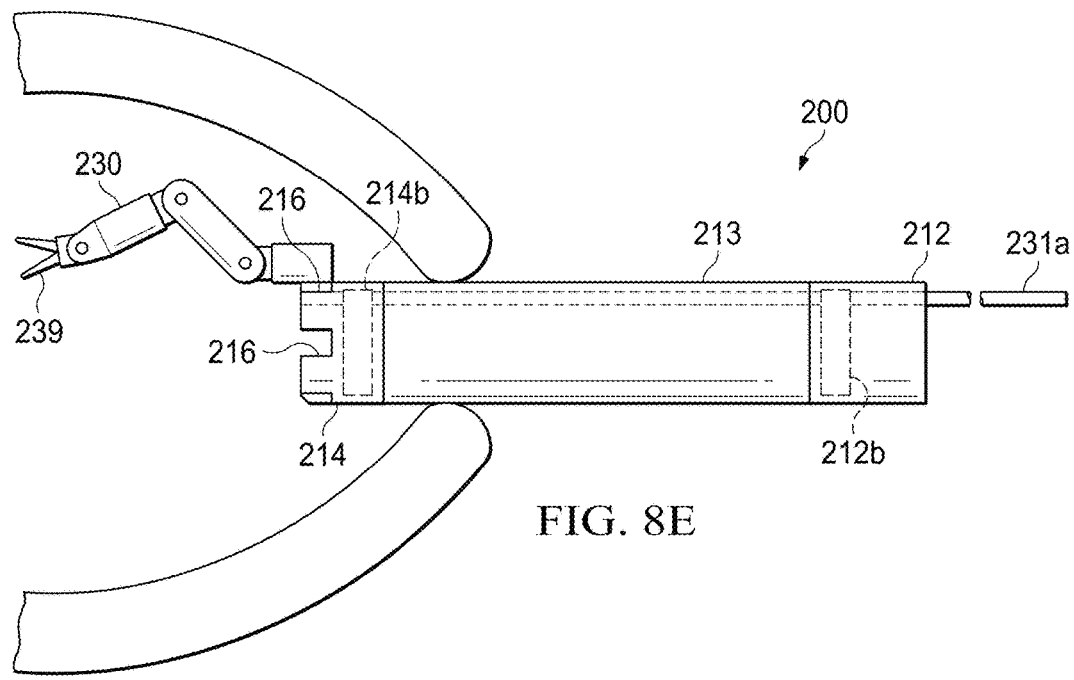

The instrument arm assembly 230 may be inserted through the central access channel 210a and secured to the anchor port 216 of the port assembly 210. To do so while maintaining the workable volume/space, the first gate assembly 212b may again be configured to the open position while the second gate assembly 214b is configured to the closed position. Once the first gate assembly 212b is in the open position, the instrument arm assembly 230 may be inserted into the mid section 213, as illustrated in FIG. 8B. The first gate assembly 212b may then be configured to the closed position after the instrument arm assembly 230 passes through the first gate assembly 212b and into the mid section 213, as illustrated in FIG. 8C. The second gate assembly 214b may then be configured to the open position, as illustrated in FIG. 8D. Once the second gate assembly 214b is in the open position, the instrument arm assembly 230 may be inserted into the cavity of the patient and the securing portion 231a secured to an anchor port 216, as illustrated in FIG. 8E. The second gate assembly 214b may then be configured to the closed position after the instrument arm assembly 230 passes through the second gate assembly 214b.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted into the port assembly 210 via the central access channel 210a in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210a of the port assembly 210 in a substantially reverse manner as described above for the inserting and attaching.

Method of Setting Up the Surgical Device 200 in a Reverse-Directed Position (e.g., Method 700)

As illustrated in FIGS. 7 and 8F-K, example embodiments of the surgical device 200 may be configurable to perform a reverse-directed surgical action or procedure in one of a plurality of ways. In an example embodiment, the external anchor 1 may be provided and installed/anchored to the stationary object in a similar manner as described above and in the present disclosure. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210a, secured to the anchor ports 216, and configured in the cavity of the patient. For the inserting, each of the image capturing assemblies 220, instrument arm assemblies 230 and/or 240, and assistant arm assemblies 250 and/or 260 are inserted in reverse orientation as compared to the forward-directed position described above and in the present disclosure. A surgical action or procedure may then be performed in any part, area, and/or quadrant of the cavity of the patient using the surgical device 200. These processes will now be described below with references to at least FIGS. 7, 8F-K, 9B, and 10B.

(1) Providing the External Anchor and Installing the Port Assembly.

In an example embodiment, the port assembly 210 may be installed and secured to the external anchor 1 or 1000. As illustrated in FIGS. 8A-E, the second end 214 of the port assembly 210 is inserted into the opening of the patient and into the cavity of the patient and the first end 212 of the port assembly 210 is secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212b and the second gate assembly 214b may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 8F:
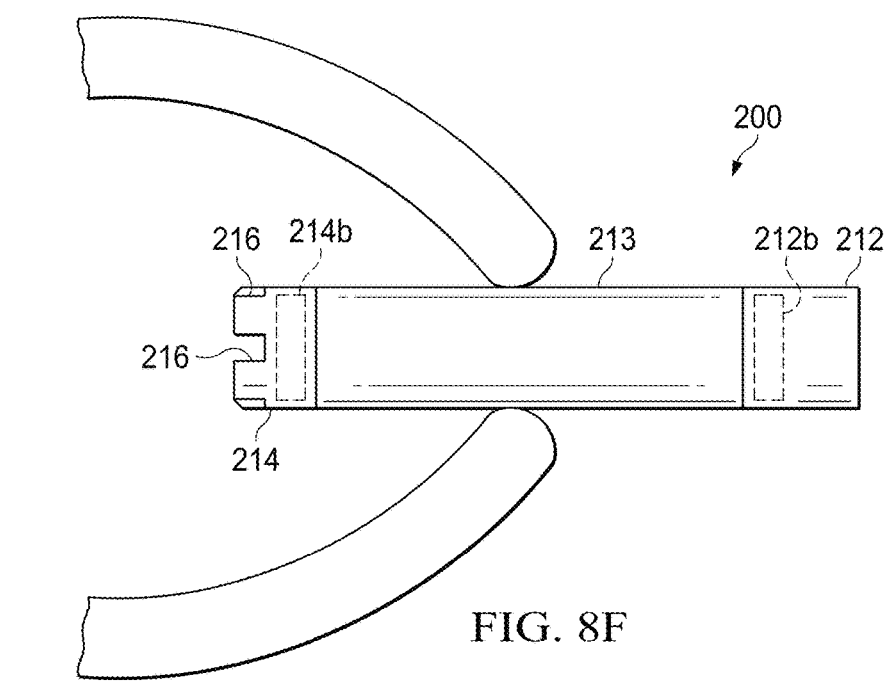
FIGS. 8F-K are illustrations of a side view of an example embodiment of a method of configuring a surgical device in a reverse-directed position.

After the workable volume/space in the cavity has been formed and the port assembly 210 is secured in position, as illustrated in FIG. 8F, the image capturing assembly 220 may be inserted with the image capturing body 224 inserted last through the central access channel 210a and secured to the anchor port 216 of the port assembly 210. To do so while maintaining the workable volume/space, the first gate assembly 212b may be configured to the open position while the second gate assembly 214b is configured to the closed position. Once the first gate assembly 212b is in the open position, the image capturing assembly 220 may be inserted into the mid section 213. The first gate assembly 212b may then be configured to the closed position after the image capturing assembly 220 passes through the first gate assembly 212b. The second gate assembly 214b may then be configured to the open position. It is recognized in the present disclosure that the workable volume/space in the cavity is maintained via the insufflation since the first gate assembly 212b is configured to the closed position. Once the second gate assembly 214b is in the open position, the image capturing assembly 220 may be inserted completely into the cavity of the patient with the image capturing body 224 being closest to the anchor port 216. The multi-curvable body 222 of the image capturing assembly 220 may then be configured/controlled to curve in one or more locations along the multi-curvable body 222 so that the image capturing assembly 220 can be directed in a reverse-directed position next to the outer surface of the port assembly 210 (as illustrated in FIGS. 2A and 3A). The image capturing assembly 220 may then be provided adjacent to the outer surface of the port assembly 210 so that the anchoring portion 220a of the image capturing assembly 220 is adjacent to the anchor port 216. The anchoring portion 220a of the image capturing assembly 220 may then be secured to the anchor port 216. The second gate assembly 214b may be configured to the closed position after the image capturing assembly 220 passes through the second gate assembly 214b.

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8G:
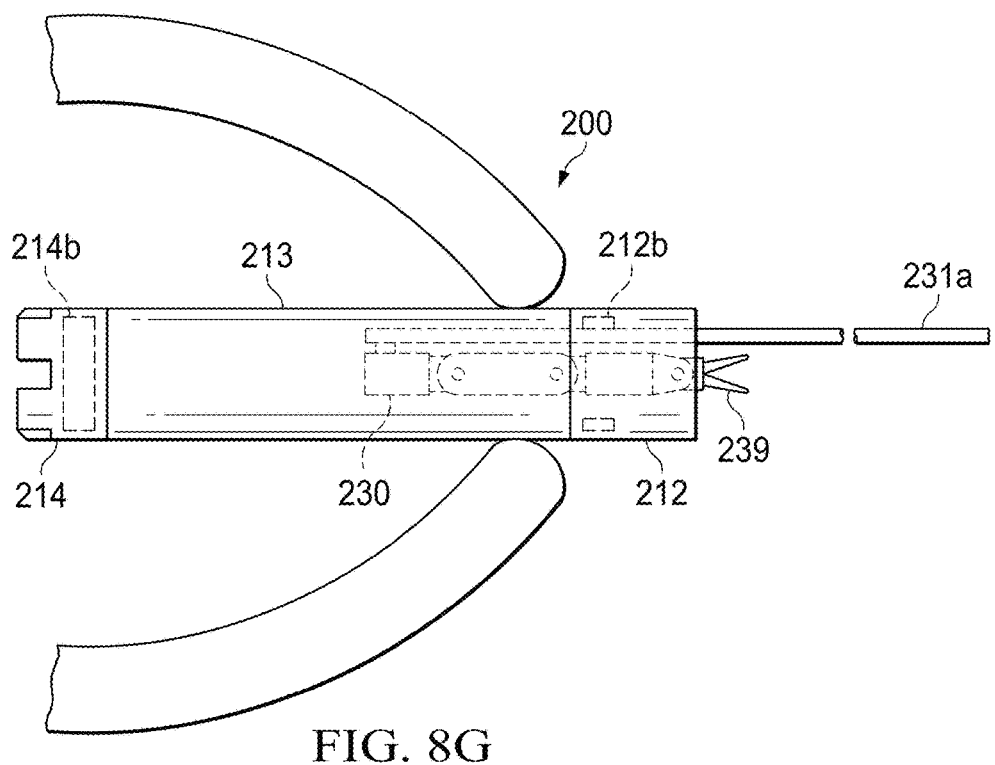
Figure 8H:
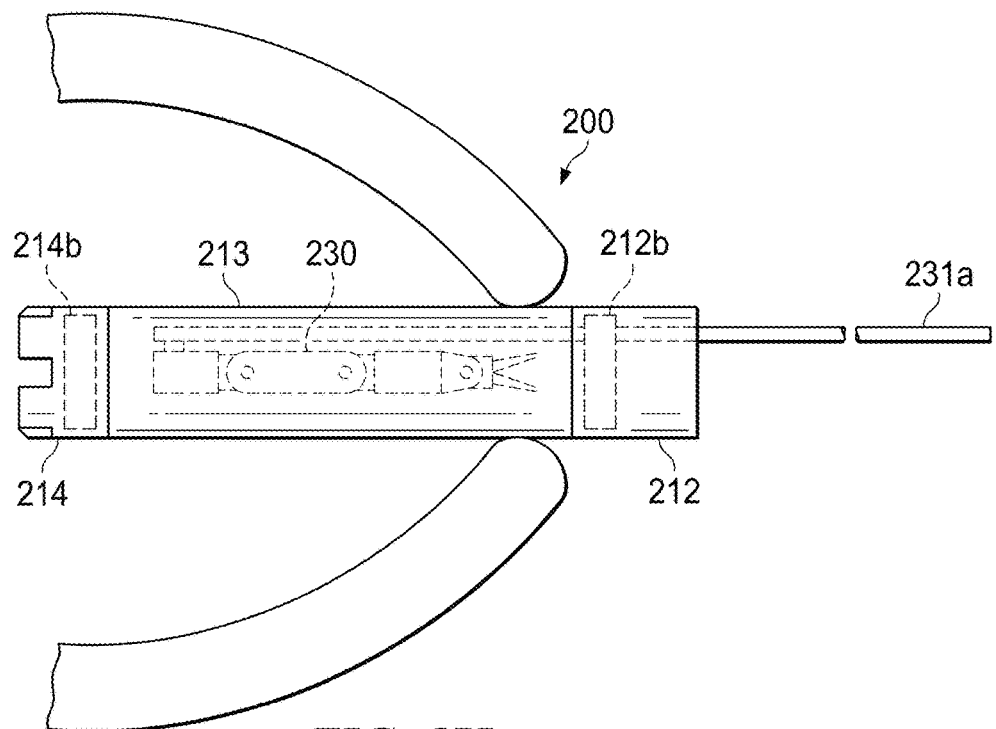
Figure 8I:
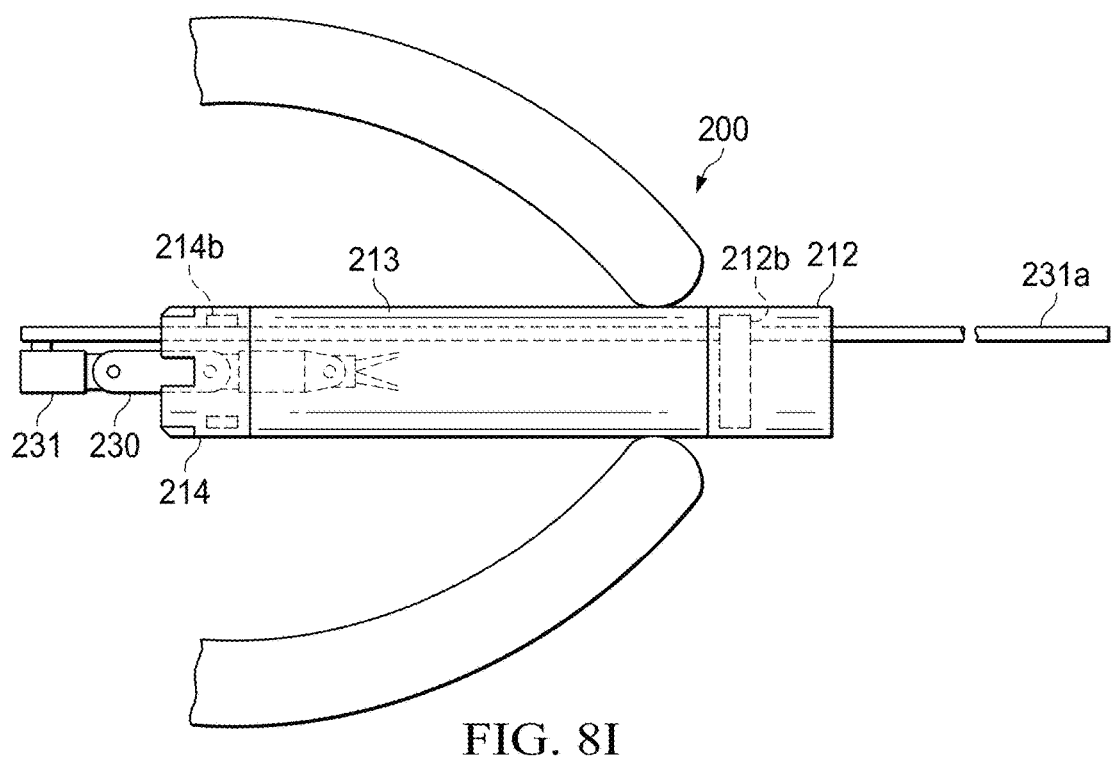
Figure 8J:
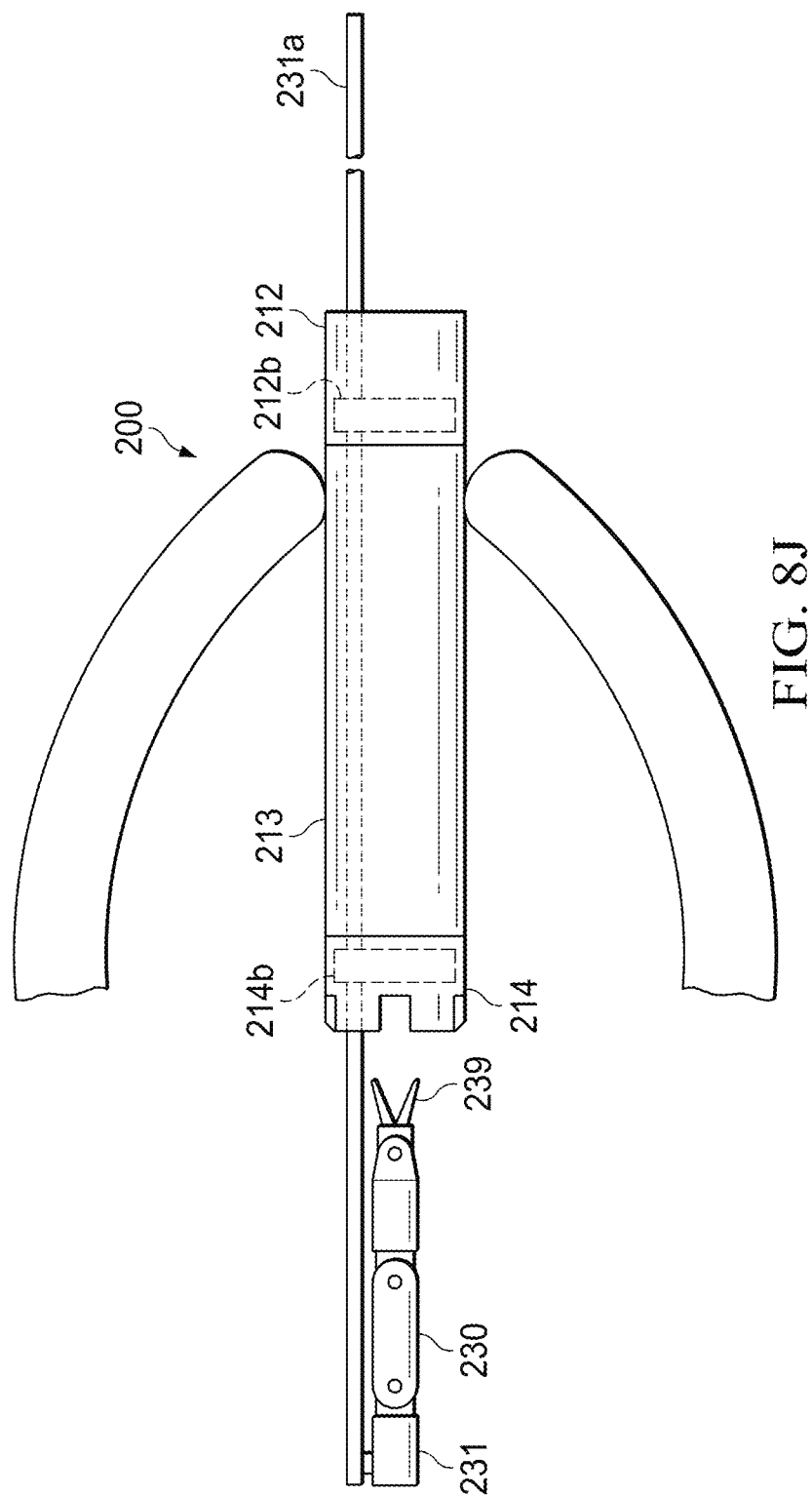
Figure 8K:
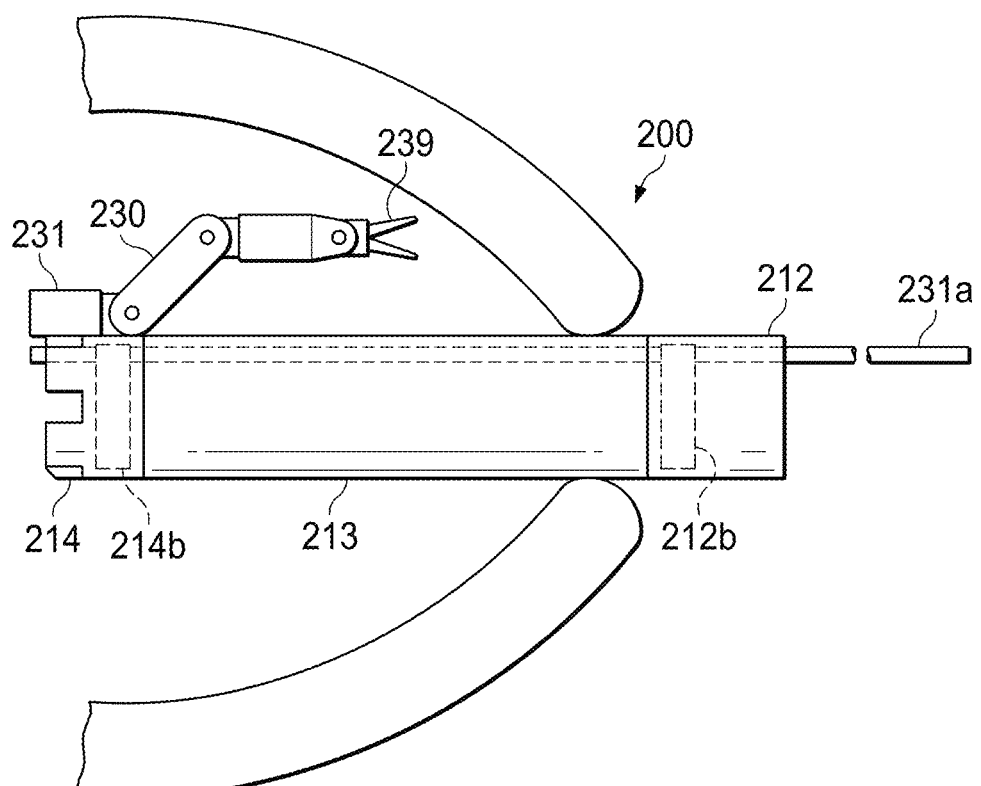

To insert the instrument arm assembly 230 through the central access channel 210a and secure it to the anchor port 216 of the port assembly 210 while maintaining the workable volume/space, the first gate assembly 212b may again be configured to the open position while the second gate assembly 214b is configured to the closed position. Once the first gate assembly 212b is in the open position, the instrument arm assembly 230 may be inserted with the end effector 239, 342, 344 inserted last into the mid section 213, as illustrated in FIG. 8G. The first gate assembly 212b may then be configured to the closed position after the instrument arm assembly 230 passes through the first gate assembly 212b and into the mid section 213, as illustrated in FIG. 8H. The second gate assembly 214b may then be configured to the open position, as illustrated in FIG. 8I. Once the second gate assembly 214b is in the open position, the instrument arm assembly 230 may be inserted completely into the cavity of the patient with the end effector 239, 342, 344 being closest to the anchor port 216, as illustrated in FIG. 8J. The instrument arm assembly 230 may then be turned 180 degrees (if needed) and/or moved so that the instrument arm assembly 230 can be brought next to the outer surface of the port assembly 210. The instrument arm assembly 230 may then be pulled adjacent to the outer surface of the port assembly 210 so that the securing portion 231a of the shoulder section 231 of the instrument arm assembly 230 is adjacent to the anchor port 216. The securing portion 231a of the instrument arm assembly 230 may then be secured to the anchor port 216, as illustrated in FIG. 8K. The second gate assembly 214b may be configured to the closed position at any time after at least the end effector 230 of the instrument arm assembly 230 passes through the second gate assembly 214b.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted and installed in a reverse-directed manner via the central access channel 210a of the port assembly 210 in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210a of the port assembly 210 in a substantially reverse manner as described above for the inserting and attaching in the reverse-directed manner.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A surgical system for use in performing a surgical action, the surgical system comprising:
   an end-effector assembly, the end-effector assembly having:
      a surgical instrument; and
      a wrist assembly securable to the surgical instrument;
   a first arm assembly securable to the wrist assembly at one end and securable to an elbow section at another end;
   a second arm assembly, the second arm assembly having:
      a second arm assembly body having a first end and a second end opposite to the first end, the first end connected to the elbow section and the second end connected to a shoulder section; and
      a first shoulder drive assembly housed in the second arm assembly body, the first shoulder drive assembly having a first integrated motor and a first shoulder drive portion, wherein the first shoulder drive portion is controllable by the first integrated motor to pivotally move the second arm assembly relative a first shoulder axis, the first shoulder axis being an axis located at a location between the second end of the second arm assembly body and the shoulder section;
      a second shoulder drive assembly housed in the second arm assembly body, the second shoulder drive assembly having a second integrated motor and a second shoulder drive portion, wherein the second shoulder drive portion is controllable by the second integrated motor to pivotally move the second arm assembly relative to a second shoulder axis, the second shoulder axis being an axis located at a location between the second end of the second arm assembly body and the shoulder section, the second shoulder axis being a different axis from the first shoulder axis; and
   the shoulder section.

2. The surgical system of claim 1,
   wherein the surgical instrument is configurable to move relative to a first axis; and
   wherein the wrist assembly is configurable to move the surgical instrument relative to a second axis different from the first axis.

3. The surgical system of claim 1,
   further comprising a port assembly;
   wherein the second arm assembly is securable to the port assembly via the shoulder section.

4. The surgical system of claim 1, wherein the end-effector assembly is securable to and unsecurable from the first arm assembly.

5. The surgical system of claim 4, wherein the surgical instrument is configurable to secure to and unsecure from the end-effector assembly.

6. The surgical system of claim 1, wherein the surgical instrument is configurable to further receive a first electric current applied from an energy source so as to perform the actions of an electrosurgical instrument.

7. A surgical system for use in performing a surgical action, the surgical system comprising:
   an end-effector assembly, the end-effector assembly having:
      a surgical instrument; and
      a wrist assembly securable to the surgical instrument;
   a first arm assembly securable to the wrist assembly at a distal end of the first arm assembly and securable to an elbow section at a proximal end of the first arm assembly;
   a second arm assembly securable to the elbow section at a distal end of the second arm assembly, the second arm assembly securable to a shoulder section at a proximal end of the second arm assembly via a first joint and a second joint, the second arm assembly having:
      a first shoulder drive assembly housed in the second arm assembly, the first shoulder drive assembly having a first integrated motor and a first shoulder drive portion, wherein the first shoulder drive portion is controllable by the first integrated motor to pivotally move the second arm assembly relative to a first shoulder axis, the first shoulder axis being an axis located at the first joint; and
      a second shoulder drive assembly housed in the second arm assembly, the second shoulder drive assembly having a second integrated motor and a second shoulder drive portion, wherein the second shoulder drive portion is controllable by the second integrated motor to pivotally move the second arm assembly relative to a second shoulder axis, the second shoulder axis being an axis located at the second joint, the second shoulder axis being a different axis from the first shoulder axis; and the shoulder section.

8. The surgical system of claim 7, wherein the surgical instrument is configurable to move relative to a first axis; and wherein the wrist assembly is configurable to move the surgical instrument relative to a second axis different from the first axis.

9. The surgical system of claim 7, further comprising a port assembly;

wherein the second arm assembly is securable to the port assembly via the shoulder section.

10. The surgical system of claim 7, wherein the end-effector assembly is securable to and unsecurable from the first arm assembly.

11. The surgical system of claim 7, wherein the surgical instrument is configurable to secure to and unsecure from the end-effector assembly.

12. The surgical system of claim 7, wherein the surgical instrument is configurable to receive a first electric current applied from an energy source so as to perform the actions of an electrosurgical instrument.

13. A surgical system for use in performing a surgical action, the surgical system comprising:

a surgical arm, the surgical arm including:
  an end-effector assembly, the end-effector assembly having:
    a surgical instrument; and
    a wrist assembly securable to the surgical instrument;
  a first arm assembly securable to the wrist assembly at a distal end of the first arm assembly and securable to an elbow section at a proximal end of the first arm assembly; and
  a second arm assembly, the second arm assembly having:
    a second arm assembly body having a distal end and a proximal end opposite to the first end, the distal end connected to the elbow section; and
    a first shoulder drive assembly housed in the second arm assembly body, the first shoulder drive assembly having a first integrated motor and a first shoulder drive portion, wherein the first shoulder drive portion is controllable by the first integrated motor to pivotally move the second arm assembly relative to a first axis;
  a second shoulder drive assembly housed in the second arm assembly body, the second shoulder drive assembly having a second integrated motor and a second shoulder drive portion, wherein the second shoulder drive portion is controllable by the second integrated motor to pivotally move the second arm assembly relative to a second axis, the second axis being a different axis from the first axis; and
  an elbow drive assembly housed in the second arm assembly body, the elbow drive assembly having a third integrated motor and an elbow drive portion, wherein the elbow drive portion is controllable by the third integrated motor to pivotally move the first arm assembly relative to the elbow section; and a port assembly, the port assembly having an elongated body with a channel through the elongated body, the channel configurable to allow the surgical arm to pass through the port assembly, the port assembly further including an anchor port configurable to secure the to the port assembly.

14. The surgical system of claim 13, wherein the surgical instrument is configurable to move relative to a third axis; and wherein the wrist assembly is configurable to move the surgical instrument relative to a fourth axis different from the third axis.

15. The surgical system of claim 13, wherein the end-effector assembly is securable to and unsecurable from the first arm assembly.

16. The surgical system of claim 15, wherein the surgical instrument is configurable to secure to and unsecure from the end-effector assembly.

17. The surgical system of claim 13, wherein the surgical instrument is configurable to further receive a first electric current applied from an energy source so as to perform the actions of an electrosurgical instrument.

* * * * *